US007687513B1

(12) United States Patent
Muldoon et al.

(10) Patent No.: US 7,687,513 B1
(45) Date of Patent: Mar. 30, 2010

(54) AMINOPYRIDINIUM IONIC LIQUIDS

(75) Inventors: Mark Muldoon, Wishaw (GB); Joan F. Brennecke, Granger, IN (US); Edward J. Maginn, South Bend, IN (US); Eric F. V. Scriven, Trafalgar, IN (US); Colin H. McAteer, Indianapolis, IN (US); Ramiah Murugan, Indianapolis, IN (US)

(73) Assignee: University of Notre Dame Du Lac, Notre Dame, IN (US)

(*) Notice: Subject to any disclaimer, the term of this patent is extended or adjusted under 35 U.S.C. 154(b) by 542 days.

(21) Appl. No.: 11/254,782

(22) Filed: Oct. 21, 2005

Related U.S. Application Data

(60) Provisional application No. 60/620,421, filed on Oct. 21, 2004, provisional application No. 60/620,420, filed on Oct. 21, 2004.

(51) Int. Cl.
*A01N 43/40* (2006.01)
*A61K 31/435* (2006.01)
(52) U.S. Cl. ..................................... 514/277
(58) Field of Classification Search .................. None
See application file for complete search history.

(56) References Cited

U.S. PATENT DOCUMENTS

| 5,827,602 | A | 10/1998 | Koch et al. |
| 6,232,326 | B1 * | 5/2001 | Nelson ....................... 514/336 |
| 6,579,343 | B2 | 6/2003 | Brennecke et al. |
| 6,638,946 | B2 | 10/2003 | Meth-Cohn et al. |
| 6,939,972 | B2 | 9/2005 | Kumar et al. |

FOREIGN PATENT DOCUMENTS

| DE | 42 17 884 | 2/1993 |
| WO | WO 2006/072775 | 7/2006 |

OTHER PUBLICATIONS

Katritzky et al. Journal of the Chemical Society, Perkin Transactions 2: Physical Organic Chemistry (1972-1999), 1975, 14, 1600-1609.*
U.S. Appl. No. 11/254,781, filed Oct. 2008, Muldoon et al.*
Brennecke, et al., "Ionic Liquids: Innovative Fluids for Chemical Processing," AIChE Journal, 2001, p. 2384-2389, v. 47, n. 11.
Brunelle, et al., "N-alkyl-4-(N', N'-dialkylamino) pyridinium salts: thermally stable phase transfer catalysts for nucleophilic aromatic displacement," Tetrahedron Letters, 1984, p. 3383-3386, v. 25 i. 32, Elsevier Science Ltd.
Yoshida, et al., "Polymer-supported aminopyridinium salts as versatile catalysts for the synthesis of aryl fluorides," Tetrahedron Letters, 1989, p. 7199-7202, v. 30 i. 51, Elsevier Science Ltd.
Kupetis, et al., "1-Alkyl-4-dialkylaminopyridinium Halides as Phase-Transfer Catalysts in Dichlorocarbene Reactions," Monatshefe fur Chemie, 2002, p. 313-321, v. 133, Springer-Verlag.
Blanchard, et al., "A stimulatory phalloid organ in a weaver bird," Nature, 1999, p. 28-29, v. 399.

Blanchard, et al., "Recovery of Organic Products from Ionic Liquids Using Supercritical Carbon Dioxide," Ind. Eng. Chem. Res., 2001, p. 287-292, v. 40, American Chemical Society.
Blanchard, et al., "High-Pressure Phase Behavior of Ionic Liquid/ $CO_2$ Systems," J. Phys. Chem. B, 2001, p. 2437-2444, v. 105, American Chemical Society.
Chang, Kenneth, "With a Splash of Salt, Industry May Reap Environmental Advantages," The New York Times, 2001, p. F.2, i. Apr. 24.
Seddon, Ken, "A working solution?," Economist, 1999, p. 82-83, v. 351 i. 8124.
Fadeev, et al., "Opportunities for ionic liquids in recovery of biofuels," ChemComm, 2001, p. 295-296, The Royal Society of Chemistry.
Crosthwaite, et al., "Phase transition and decomposition temperatures, heat capacities and viscosities of pyridinium ionic liquids," J. Chem. Thermodynamics, 2005, p. 559-568, v. 37, Elsevier Ltd.
Tokuda, et al., "Physicochemical Properties and Structures of Room Temperature Ionic Liquids. 1. Varation of Anionic Species," J. Phys. Chem. B, 2004, p. 16593-16600, v. 108, American Chemical Society.
Hanke, et al., "Intermolecular potentials for simulations of liquid imidazolium salts," Molecular Physics, 2001, p. 801-809, v. 99 n. 10, Taylor & Francis Ltd.
Harold, et al., "Process Engineering in the Evolving Chemical Industry," AIChE Journal, 2004, p. 2123-2127, v. 46 i. 11.
MacFarlane, et al., "Pyrrolidinium Imides: A New Family of Molten Salts and Conductive Plastic Crystal Phases," J. Phys. Chem. B, 1999, p. 4164-4170, v. 103, American Chemical Society.
Pernak, et al., "New Ionic Liquids and Their Antielectrostatic Properties," Ind. Eng. Chem. Res., 2001, p. 2379-2383, v. 40, American Chemical Society.
Welton, Thomas, "Room-Temperature Ionic Liquids. Solvents for Synthesis and Catalysis," Chem. Rev., 1999, p. 2071-2083, v. 99, American Chemical Society.
Wilkes, et al., "Air and Water Stable 1-Ethyl-3-methylimidazolium Based Ionic Liquids," J. Chem. Soc. Chem. Commun, 1992, p. 965-967.
Wasserscheid, et al., "Ionic Liquids—New "Solutions" for Transition Metal Catalysis," Angew. Chem. Int. Ed., 2000, p. 3772-3789, v. 39, Wiley-VCH Verlag GmbH.
Welton, Tom, "Ionic liquids in catalysis," Coordination Chemistry Review, 2003, p. 2459-2477, v. 248, Elsevier B.V.

(Continued)

*Primary Examiner*—James O Wilson
*Assistant Examiner*—Noble Jarrell
(74) *Attorney, Agent, or Firm*—Vedder Price P.C.; Ajay A. Jagtiani

(57) ABSTRACT

Disclosed herein are aminopyridinium cations and compositions containing these cations. Piperidino pyridinium cations and compositions containing these cations are also described. Ionic compositions, particularly liquid ionic compositions that contain the aminopyridinium cation or piperidino pyridinium cation are also described. Methods of enhancing the thermal stability of a compound, particularly an ionic compound, using the aminopyridinium or piperidino pyridinium cations, are also presented. Compositions having an expanded liquidus range of from about −73° C. to about 444° C. are also described. Solvents, heat transfer fluids, and lubricants having improved thermal stability characteristics and an expanded and improved liquidus range are also disclosed.

62 Claims, 19 Drawing Sheets

OTHER PUBLICATIONS

Wilkes, S John, "Properties of ionic liquid solvents for catalysis," Journal of Molecular Catalysis A: Chemical, 2004, p. 11-17, v. 214, Elsevier B.V.

Ito, et al., "Room temperature ionic liquids of alkylimidazolium cations and fluoroanions," Journal of Fluorine Chemistry, 2000, p. 221-227, v. 105, Elsevier Science S.A.

Tokuda, et al., "Physicochemical Properties and Structures of Room Temperature Ionic Liquids. 1. Variation of Anionic Species," J. Phys. Chem. B, 2004, p. 16593-16600, v. 108, American Chemical Society.

Valkenburg, et al., "Thermochemistry of ionic liquid heat-transfer fluids," Thermochimica Acta, 2005, p. 181-188, v. 425, Elsevier B.V.

Nasakin, et al., "Synthesis of 2,6-Disubstituted 3,3,5,5-Tetracyanopiperidines by the Reaction of 1,1,3,3-Tetracyanopropane with 2,4-Diazapentane-1,4-Dienes," Chemistry of Heterocyclic Compounds, 1998, p. 1177-1180, v. 34 n. 10, Kluwer Academic/Plenum Publishers.

Noda, et al., "Pulsed-Gradient Spin—Echo 1H and 19F NMR Ionic Diffusion Coefficient, Viscosity, and Ionic Conductivity of Non-Chloroaluminate Room-Temperature Ionic Liquids," J. Phys. Chem. B, 2001, p. 4603-4610, v. 105, American Chemical Society.

Ngo, et al., "Thermal Properties of imidazolium ionic liquids," Thermochimica Acta, 2000, p. 97-102, Elsevier Science B.V.

Matsumoto, et al., "Room temperature ionic liquids based on small aliphatic ammonium cations and asymmetric amide anions," Chem. Commun., 2002, p. 1726-1727, The Royal Society of Chemistry.

Holbrey, et al., "The phase behaviour of 1-alkyl-3-methylimidazolium tetrafluoroborates; ionic liquids and ionic liquid crystals," J. Chem. Soc., 1999, p. 2133-2139.

MacFarlane, et al., "Low viscosity ionic liquids based on organic salts of the dicyanamide anion," Chem. Commun., 2001, p. 1430-1431. The Royal Society of Chemistry.

Awad, et al., "Thermal degradation studies of alkyl-imidazolium salts and their application in nanocomposites," Thermochimica Acta, 2004, p. 3-11, Elsevier B.V.

Kim, et al., "refractive index and heat capacity of 1-butyl-3-methylimidazolium bromide and 1-butyl-3-methylimidazolium tetrafluoroborate, and vapor pressure of binary systems for 1-butyl-3-methylimidazolium bromide + trifluoroethanol and 1-butyl-3-methylimidazolium tetrafluoroborate + trifluoroethanol," Fluid Phase Equilibria, 2004, p. 214-220, Elsevier B.V.

Kosmulski, et al., "Thermal stability of low temperature ionic liquids revisited," Thermochimica Acta, 2004, p. 47-53, Elsevier B.V.

Yoshizawa, et al., "Ionic Liquids by Proton Transfer: Vapor Pressure, Conuctivity, and the Relevance of ### from Aqueous Solutions," J. Am. Chem. Soc., 2003, p. 15411-15419, v. 125, American Chemical Society.

Patrascu, et al., "New Pyridinium Chiral Ionic Liquids," Heterocycles, p. 2033-2041, v. 63 n.9.

Heintz, et al., "Excess Molar Volumes and Viscosities of Binary Mixtures of Methanol and the Ionic Liquid 4-Methyl-N-butylpyridinium Tetrafluoroborate at 25, 40, and 50 C," Journal of Solution Chemistry, 2002, p. 467-476, v. 31 n. 6, Plenum Publishing Corporation.

Ohno, et al., "Ion conductive characteristics of ionic liquids prepared by neutralization of alkylimidazoles," Solid State Ionics, 2002, p. 303-309, Elsevier Science B.V.

Cammarata, et al., "Molecular states of water in room temperature ionic liquids," Phys. Chem. Chem. Phys., 2001, p. 5192-5200, v. 3, The Owner Societies.

Fredlake, et al., "Thermophysica Properties of Imidazolium-Based Ionic Liquids," J. Chem. Eng. Data, 2004, p. 954-964, v. 49, American Chemical Society.

Crosthwaite, et al., "Liquid Phase Behavior of Imidazolium-Based Ionic Liquids with Alcohols," J. Phys. Chem. B, 2004, p. 5113-5119, v. 108, American Chemical Society.

Fitchett, et al., "1-Alkyl-3-methylimidazolium Bis(perfluoroalkylsulfonyl)imide Water-Immiscible Ionic Liquids," Journal of the Electrochemical Society, 2004, p. E219-E225, v. 141 i. 7, The Electrochemical Society, Inc.

Matsumoto, et al., "Highly Conductive Room Temperature Molten Salts Based on Small Trimethylalkylammonium Cations and Bis(trifluoromethylsulfonyl)imide," Chemistry Letters, 2000, p. 922-923, The Chemical Society of Japan.

McEwen, et al., "Electrochemical Properties of Imidazolium Salt Electrolytes for Electrochemical Capacitor Applications," Journal of the Electrochemical Society, 1999, p. 1687-1695, v. 146 i. 5, The Electrochemical Society, Inc.

Widegren, et al., "The effect of dissolved water on the viscosities of hydrophobic room-temperature ionic liquids," Chem. Commun, 2005, p. 1610-1612, The Royal Society of Chemistry.

Visser, et al., "Traditional Extractants in Nontraditional Solvents: Groups 1 and 2 Extraction by Crown Ethers in Room-Temperature Ionic Liquids," Ind. Eng. Chem. Res., 2000, p. 3596-3604, v. 39, American Chemical Society.

Guterman, Lila, "Weird mixtures replace toxic solvents," New Scientist Print Edition, 1998, p. 13, i. 2150.

Cheek, et al., "Preparation and character..." CA 97-137567 (1982).

Leinen, et al., "Synergistic microbicidal compositions comprising an aminopyridinium compound and a iodopropynyloxethyl carbamate," Abstract.

Crosthwaite, et al., "Phase transistin and decomposition temperatures, heat capacities and viscosities of pyridinium ionic liquids," J. Chem. Thermodynamics 37 (2005) 559-568.

* cited by examiner

CO₂ SOLUBILITY AT 60°C

FIG. 7A

TABLE 5.1 PARTIAL CHANGES AND LENNARD-JONES PARAMETERS FOR PYRIDINIUMS WITH Tf2N.

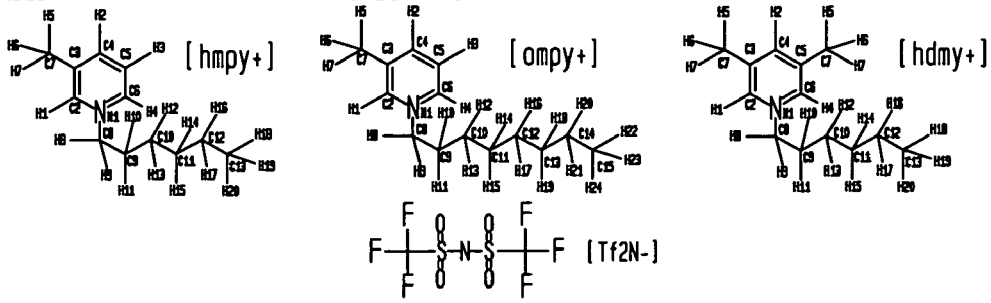

FIG. 7B

PARTIAL ATOMIC CHARGES AND LENNARD-JONES PARAMETERS

| [hmpy+] | | | | | [ompy+] | | | | |
|---|---|---|---|---|---|---|---|---|---|
| ATOM ID | TYPE | Cl (e) | $\sigma$(A) | e(KCalmor$^{-1}$) | ATOM ID | TYPE | Cl (e) | $\sigma$(A) | e(KCalmor$^{-1}$) |
| $C_2$ | CN3B | -0.065575 | 3.207 | 0.1800 | $C_2$ | CN3B | -0.105213 | 3.207 | 0.1800 |
| $C_3$ | CN3 | 0.188823 | 3.385 | 0.0900 | $C_3$ | CN3 | 0.183660 | 3.385 | 0.0900 |
| $C_4$ | CN3A | -0.045264 | 3.207 | 0.1800 | $C_4$ | CN3A | -0.035952 | 3.207 | 0.1800 |
| $C_5$ | CN3 | -0.115651 | 3.385 | 0.0900 | $C_5$ | CN3 | -0.109911 | 3.385 | 0.0900 |
| $C_6$ | CN3B | 0.042383 | 3.207 | 0.1800 | $C_6$ | CN3B | 0.026085 | 3.207 | 0.1800 |
| $N_1$ | NN2 | 0.062369 | 3.296 | 0.2000 | $N_1$ | NN2 | 0.096507 | 3.296 | 0.2000 |
| $H_2$ | HN3B | 0.152953 | 1.604 | 0.0460 | $H_2$ | HN3B | 0.147299 | 1.604 | 0.0460 |
| $H_1$ | HN3B | 0.179939 | 1.604 | 0.0460 | $H_1$ | HN3B | 0.183690 | 1.604 | 0.0460 |
| $H_3$ | HN3B | 0.159195 | 1.604 | 0.0460 | $H_3$ | HN3B | 0.156722 | 1.604 | 0.0460 |
| $H_4$ | HN3B | 0.144454 | 1.604 | 0.0460 | $H_4$ | HN3B | 0.146546 | 1.604 | 0.0460 |
| $C_7$ | CN9 | -0.336621 | 3.635 | 0.0780 | $C_7$ | CN9 | -0.315079 | 3.635 | 0.0780 |
| $H_5$ | HN9 | 0.128512 | 2.388 | 0.0240 | $H_5$ | HN9 | 0.122295 | 2.388 | 0.0240 |
| $H_6$ | HN9 | 0.128512 | 2.388 | 0.0240 | $H_6$ | HN9 | 0.122295 | 2.388 | 0.0240 |
| $H_7$ | HN9 | 0.128512 | 2.388 | 0.0240 | $H_7$ | HN9 | 0.122295 | 2.388 | 0.0240 |
| $C_8$ | CN7B | -0.054614 | 4.054 | 0.0200 | $C_8$ | CN7B | -0.105793 | 4.054 | 0.0200 |
| $H_8$ | HN7 | 0.078235 | 2.352 | 0.0220 | $H_8$ | HN7 | 0.086753 | 2.352 | 0.0220 |
| $H_9$ | HN7 | 0.078235 | 2.352 | 0.0220 | $H_9$ | HN7 | 0.086753 | 2.352 | 0.0220 |
| $C_9$ | CT2 | 0.088421 | 3.875 | 0.0550 | $C_9$ | CT2 | 0.146788 | 3.875 | 0.0550 |
| $H_{10}$ | HA | 0.007750 | 2.352 | 0.0220 | $H_{10}$ | HA | -0.005416 | 2.352 | 0.0220 |
| $H_{11}$ | HA | 0.007750 | 2.352 | 0.0220 | $H_{11}$ | HA | -0.005416 | 2.352 | 0.0220 |
| $C_{10}$ | CT2 | 0.091582 | 3.875 | 0.0550 | $C_{10}$ | CT2 | 0.071775 | 3.875 | 0.0550 |
| $H_{12}$ | HA | -0.020370 | 2.352 | 0.0220 | $H_{12}$ | HA | -0.020200 | 2.352 | 0.0220 |
| $H_{13}$ | HA | -0.020370 | 2.352 | 0.0220 | $H_{13}$ | HA | -0.020200 | 2.352 | 0.0220 |
| $C_{11}$ | CT2 | -0.100377 | 3.875 | 0.0550 | $C_{11}$ | CT2 | -0.066054 | 3.875 | 0.0550 |
| $H_{14}$ | HA | 0.017596 | 2.352 | 0.0220 | $H_{14}$ | HA | 0.014064 | 2.352 | 0.0220 |
| $H_{15}$ | HA | 0.017596 | 2.352 | 0.0220 | $H_{15}$ | HA | 0.014064 | 2.352 | 0.0220 |
| $C_{12}$ | CT2 | 0.172569 | 3.875 | 0.0550 | $C_{12}$ | CT2 | 0.014905 | 3.875 | 0.0550 |
| $H_{16}$ | HA | -0.027922 | 2.352 | 0.0220 | $H_{16}$ | HA | 0.005025 | 2.352 | 0.0220 |
| $H_{17}$ | HA | -0.027922 | 2.352 | 0.0220 | $H_{17}$ | HA | 0.005025 | 2.352 | 0.0220 |
| $C_{13}$ | CT3 | -0.170259 | 3.875 | 0.0550 | $C_{13}$ | CT2 | 0.029233 | 3.875 | 0.0550 |
| $H_{18}$ | HA | -0.044253 | 2.352 | 0.0220 | $H_{18}$ | HA | -0.010404 | 2.352 | 0.0220 |
| $H_{19}$ | HA | -0.044253 | 2.352 | 0.0220 | $H_{19}$ | HA | -0.010404 | 2.352 | 0.0220 |
| $H_{20}$ | HA | -0.044253 | 2.352 | 0.0220 | $C_{14}$ | CT2 | 0.090529 | 3.875 | 0.0550 |
| | | | | | $H_{20}$ | HA | -0.011092 | 2.352 | 0.0220 |
| | | | | | $H_{21}$ | HA | -0.011092 | 2.352 | 0.0220 |
| | | | | | $C_{15}$ | CT3 | -0.162384 | 3.875 | 0.0550 |
| | | | | | $H_{22}$ | HA | 0.040774 | 2.352 | 0.0220 |
| | | | | | $H_{23}$ | HA | 0.040774 | 2.352 | 0.0220 |
| | | | | | $H_{24}$ | HA | 0.040774 | 2.352 | 0.0220 |

AMINOPYRIDINIUM IONIC LIQUIDS

CROSS-REFERENCE TO RELATED APPLICATIONS

This application claims priority to U.S. Provisional Application No. 60/620,421, entitled "Aminopyridinium Ionic Liquids for High Temperature Applications," filed Oct. 21, 2004, and U.S. Provisional Application No. 60/620,420, filed Oct. 21, 2004, entitled "Aminopyridinium Ionic Liquids", filed Oct. 21, 2004. The entire disclosure and contents of these applications is hereby specifically incorporated herein by reference.

STATEMENT OF JOINT RESEARCH AGREEMENT

In compliance with 37 C.F.R. §1.71(g) (1), disclosure is herein made that the inventions described and claimed herein were made pursuant to a Joint Research Agreement as defined in 35 U.S.C. 103 (c) (3), that was in effect on or before the date the inventions were made, and as a result of activities undertaken within the scope of the Joint Research Agreement, by or on the behalf of the University of Notre Dame du Lac and Reilly Industries.

BACKGROUND

1. Field of the Invention

The present invention relates generally to the field of ionic compounds, as a novel class of pyridinium-based cations (aminopyridinium and piperidino-pyridinium cations) and ionic compounds containing the pyridinium-based cations are provided. The invention also relates to the field of improved heat transfer preparations, solvents, lubricants, and compositions containing them, suitable for use in high temperature applications.

2. Related Art

Ionic liquids (ILs) are organic salts with low melting points. Many of these compounds are liquid at room temperature in their pure state. These ILs act much like good organic solvents, dissolving both polar and nonpolar species.[2] They have also been reported to perform better than at least some commonly used solvents.[3]

Ionic liquids have also been defined as molten salts, having a melting point below 100° C.[4] By way of example, ILs include the quaternary imidazolium salts, compounds having quaternary aromatic 5- and 6-membered ring heterocycles such as imidazolium salts, pyridinium salts, and the like.[5]

Ionic liquids (ILs), while being liquid in their pure state at room temperature, have negligible vapor pressure.[1] Because they have negligible vapor pressure, this class of substances would not contribute to air pollution, and would not contribute to the generation of potentially toxic and/or harmful emissions when used as a solvent, etc., in industrial and commercial applications. Thus, they present an advantage over other types of liquids, particularly solvents that do generate fugitive emissions. This characteristic has made ILs an attractive alternative as a solvent for commercial manufacturing processes.

Conventional solvents and heat transfer fluids have boiling points at or below 320° C., and are therefore not useful at temperatures at or exceeding this temperature. The flash point and fire point of many conventional heat transfer fluids are generally much lower than 320° C. In contrast, ionic liquids do not evaporate, and therefore the flash point of these compounds is essentially the same temperature as their decomposition temperatures.

For these reasons, among others, ionic liquids are being intensively investigated for a variety of applications, including as solvents for reactions and separations, as non-volatile electrolytes, and as heat transfer fluids.

While possessing many characteristics that render these compounds suitable for uses that are efficient and more environmentally compatible (such as in chemical processing), they have not found widespread use. A need continues to exist in the art for a class of ionic liquids having a wider range of temperature stability, particularly a wider upper range of temperature stability, without sacrificing a functional and extended lower liquids range.

The increasing demands of industry creates a continuing need for ever improved and long-lasting, stable lubricants, solvents and heat transfer fluids capable of withstanding temperatures of 300° C. or higher for extended periods of time, sometimes under highly pressurized conditions. While currently available ionic liquids posses some characteristics that render them interesting for development in these industries, they have not as yet been optimized sufficiently to meet the demands of current day high temperature application needs.

SUMMARY

The above and other long felt needs in the art are met in the present invention.

The present invention, in one aspect, presents a novel class of ionic pyridinium-based compounds, particularly, a novel class of aminopyridinium-based and piperidino pyridinium-based cation species and ionic compounds that contain these cation species. These ionic compounds have many improved properties over other classes of ionic compounds. Among these improved characteristics is a broader liquidus region, or range of temperatures between the normal freezing point and boiling point/decomposition temperature of the liquid form of the ionic compound. In particular embodiments, the liquidus range of the present ionic pyridinium-based compounds is between about −73° C. (−99° F.) to about 447° C. (837° F.).

In one aspect, a pyridinium-based cation is provided. In some embodiments, the pyridinium-based cation is an aminopyridinium cation. In some embodiments, the aminopyridinium cation comprises a structure of Formula I:

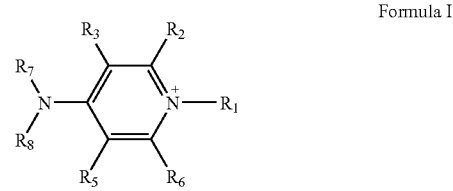

Formula I wherein:
$R_1, R_2, R_3, R_5, R_6, R_7$, or $R_8$ is $C_nH_{2n+1}$, where n is 1 to 16.

In some embodiments, Formula I comprises an $R_1$ through $R_8$ group as depicted in Table 1.

TABLE 1

| $R_1$ | $R_2$ | $R_3$ | $R_5$ | $R_6$ | $R_7$ | $R_8$ |
|---|---|---|---|---|---|---|
| n-$C_4H_9$ | H | H | H | H | $CH_3$ | $CH_3$ |
| n-$C_4H_9$ | H | $CH_3$ | H | H | $CH_3$ | $CH_3$ |
| n-$C_6H_{13}$ | H | H | H | H | $CH_3$ | $CH_3$ |
| n-$C_6H_{13}$ | H | $CH_3$ | H | H | $CH_3$ | $CH_3$ |

In some embodiments, the aminopyridinium cation is a mono-alkyl aminopyridinium or a di-alkyl aminopyridinium cation. In some of these embodiments, the di-alkyl aminopyridinium compound is dimethylaminopyridinium, which is designated interchangeably herein as DMAP or DMApy.

In some embodiments, the aminopyridinium-based cation comprises bDMApy, bmDMApy, hDMApy, or hmDMApy.

In yet other embodiments, the DMAP cation component of the aminopyridinium-based ionic compounds of the invention may comprise a structure depicted in the following Formulas:

Formula III

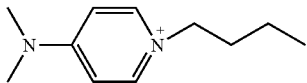

[bDMApy]

Formula IV

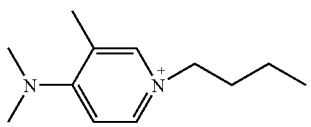

[bmDMApy]

Formula V

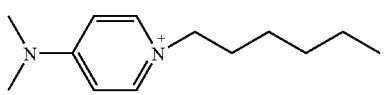

[hDMApy]

Formula VI

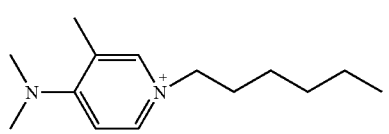

[hmDMApy]

In another aspect, an aminopyridinium ionic compound is provided comprising an aminopyridinium cation and an anion. In some embodiments, the aminopyridinium ionic compound may be described as comprising a structure of Formula X:

Formula X

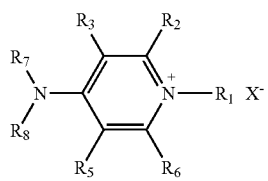

wherein:
$R_1, R_2, R_3, R_5, R_6, R_7$ or $R_8$ is $C_nH_{2n+1}$, where n is 1 to 16; and
X is an anion.

In yet other embodiments, $R_1, R_2, R_3, R_5, R_6, R_7, R_8$ or any combination thereof, is H, alkyl, an electron donating group, such as an amine, a hydroxide, an ether, phenyl, sulfide, or an amide; an electron withdrawing group, such as a halogen (fluoride, chloride, bromide, etc), nitrate, sulfate, ester, a carboxylic acid, a nitrile, an alkyl halide, a ketone, ammonium, an aldehyde, a borate, or any combination thereof.

In yet another aspect, a pyridinium-based cation comprising a piperidino-pyridinium cation is provided. In some embodiments, the piperidino-pyridinium cation comprises a structure of Formula II:

Formula II

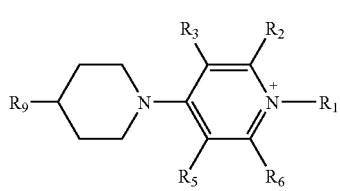

wherein:
$R_1, R_2, R_3, R_5, R_6,$ and $R_9$ are $C_nH_{2n+1}$, wherein n is 1 to 16.

In some embodiments, the cation of Formula II comprises the $R_1, R_2, R_3, R_5,$ and $R_6$ groups identified in Table 2:

TABLE 2

| $R_1$ | $R_2$ | $R_3$ | $R_5$ | $R_6$ |
|---|---|---|---|---|
| n-$C_6H_{13}$ | H | H | H | H |

In some embodiments, the piperidino pyridinium cation is [h(mPip)py], as shown in Formula VII.

Formula VII

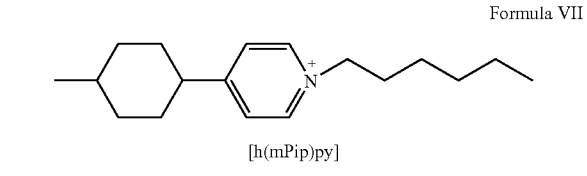

[h(mPip)py]

In yet another aspect, a piperidino pyridinium-based ionic compound is provided. In some of these embodiments, the piperidino pyridinium ionic compound may be described as comprising an anion and a piperidino pyridinium cation. In some embodiments, the ionic piperidino pyridinium compound comprises a structure of Formula XI:

Formula XI

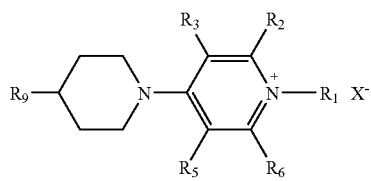

wherein:
$R_1, R_2, R_3, R_5, R_6$ and $R_9$ is $C_nH_{2n+1}$, wherein n is 1 to 16; and
X is an anion.

In some embodiments, the anion component, X, of any of the ionic compounds described herein may comprise any suitable anionic species. By way of example, such anion species include any non-Lewis acid anion. By way of example, the anion component of the ionic pyridinium-based compounds may comprise $PF_6$, $BF_4$, $NO_3$, halides, bromide (Br), bis(trifluoromethylsulfonyl)imide ($N(SO_2CF_3)_2$ or $Tf_2N$), bis(methanesulfonyl)imide ($N(SO_2CH_3)_2$), dicyanimide (dca, $N(CN)_2$), alkylsulfate, alkylsulfonates, saccharinate, triflate ($SO_3CF_3$), tosylate, acetate, lactate, tris(perfluoroalkyl)trifluorophosphate, trifluoroacetate, gluconate, ethylsulfate ($EtSO_4$), tetrafluoroborate (BF4), docusate (doc), 2-(2-methoxy-ethoxy)-ethysulfate ($C_5H_{11}O_2SO_4$), methylsulfate ($MeSO_4$), acetate ($CH_3CO_2$), trifluoroacetate ($CF_3CO_2$), a mono- or diperfluorosulfonate, or any one of $(CF_3)_2PF_4$, $(CF_3)_3PF_3$, $(CF_3)_4PF_2$, $(CF_3)_5PF$, $(CF_3)_6P$, $SF_5CF_2SO_3$, $SF_5CHFCF_2SO_3$, $CF_3CF_2(CF_3)_2CO$, $(CF_3SO_2)_2CH$, $(SF_5)_3C$ or $(O(CF_3)_2C_2(CF_3)_2O)_2PO$.

In some aspects, the pyridinium-based ionic compound comprises a piperidino-based ionic compound. In some of these embodiments, the piperidino pyridinium ionic compound is 1-hexyl-4-(4-methylpiperidino) pyridinium bis (trifluoromethylsulfonyl) imide, having a structure of Formula XII:

Formula XII

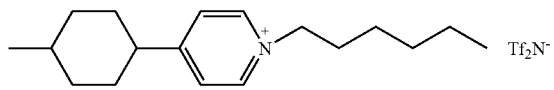

Tf$_2$N$^-$

In specific embodiments, the pyridinium-based ionic compound comprises an aminopyridinium ionic compound. In one such embodiment, the aminopyridinium ionic compound comprises 1-hexyl-4-N,N-dimethylaminopyridinium bis(trifluoromethylsulfonyl)imide, having a structure of Formula XIII.

Formula XIII

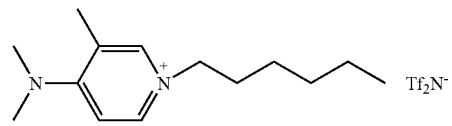

Tf$_2$N$^-$

In yet another specific embodiment, the aminopyridinium ionic compound is a liquid, and comprises hDMAP-Tf$_2$N.

In yet another specific embodiment, the aminopyridinium ionic compound comprises [mDMAP][Tf$_2$N]. In some embodiments, the aminopyridinium ionic compound is a liquid.

According to some aspects, the aminopyridinium ionic compound may be described as having an elevated temperature of decomposition. In some embodiments, these compounds may be further described as having a higher temperature of thermal decomposition onset, a wider range of temperature stability, and a wider liquidus range, compared to non-aminopyridinium-based compounds.

In some embodiments, the aminopyridinium ionic compounds, by way of example, may be further described as having an enhanced and/or expanded upper liquidus range. In some embodiments, this expanded upper liquidus range is defined by a temperature range of about 200° C. (392° F.) or higher, or about 200° C. (392° F.) to about 447° C. (837° F.), or even up to 482° C. (900° F.) or higher. This expanded upper liquidus range renders the aminopyridinium ionic compounds particularly suitable for use in extremely high temperature applications, up to and including applications as a lubricant where the compound is exposed to temperatures of 482° C. (900° F.). Other liquid lubricants, particularly silicon-based lubricants, are not suitable for use at temperatures exceeding about 270° C., as at this temperature, silicon-based compounds begin to decompose or have evaporated away (reached or exceeded their boiling point/flash point).

In some embodiments, the rate of decomposition of the aminopyridinium ionic compounds and the piperidino pyridinium ionic compounds may be described as about 20% to about 50%, or even 100% less rapid, or even 3-fold, 4-fold to 5-fold, less rapid than the rate of decomposition for the corresponding non-amino pyridinium- or piperidino pyridinium-containing composition.

The ionic aminopyridinium compounds may be further characterized in that they have a much longer useful half-life upon exposure to high temperatures, compared to non-aminopyridinium containing compounds. Specifically, the ionic aminopyridinium compounds have been found to be stable and not subject to degradation under temperatures of 300° C., or 320° C., or higher, and for extended periods of time. This temperature stability extrapolated over a defined and studied interval of time and measured heat exposure levels has been used to demonstrate that the aminopyridinium ionic compounds are more stable and resistant to mass loss and degradation, and for a longer period of time, compared to non-aminopyridinium cation containing compounds. Typical non-amino pyridinium-cation containing compounds begin to degrade at significantly lower temperatures (240° C.) and after a much shorter time interval (degradation onset up to three-times sooner) upon temperature/stress exposure, compared to a corresponding aminopyridinium-containing ionic compound (particularly the methylamino pyridinium, dimethylamino pyridinium, and piperidino pyridinium-cation containing ionic compounds).

In some aspects, high temperature lubricants are provided that are stable and resistant to degradation under exposure to high temperatures, alone or in combination with very low pressure conditions and, for extended periods of time.

In some embodiments the aminopyridinium-based compositions may be described as comprising a preserved lower liquid and higher improved upper liquid range of stability. For example, while maintaining an elevated upper temperature of degradation range (i.e, 440 to 480° C.), the compositions also include a preserved and stable liquid lower range (-73° C.). By way of example, the preserved and stable liquid lower range of the aminopyridinium-based compounds may be described as about -73° C. (-99° F.) to about 37° C. (98.6° F.). The pyridinium-based compounds posses a wide window of operable temperatures, and thus may be used in a wider range of industrial and commercial applications. This illustrates yet another advantage of the compounds and compositions containing them in the possession of an improved upper and preserved lower range of operability and stability, and remains liquid over a very broad range of temperatures.

In another aspect, a pyridinium based ionic compound is provided that possesses enhanced thermal stability and an improved liquidus range. The pyridinium-based ionic compounds, in some embodiments, comprise an anion and a pyridinium-based cation component.

In yet another aspect, a method for enhancing thermal stability of an ionic compound is provided. In some embodiments, the method comprises preparing an ionic compound comprising an aminopyridinium cation as described herein and an anion to provide aminopyridinium ionic compound. In some embodiments, the anion is other than chloride. The thermal stability of these aminopyridinium containing ionic compounds may be further described in some embodiments to be 2-fold to 3-fold greater against heat degradation and mass loss (such as upon prolonged exposure to elevated temperatures of 320° C.) as compared to non-aminopyridinium containing compounds. In some embodiments, the aminopyridinium containing ionic compound is a solid or a liquid. In preferred embodiments the aminopyridinium ionic compound is a liquid.

In yet another aspect, a method is provided comprising enhancing the thermal stability of a compound by providing an aminopyridinium or an amino piperidino pyridinium cation as described herein with an anion as described herein to provide an aminopyridinium ionic compound or an amino piperido pyridinium ionic compound, respectfully.

In some embodiments, the anion comprises any of the anionic species as described herein. In particular embodiments, the anion (X) comprises bromide, bis (trifluoromethylsulfonyl) imide ($N(SO_2CF_3)_2$ or $Tf_2N$). In some embodiments, the amino piperidino pyridinium ionic compound is described as having a liquidus range of about −73° C. and about 440° C. In other embodiments, the amino piperidino pyridinium ionic compound is a solid or a liquid. In preferred embodiments, the amino piperidino pyridinium compound is a liquid. In particular embodiments, the amino piperidino pyridinium compound comprises 1-Hexyl-4-(4-methyl piperidino) pyridinium bromide, 1-Hexyl-4-(4-methyl piperidino) pyridinium $Tf_2N$, or a mixture thereof.

Yet another advantage of the pyridinium-based ionic compositions is a preserved viscosity that is suitable for providing a conveniently pumpable fluid preparation. The viscosities of the pyridinium-based ionic compositions are generally higher, compared to conventional organic solvents. The pyridinium-based ionic compounds may be mixed with other liquid and non-liquid components (e.g., diluents, reactions, additives, and other potentially viscosity reducing materials) to adjust the viscosity to a desired level suitable for a particular application of interest (for example See, Chemistry and Technology of Lubricants. Eds. S. T. Orszolik, R. M. Mortier, 1992 which reference is specifically incorporated by reference). In addition, the temperature of the composition may be adjusted to enhance viscosity. Such may be the case where, for example, it is desirable to reduce the viscosity of the liquid. In such case, the temperature of the composition should be increases. Advantageously, pyridinium-based ionic compositions may be further described as having a viscosity that varies as a function of increasing temperature.

The improved combination of features of the pyridinium-based ionic compounds (aminopyridinium and piperidino pyridinium containing) presented herein provide for the formulation of products having much improved performance specifications that may be beneficial in many commercially important industries, including use in heat transfer fluids, solvents, catalysts, lubricants, and many other related products.

In some embodiments, the invention provides a solvent, a lubricant or a heat transfer fluid comprising the aminopyridinium-containing ionic compound, the piperidino pyridinium containing ionic compound, or a mixture thereof. These preparations may be formulated alone or together with diluents, reactions, additives, and other potentially viscosity reducing materials (e.g. antioxidizing agents, antifoaming agents, organic or inorganic compounds) to achieve any desired viscosity, etc., particularly suitable for the desired use.

In some embodiments, a method is provided comprising providing a lubricant or oil having an improved useful life. By way of example, these methods may be used in preparing a lubricant or oil for use in machinery and engines, such as in an engine of an automobile, jet engine, turbine, or other high performance apparatus, or other device that typically operates under constant high temperature and/or low pressure operating conditions. For example, it is anticipated that the aminopyridinium-based ionic compounds may be formulated into a lubricant suitable for use in an automobile to provide an improved and longer half-life lubricating fuel (oil), as well as in highly specialized aeronautical vehicles, including space craft.

Additional industries in which the improved ionic pyridinium-based compounds of the present invention will find application are in the fabrication of batteries (electrolytes), fuel cells (conducting medium), high temperature fuel cells (conducting medium), in gas separations (liquid absorbent), liquid membrane fabrication (separating agent), processing of combustion gases (removal of sulfur compounds, nitrogen oxide compounds, and $CO_2$), etc.

The following abbreviations are used throughout the Specification:
DMAP or DMApy—dimethylaminiumpyridinium;
DOC—Docusate;
LIC—liquid ionic compound;
LLE—Liquid liquid equilibrium;
NMR—Nuclear Magnetic Resonance;
TGA—Thermal gravimetric analysis;
epy—1-ethylpyridinium;
empy—1-ethyl-3-methylpyridinium;
emmpy—1-ethyl-3,5-dimethylpyridinium;
$Et_2Nic$—1-ethyl-nicotinic acid ethyl ester;
bpy—1-butylpyridinium;
bmpy—1-butyl-3-methylpyridinium;
bmmpy—1-butyl-3,5-dimethylpyridinium;
bDMApy—1-butyl-4-(dimethylamino)pyridinium;
bmDMApy—1-butyl-3-methyl-4-(dimethylamino)pyridinium;
$b_2Nic$—1-butyl-nicotinic acid butyl ester;
hpy—1-hexylpyridinium;
hmpy—1-hexyl-3-methylpyridinium;
hmmpy—1-hexyl-3,5-dimethylpyridinium;
hemmpy—1-hexyl-2-ethyl-3,5-dimethylpyridinium;
hpeepy—1-hexyl-2-propyl-3,5-diethylpyridinium;
hDMApy—1-hexyl-4-(dimethylamino) pyridinium;
hmDMApy—1-hexyl-3-methyl-4-(dimethylamino) pyridinium;
h(mPip)py—1-hexyl-4-(4-methylpiperidino) pyridinium;
opy—1-octylpyridinium;
ompy—1-octyl-3-methylpyridinium;
emim—1-ethyl-3-methylimidazolium;
bmim—1-butyl-3-methylimidazolium;
hmim—1-hexyl-3-methylimidazolium;
hmmim—1-hexyl-2,3-dimethylimidazolium;
perfluoro-hmim—1-(3,4,5,6-perfluorohexyl)-3-methylimidazolium;
omim—1-octyl-3-methylimidazolium;
$N_{4444}$—tetrabutylammonium;
ECOENG 500—cocosalky pentaethoxi methylammonium.

BRIEF DESCRIPTION OF THE DRAWINGS

The invention will be described in conjunction with the accompanying drawings, in which:

FIGS. 7A-7B, according to one embodiment of the invention, illustrates (7A) the partial charges and (7B) Lenard-Jones parameters for pyridinium with Tf$_2$N.

DETAILED DESCRIPTION

Figure 1:
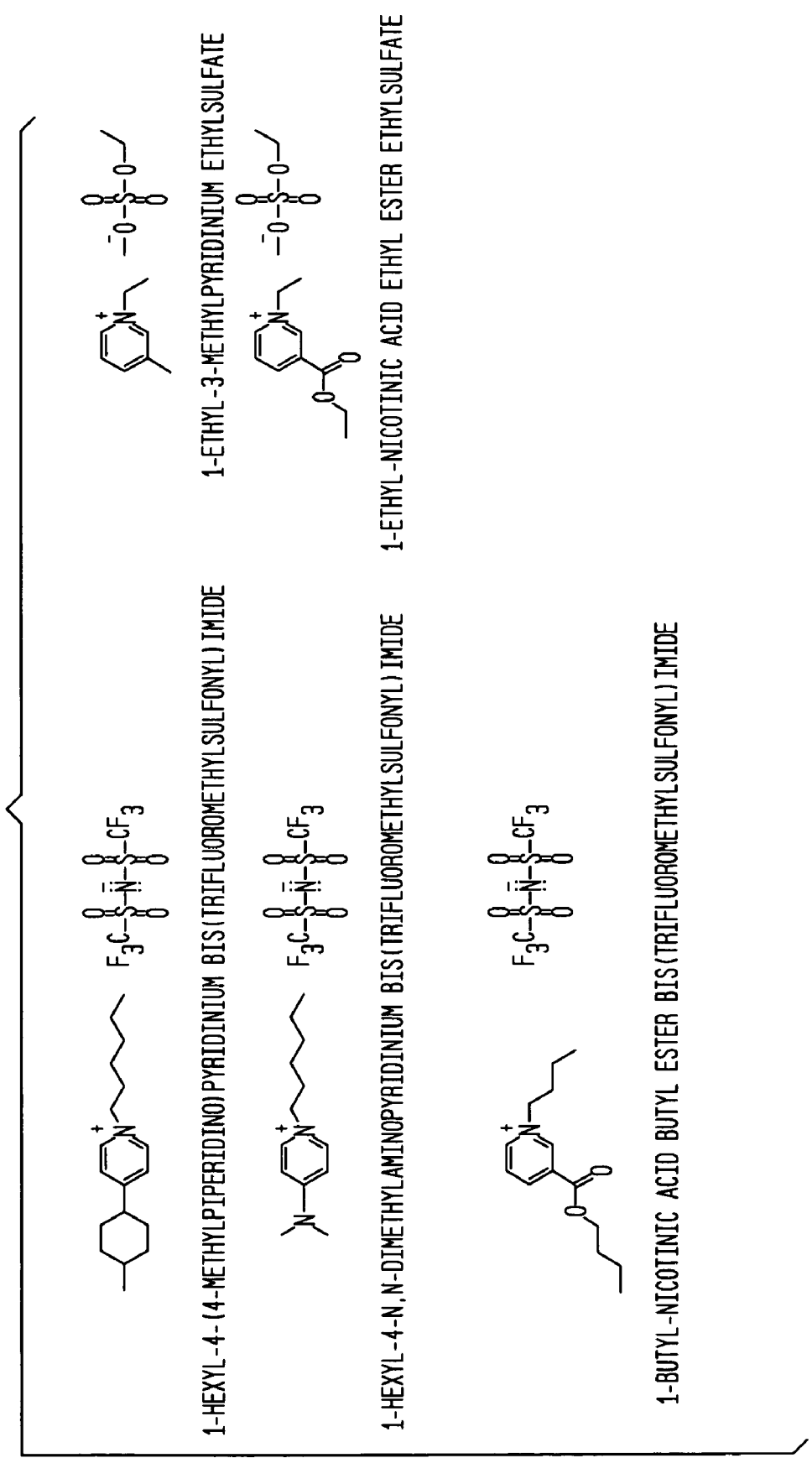
FIG. 1, according to one embodiment of the invention, provides a comparative illustration of the chemical structures of exemplary aminopyridinium compounds, piperidino pyridinium compounds and pyridinium compounds.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

The term "a", "an" and "the" include reference to the plural unless the context as herein resented clearly indicates otherwise.

For purposes of the present invention, the term "cold crystallization temperature" relates to the temperature of the onset of an exothermic peak on heating from a subcooled liquid state to a crystalline solid state.

For purposes of the present invention, the term "decomposition temperature" relates to the temperature at which the substance decomposes into smaller substances or into its constituent atoms.

For purposes of the present invention, the term "heat capacity (abbreviated $C_f$ or just C, also called thermal capacity) is the ability of matter to store heat. The heat capacity of a certain amount of matter is the quantity of heat (measured in joules) required to raise its temperature by one Kelvin (K). The SI unit for heat capacity is J/molK (joule per mole Kelvin).

For the purposes of the present invention, the term "liquidus region" relates to the range of temperature between the normal freezing point and boiling point/decomposition temperature of a compound. The liquidus region will be expressed by reference to degrees Centigrade (° C.). By way of example, water is characterized by a liquidus region of 100° C., at which a compound is stable in a liquid phase.

For purposes of the present invention, the term "high temperature" is a temperature of 200° C. or more.

For the purposes of the present invention, the term "ion" means a non-neutrally charged moiety, such as a cation (positive charge) or an anion (negative charge). Examples of an anion include these include, by way of example, $(CN)_2N$, $CF_3SO_3$, $(CF_3SO_2)_2N$, $BF_4$, $PF_6$, $CH_3C_2$.

For purposes of the present invention, the term "ionic liquid" is defined as an organic salt that is characterized by a low melting point, of about 100° C. or lower for the pure salt.

For purposes of the present invention, the term "melting point" relates to the onset of an endothermic peak on heating.

For the purposes of the present invention, the term "purification" relates to a state of a compound as essentially free of one or more impurities, or may include a composition that has been enriched for a desired compound.

For the purposes of the present invention, the term "$T_{onset}$ (° C.)" relates to the temperature at which there exists an inflection point in the mass versus temperature curve.

For the purposes of the present invention, the term "$T_{start}$ (° C.)" relates to the temperature at which a single well defined weight loss event is first observed.

For the purposes of the present invention, the term "viscosity" relates to a measure of the resistance of a fluid to deformation under shear stress. It is commonly perceived as "thickness", or resistance to pouring. Viscosity describes a liquids' internal resistance to flow and may be thought of as a measure of fluid friction. A liquid is described as "thin" where it has a low viscosity, while being referred to as "thick" where it has a high viscosity.

For purposes of the present invention, the term "glass transition temperature" is defined as the midpoint of a small heat capacity change on heating from the amorphous glass state to a liquid state.

DESCRIPTION

Examples

Example 1

Synthesis of Pyridinium-Based Ionic Compounds

The present example demonstrates exemplary methods that may be used in the synthesis of the pyridinium-based ionic compounds of the invention.

Materials

The list of materials used for the synthesis of the aminopyridinium ILs, including CAS number, source, grade, and purification method (if any), is as follows: 1-bromobutane (CAS #: 109-65-9, Aldrich≧98.0% redistilled), 1-bromohexane (CAS #: 111-25-1, Reilly 99%, used as received), 3-methyl-4-dimethlyaminopyridine (Reilly 99%, used as received), 4-(4-methylpiperidino)pyridine (Reilly 99%, used as received), sodium dicyanoamide (CAS #: 1934-75-4, Aldrich 96%, used as received), and lithium bis(trifluoromethylsulfonyl)imide (CAS#:90076-65-6, 3M 97%, used as received).

The various chemicals can be purchased from Aldrich®, Sigma® Reilly®, Acros®, Lancaster®, TCI®, and Alfa Aesar®, among other chemical providers.

General Reaction to form Aminopyridinium Halide IL

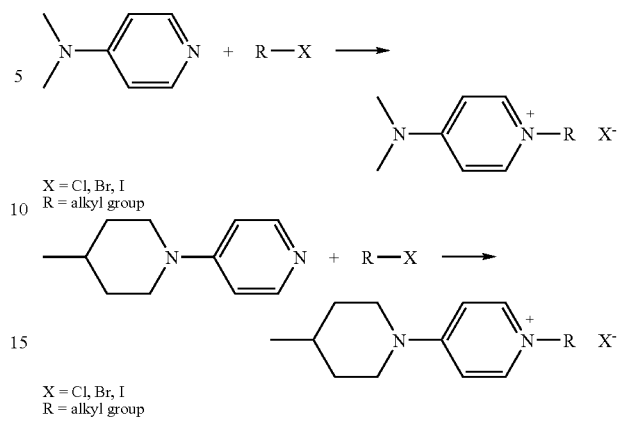

X = Cl, Br, I
R = alkyl group

X = Cl, Br, I
R = alkyl group

General Reaction to Other Aminopyridium ILs

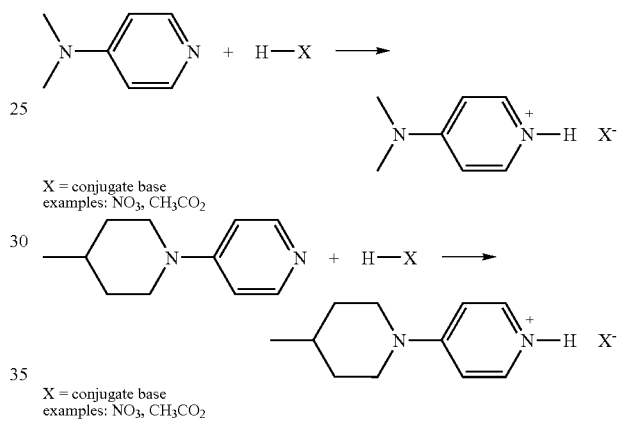

X = conjugate base
examples: $NO_3$, $CH_3CO_2$

X = conjugate base
examples: $NO_3$, $CH_3CO_2$

General Metathesis Reaction

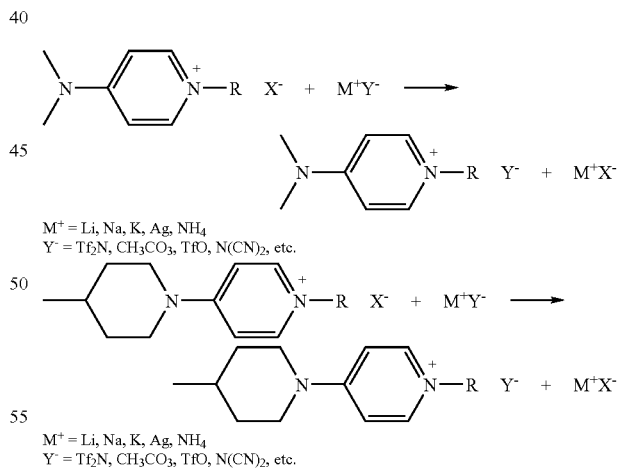

$M^+$ = Li, Na, K, Ag, $NH_4$
$Y^-$ = $Tf_2N$, $CH_3CO_3$, TfO, $N(CN)_2$, etc.

$M^+$ = Li, Na, K, Ag, $NH_4$
$Y^-$ = $Tf_2N$, $CH_3CO_3$, TfO, $N(CN)_2$, etc.

Example 2

Alternative Synthetic Routes

The present example presents one of many alternative chemical route that may be used in synthesizing the compounds of the present invention.

The metathesis reaction can be preformed using an ion exchange column. The alkaline salt of the desired anion in the final ionic liquid can be loaded on to an exchange column.

Substituents on the aminopyridinium ring could be put on after alkylation occurs.

Examples

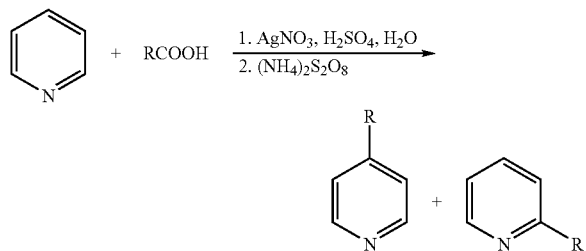

"Alkylation of protonated nitrogen heterocycles (e.g. pyridines, quinolines) can be accomplished by treatment with a carboxylic acid, silver nitrate sulfuric acid, and ammonium peroxydisulfate.[33] R may be primary, secondary, or tertiary."[34,35]

The 1-hexyl-2-methyl-4-diaminopyridinium bromide could be made utilizing the above reaction as follows:

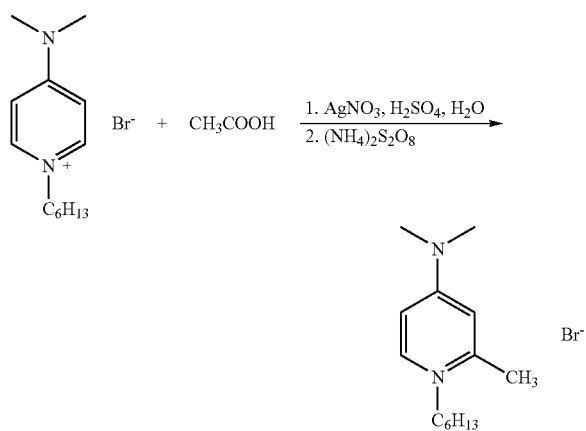

Other leaving groups, such as tosylates, could be used in place of halogens on the primary alkyl groups being added to the nitrogen.

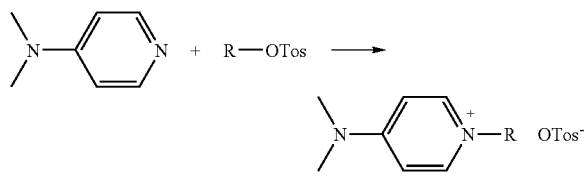

Example 3

Synthesis of Dimethylaminopyridinium Ionic Liquids

The present example demonstrates the synthesis of specific examples of the dimethylaminopyridinium ionic compounds of the present invention. However, many other reagents and modifications to the steps described herein may also be used in accordance with the practice of the present invention.

1-Hexyl-4-dimethylaminopyridium Bromide

In a round bottom flask equipped with a magnetic stir bar, 1 equivalent of 4-dimethyaminopyridine (DMAP) was dissolved in acetonitrile by gentle warming of the mixture. Once the DMAP was completely dissolved, a stoichiometric amount of 1-bromohexane was added to the flask. The reaction flask was then equipped with a condenser and nitrogen atmosphere. The reaction mixture was taken up to 90° C. and allowed to stir 18 hrs. The solution cooled slowly to room temperature. Crystals of 1-hexyl-4-dimethylaminopyridium bromide ([hDMApy][Br]) start to form as the solution cools. The crystals of [hDMApy][Br] were filtered on a Hursh funnel and washed twice with cold acetonitrile. The crude crystals are usually a pale yellow. Recrystallization from acetonitrile yields white crystals of pure [hDMApy][Br] in 65% overall yield. Residual solvent was removed from the ionic liquid under vacuum. Purity of the [hDMApy][Br] was confirmed by NMR spectroscopy. $^1$H NMR ($CDCl_3$): cation: $\delta=0.77$ (t, J=6.6 Hz, $CH_3$), $\delta=1.21$ (m, $CH_2CH_2CH_2$), $\delta=1.80$ (m, J=6.6 Hz, $CH_2$), $\delta=3.02$ (s, 2 $CH_3$), $\delta=4.26$ (t, J=7.5 Hz, $CH_2$), $\delta=7.0$ (dd, $J_1=5.8$ Hz, $J_2=2.0$ Hz, 2CH), $\delta=8.44$ (dd, $J_1=5.7$ Hz, $J_2)=2.0$ Hz, 2CH).

The synthesis of 1-butyl-4-dimethylaminopyridinium bromide would be the same as above, except 1-bromobutane would be used in place of 1-bromohexane. 3-Methyl-4-dimethylaminopyridine can used in place of the 4-dimethylaminopyridine to make the methylated derivatives using the above procedure.

Synthesis of 1-Hexyl-4-dimethylaminopyridium $Tf_2N$

1-Hexyl-4-dimethylaminopyridium $Tf_2N$, [hDMApy][$Tf_2N$] was prepared by a metathesis reaction. In an Erlenmeyer flask equipped with magnetic stir bar, one equivalent of [hDMApy][Br] was dissolved in water. In a second Erlenmeyer flask, 1.3 equivalence of lithium bis(trifluoromethylsulfonyl)imide ($LiNTf_2$) was dissolved in water. The $LiNTf_2$, solution was added to the stiffing solution of [hDMApy][Br]. The reaction stirred for 12 hrs. As the reaction proceeded, two liquid phases formed. The aqueous layer was decanted off of the IL. The IL was then washed repeatedly with water until the wash did not show any signs of precipitation with a solution of 1M $AgNO_3$. The IL was washed two more times before drying on a vacuum line. The crude product was then dissolved in methylene chloride and stirred for 8 hrs with activated charcoal. After the charcoal had been filtered out, the solution was passed through a plug of acidic alumina before removing the methylene chloride under vacuum. Yields for the reaction are quantitative, however small amounts of the IL are lost in the water wash and during purification. Impurity levels of bromide ions in the IL were measured using an Oakton® Ion 510 meter with Cole-Parmer® Ion Specific Probes. Values were less than 10 ppm for bromide. $^1$H NMR ($CDCl_3$): cation: $\delta=0.87$ (t, J=6.6 Hz, $CH_3$), $\delta=1.32$ (m, $CH_2CH_2CH_2$), $\delta=1.85$ (m, J=6.6 Hz, $CH_2$), $\delta=3.26$ (s, 2 $CH_3$), $\delta=4.12$ (t, J=7.5 Hz, $CH_2$), $\delta=6.86$ (dd, $J_1=5.8$ Hz, $J_2=2.0$ Hz, 2CH), $\delta=7.97$ (dd, $J_1=5.7$ Hz, $J_2=2.0$ Hz, 2CH). $^{13}$C NMR ($CDCl_3$): cation: $\delta=14.0$ ($CH_3$), $\delta=22.5$ ($CH_2$), $\delta=25.8$ ($CH_2$), $\delta=31.0$ ($CH_2$), $\delta=31.2$ ($CH_2$), $\delta=40.4$ (2 $CH_3$), $\delta=58.7$ ($CH_2$), $\delta=108.4$ (2 CH), $\delta=141.9$ (2 CH), $\delta=154.0$ (C). $^{13}$C NMR ($CDCl_3$): anion: $\delta=120$ (q, $J_{CF}=320$ Hz, $CF_3$).

Synthesis of 1-Butyl-4-dimethylaminopyridinium Dicyanoamide

The dicyanoamide ILs were made by reacting freshly prepared silver dicyanoamide and the appropriate 4-diaminopyridinium bromide in water. The silver halide was then filtered and the IL dried on a vacuum line. Purity of all ILs was confirmed by $^1$H and $^{13}$C NMR. Impurity levels of halide ions in the ILs synthesized in-house were measured using an Oakton ion 510 meter with Cole-Parmer Ion Specific Probes. All values were less than 10 ppm for halogen.

Example 4

Synthesis of MethylPiperidino Pyridinium Ionic Compounds

The present example demonstrates a method by which the synthesis of the piperidino pyridinium forms of the ionic compounds may be prepared. However, many other reagents and modifications to the steps described herein may also be used in accordance with the practice of the present invention.

Synthesis of 1-Hexyl-4-(4-methylpiperidino)pyridinium Bromide

One equivalent of 1-bromohexane was added to a round bottom flask equipped with a magnetic stir bar. Ethyl acetate was added to the flask to act as the solvent for the reaction. To the stirring mixture, 1 equivalent of 4-(4-methylpiperidino) pyridine was added slowly over 15 min. The flask was fitted with a condenser and heating mantle. The reaction stirred under nitrogen for 4 hours and then heated to 100° C. for 16 hrs. Crystals of 1-hexyl-4-(4-methylpiperidino) pyridinium bromide form as the solution is cooled to room temperature to give 95% yield. The crude solid is filtered and recrystallized from acetonitrile/ethyl acetate. The result is a white, crystalline solid. $^1$H NMR (CDCl$_3$): cation: $\delta$=0.87 (t, J=6.6 Hz, CH$_3$), $\delta$=0.97 (d, J=6.6 Hz, CH$_3$), $\delta$=1.24 (m, 4 CH$_2$), $\delta$=1.87 (m, CH—CH$_3$, 2 CH$_2$), $\delta$=3.17 (t, J=12.3 2 CH), $\delta$=4.18 (d, J=12.3 2 CH), $\delta$=4.28 (t, J=7.5 Hz, CH$_2$), $\delta$=7.17 (d, J=7.6 Hz, 2CH), $\delta$=8.44 (d. J=7.6 Hz, 2CH).

Synthesis of 1-Hexyl-4-(4-methylpiperidino) pyridinium Tf$_2$N

1-Hexyl-4-(4-methylpiperidino)pyridinium Tf$_2$N, [hDMApy][Tf$_2$N] was prepared by a metathesis reaction. In an Erlenmeyer flask equipped with magnetic stir bar, one equivalent of [h(mPip)py][Br] was dissolved in water. In a second Erlenmeyer flask, 1.3 equivalence of lithium bis(trifluoromethylsulfonyl)imide (LiNTf$_2$) was dissolved in water. The LiNTf$_2$ solution was added to the stirring solution of [h(mPip) py][Br]. The reaction stirred for 12 hrs. As the reaction proceeded, two liquid phases formed. The aqueous layer was decanted off of the IL. The IL was then washed repeatedly with water until the wash did not show any signs of precipitation with a solution of 1M AgNO$_3$. The crude product was then dissolved in methylene chloride and stirred for 8 hrs with activated charcoal. After the charcoal had been filtered out, the solution was passed through a plug of acidic alumina before removing the methylene chloride under vacuum. Yields for the reaction are quantitative, however small amounts of the IL are lost in the water wash and during additional purification step to remove any color. Impurity levels of bromide ions in the IL were measured using an Oakton Ion 510 meter with Cole-Parmer Ion Specific Probes. Values were less than 10 ppm for bromide. $^1$H NMR (CDCl$_3$): cation: $\delta$=0.88 (t, J=6.6 Hz, CH$_3$), $\delta$=0.99 (d, J=6.6 Hz, CH3), $\delta$=1.28 (m, 4 CH$^2$), $\delta$=1.85 (m, CH—CH$_3$, 2 CH$_2$), $\delta$=3.16 (t, J=12.3 2 CH). $\delta$=4.10 (t, J=7.5 Hz, CH$_2$), $\delta$=4.11 (d, J=12.3 2 CH), $\delta$=6.96 (d, J=7.8 Hz, 2CH), $\delta$=7.93 (d, J=7.8 Hz, 2CH). $^{13}$C NMR (CDCl$_3$): cation: $\delta$=14.0 (CH$_3$), $\delta$=22.3 (CH$_3$), $\delta$=22.5 (CH$_2$), $\delta$=25.8 (CH$_2$), $\delta$=31.0 (CH$_2$), $\delta$=31.2 (CH$_2$), $\delta$=33.4 (2 CH$_2$), $\delta$=47.3 (2 NCH$_2$), $\delta$=58.2 (NCH$_2$), $\delta$=108.5 (2CH), $\delta$=142.2 (2 NCH), $\delta$=155.3 (C). $^{13}$C MR (CDCl$_3$): anion: $\delta$=120 (q, J$_{CF}$=320 Hz, CF$_3$).

Example 5

Thermal Stability and Other Property Data of Aminopyridinium Ionic Compounds The present example demonstrates the enhanced thermal stability of the aminopyridinium ionic compounds, particularly the aminopyridinium ionic liquids (ILs) prepared according to the present invention.

By way of example, some of the physical property data presented include the glass transition, cold crystallization, melting and freezing temperatures of several of the representative aminopiperidinium compounds of the invention.

TABLE 3

Glass transition ($t_g$), cold crystallization ($t_{cc}$), melting ($t_m$), and freezing ($t_f$) temperatures.

| IL abbreviation | $t_g$/° C. | $t_{cc}$/° C. | $t_m$/° C. | $t_f$/° C. |
|---|---|---|---|---|
| [bDMApy][Br] |  |  | 222 | 160 |
| [hDMApy][Br] |  |  | 195 | 143 |
| [hDMApy][Tf$_2$N] | −69 |  |  |  |
| [hmDMApy][Br] | −2 | 58, 85 | 119 |  |
| [hmDMApy][Tf$_2$N] | −72 | −19 | −2 |  |
| [h(mPip)py][Br] | 33 |  |  |  |
| [h(mPip)py][Tf$_2$N] | −56 | −24 | 37 |  |

TABLE 4

Onset and start temperatures for thermal decomposition.

| IL abbreviation | $t_{onset}$/° C. | $t_{start}$/° C. |
|---|---|---|
| [bDMApy][Br] | 291 | 252 |
| [bmDMApy][Br] | 270 | 225 |
| [bDMApy][dca] | 332 | 278 |
| [hDMApy][Br] | 288 | 252 |
| [hDMApy][Tf$_2$N] | 443 | 376 |
| [hmDMApy][Br] | 275 | 232 |
| [hmDMApy][Tf$_2$N] | 444 | 357 |
| [h(mPip)py][Br] | 284 | 244 |
| [h(mPip)py][Tf$_2$N] | 447 | 367 |

TABLE 5

Heat capacities at 25° C. and 50° C.

| IL abbreviation | $C_p$ at 25° C. (298 K)/J mol$^{-1}$ K$^{-1}$ | $C_p$ at 50° C. (323 K)/J mol$^{-1}$ K$^{-1}$ |
|---|---|---|
| [hDMApy][Tf$_2$N] | 628 | 650 |
| [hmDMApy][Tf$_2$N] | 698 | 749 |

TABLE 6

Heat capacities as a function of temperature over the range of 298-338 K.

| IL abbreviation | Correlation for $C_p$/J mol$^{-1}$ K$^{-1}$ | Standard deviation/J mol$^{-1}$ K$^{-1}$ |
|---|---|---|
| [hDMApy][Tf$_2$N] | 0.729(T/K) + 413.696 | 1.43 |
| [hmDMApy][Tf$_2$N] | 1.838(T/K) + 153.285 | 1.6 |

TABLE 7

Viscosities (cP) as a function of temperature.

| IL abbreviation | t/° C. | | | | | | | | Water Content/ppm |
|---|---|---|---|---|---|---|---|---|---|
| | 10 | 20 | 25 | 30 | 40 | 50 | 60 | 70 | |
| [hDMApy][Tf$_2$N] | 285 | 146 | 111 | 86 | 54 | 36 | 25 | 15 | 68 |
| [hmDMApy][Tf$_2$N] | 278 | 148 | 112 | 87 | 55 | 37 | 26 | 19 | 32.5 |

*Compounds that were solid at room temperature do not have viscosity and heat capacity data.

The data presented in the Tables above demonstrate that the Aminopyridinium based compounds of the present invention posses many improved characteristics, which include an enhanced upper range compound stability (i.e., higher temperature of degradation).

Example 6

Decomposition Data of Selected Ionic Liquids

The present example presents the decomposition data collected with selected Aminopyridinium compounds of the present invention.

TABLE 8

Decomposition data for a selection of ILs under a nitrogen environment at a temperature ramp rate of 2 and 10° C./min.

| | $T_{onset}$ (° C.) | | | $T_{start}$ (° C.) | | |
|---|---|---|---|---|---|---|
| IL | 10° C./min | 2° C./min | Diff. | 10° C./min | 2° C./min | Diff. |
| [hDMApy][Tf$_2$N] | 443 | 414 | 30 | 376 | 317 | 59 |
| [h(mPip)py][Tf$_2$N] | 447 | 414 | 32 | 367 | 331 | 35 |

TABLE 9

Decomposition data for a selection of ILs for nitrogen and air environments at a ramp rate of 10° C./min.

| | $T_{onset}$ (° C.) | | | $T_{start}$ (° C.) | | |
|---|---|---|---|---|---|---|
| IL | Nitrogen | Air | Diff. | Nitrogen | Air | Diff. |
| [hDMApy][Tf$_2$N] | 443 | 432 | 12 | 376 | 333 | 43 |
| [h(mPip)py][Tf$_2$N] | 447 | 434 | 13 | 367 | 347 | 19 |

TABLE 10

Decomposition data for a selection of ILs for nitrogen and air environments at a ramp rate of 2° C./min.

| | $T_{onset}$ (° C.) | | | $T_{start}$ (° C.) | | |
|---|---|---|---|---|---|---|
| IL | Nitrogen | Air | Diff. | Nitrogen | Air | Diff. |
| [hDMApy][Tf$_2$N] | 414 | 393 | 20 | 317 | 293 | 24 |
| [h(mPip)py][Tf$_2$N] | 414 | 384 | 30 | 331 | 316 | 16 |

TABLE 11

Mass loss per hour at elevated temperatures for a selection of ILs under a nitrogen environment.

| | $T_{start}$ | $m_{lost}$ (%/hr) | | | | |
|---|---|---|---|---|---|---|
| IL | (° C.) | 240° C. | 260° C. | 280° C. | 300° C. | 320° C. |
| [bmim][Tf$_2$N] | 344 | 0.15 | 0.57 | 1.34 | 2.50 | 6.66 |
| [hmim][Tf$_2$N] | 347 | 0.09 | 0.26 | 1.07 | 2.28 | 4.21 |
| [hmmim][Tf$_2$N] | 360 | 0.08 | 0.27 | 0.83 | 2.06 | 3.67 |
| [bmpy][Tf$_2$N] | 317 | 0.09 | 0.25 | 0.75 | 2.27 | 4.61 |
| [hpy][Tf$_2$N] | 332 | 0.03 | 0.13 | 0.58 | 1.77 | 4.80 |
| [hmpy][Tf$_2$N] | 330 | 0.07 | 0.24 | 0.73 | 2.02 | 4.61 |
| [hmmpy][Tf$_2$N] | 340 | 0.02 | 0.28 | 1.16 | 2.19 | 4.97 |
| [hDMApy][Tf$_2$N] | 376 | 0.02 | 0.07 | 0.17 | 0.45 | 1.28 |
| [h(mPip)py][Tf$_2$N] | 367 | 0.07 | 0.09 | 0.16 | 0.68 | 1.79 |
| [N$_{6444}$][Tf$_2$N] | 303 | 0.36 | 0.62 | 1.91 | 4.90 | 12.00 |
| [N$_{4441}$][Tf$_2$N] | 322 | 0.10 | 0.28 | 0.94 | 3.44 | 6.64 |
| [Choline][Tf$_2$N] | 344 | 0.04 | 0.10 | 0.53 | 1.88 | 3.99 |

TABLE 12

Apparent first order rate constant, k, for a selection of ILs between 240 to 320° C. under a nitrogen environment.

| | k (s$^{-1}$) | | | | |
|---|---|---|---|---|---|
| IL | 240° C. | 260° C. | 280° C. | 300° C. | 320° C. |
| [bmim][Tf$_2$N] | 4.32E−07 | 1.75E−06 | 4.55E−06 | 9.03E−06 | 3.07E−05 |
| [hmim][Tf$_2$N] | 2.64E−07 | 6.96E−07 | 3.37E−06 | 9.09E−06 | 1.90E−05 |
| [hmmim][Tf$_2$N] | 2.40E−07 | 8.05E−07 | 2.64E−06 | 7.19E−06 | 1.64E−05 |
| [bmpy][Tf$_2$N] | 2.26E−07 | 7.33E−07 | 2.09E−06 | 7.85E−06 | 2.24E−05 |
| [hpy][Tf$_2$N] | 5.76E−08 | 3.19E−07 | 1.77E−06 | 6.10E−06 | 2.47E−05 |
| [hmpy][Tf$_2$N] | 1.86E−07 | 7.42E−07 | 2.29E−06 | 6.85E−06 | 2.20E−05 |
| [hmmpy][Tf$_2$N] | 3.90E−08 | 8.75E−07 | 4.00E−06 | 7.45E−06 | 2.60E−05 |
| [hDMApy][Tf$_2$N] | 5.62E−08 | 2.11E−07 | 4.96E−07 | 1.28E−06 | 4.00E−06 |
| [h(mPip)py][Tf$_2$N] | 1.97E−07 | 2.75E−07 | 4.45E−07 | 1.86E−06 | 5.79E−06 |
| [N$_{6444}$][Tf$_2$N] | 1.04E−06 | 1.69E−06 | 6.11E−06 | 2.61E−05 | 1.35E−04 |
| [N$_{4441}$][Tf$_2$N] | 2.85E−07 | 8.13E−07 | 2.93E−06 | 1.42E−05 | 5.79E−05 |
| [Choline][Tf$_2$N] | 1.17E−07 | 2.96E−07 | 1.58E−06 | 6.42E−06 | 1.63E−05 |

TABLE 13

Time comparison for 10% decomposition of various ILs 320° C. under a nitrogen environment.

| | 320° C. | | |
|---|---|---|---|
| IL | sec | min | hours |
| [bmim][Tf$_2$N] | 3430 | 57.2 | 0.953 |
| [hmim][Tf$_2$N] | 5550 | 92.4 | 1.54 |
| [hmmim][Tf$_2$N] | 6420 | 107 | 1.78 |
| [bmpy][Tf$_2$N] | 4270 | 35.3 | 0.588 |
| [hpy][Tf$_2$N] | 4265 | 71.1 | 1.18 |
| [hmpy][Tf$_2$N] | 4790 | 79.8 | 1.33 |
| [hmmpy][Tf$_2$N] | 4050 | 67.5 | 1.13 |
| [hDMApy][Tf$_2$N] | 26300 | 439 | 7.32 |
| [h(mPip)py][Tf$_2$N | 18200 | 303 | 5.05 |
| [N$_{6444}$][Tf$_2$N] | 780 | 13.0 | 0.216 |

TABLE 14

Half-life of various ILs at 320° C. under a nitrogen environment.

| | 320° C. | | |
|---|---|---|---|
| IL | sec | min | hours |
| [bmim][Tf$_2$N] | 22578 | 376 | 6.27 |
| [hmim][Tf$_2$N] | 36481 | 608 | 10.13 |
| [hmmim][Tf$_2$N] | 42265 | 704 | 11.74 |
| [bmpy][Tf$_2$N] | 30944 | 516 | 8.60 |
| [hpy][Tf$_2$N] | 28063 | 468 | 7.80 |
| [hmpy][Tf$_2$N] | 31507 | 525 | 8.75 |
| [hmmpy][Tf$_2$N] | 26660 | 444 | 7.41 |
| [hDMApy][Tf$_2$N] | 173287 | 2888 | 48.14 |
| [h(mPip)py][Tf$_2$N] | 119715 | 1995 | 33.25 |
| [N$_{6444}$][Tf$_2$N] | 5134 | 86 | 1.43 |

From these data, the mass loss for a sample of [hmim][Tf$_2$N] will decompose 4.75 times faster than a sample of [hDMApy][Tf$_2$N] in an atmosphere of nitrogen. For example, it would take a 100 g sample of [hmim][Tf$_2$N] just a little over 1.5 hours to decompose by 10% and approximately 10 hours to degrade by 50%. It would take a 100 g sample of [hDMApy][Tf$_2$N] just over 7.5 hours and about 48 hours to degrade by the same amounts under the same conditions.

From these data, the mass loss for a sample of [hmim][Tf$_2$N] will decompose 3.28 times faster than a sample of [h(mPip)py][Tf$_2$N] in an atmosphere of nitrogen. For example, it would take a 100 g sample of [hmim][Tf$_2$N] just a little over 1.5 hours to decompose by 10%. It would take a 100 g sample of [h(mPip)py][Tf$_2$N] just over 5 hours to degrade by the same amount.

TABLE 15

Mass loss per hour at elevated temperatures for a selection of ILs under an air environment.

| | T$_{start}$ | m$_{lost}$ (%/hr) | | | | |
|---|---|---|---|---|---|---|
| IL | (° C.) | 240° C. | 260° C. | 280° C. | 300° C. | 320° C. |
| [hmim][Tf$_2$N] | 328 | 0.40 | 1.06 | 2.13 | 3.99 | 9.24 |
| [hmpy][Tf$_2$N] | 308 | 0.42 | 0.97 | 1.68 | 4.59 | 11.17 |
| [hDMApy][Tf$_2$N] | 333 | 0.15 | 0.30 | 0.66 | 1.48 | 4.01 |
| [Choline][Tf$_2$N] | 347 | 0.04 | 0.27 | 1.94 | 5.00 | 9.64 |

TABLE 16

Apparent first order rate constant, k, for a selection of ILs between 240 to 320° C. under an air environment

| | k (s$^{-1}$) | | | | |
|---|---|---|---|---|---|
| IL | 240° C. | 260° C. | 280° C. | 300° C. | 320° C. |
| [hmim][Tf$_2$N] | 1.17E-06 | 3.19E-06 | 7.18E-06 | 1.67E-05 | 4.26E-05 |
| [hmpy][Tf$_2$N] | 9.49E-07 | 2.56E-06 | 4.91E-06 | 1.80E-05 | 4.52E-05 |
| [hDMApy][Tf$_2$N] | 3.61E-07 | 7.54E-07 | 1.75E-06 | 4.45E-06 | 1.44E-05 |
| [Choline][Tf$_2$N] | 1.11E-07 | 7.70E-07 | 6.78E-06 | 3.00E-05 | 6.36E-05 |

TABLE 17

Time comparison for 10% decomposition of various ILs 320° C. under an air environment.

| | 320° C. | | |
|---|---|---|---|
| IL | sec | min | hour |
| [hmim][Tf$_2$N] | 2473 | 41 | 0.69 |
| [hmpy][Tf$_2$N] | 2331 | 39 | 0.65 |
| [hDMApy][Tf$_2$N] | 7317 | 122 | 2.03 |
| [Choline][Tf$_2$N] | 1657 | 28 | 0.46 |

TABLE 18

Half-life of various ILs at 320° C. under an air environment.

| | 320° C. | | |
|---|---|---|---|
| IL | sec | min | hour |
| [hmim][Tf$_2$N] | 16271 | 271 | 4.52 |
| [hmpy][Tf$_2$N] | 15335 | 256 | 4.26 |
| [hDMApy][Tf$_2$N] | 48135 | 802 | 13.37 |
| [Choline][Tf$_2$N] | 10899 | 182 | 3.03 |

The decomposition rates increase in an atmosphere of air. The mass loss for a sample of [hmim][Tf$_2$N] will decompose nearly 3 times faster than a sample of [hDMApy][Tf$_2$N]. For example, it would take a 100 g sample of [hmim][Tf$_2$N] just a little under an hour to decompose by 10% and approximately 4.5 hours to degrade by 50%. It would take a 100 g sample of [hDMApy][Tf$_2$N] just over 2 hours and about 13 hours to degrade by the same amounts under the same conditions.

In this example, an ionic compound that includes an aminopyridinium group cation has a significantly increased durability and longevity of uses under high operational temperatures (320° C.), as evidenced by the 300% and over improvement demonstrated in the measurable half-life of the compound, compared to a non-aminopyridinium cation containing ionic compound. This feature, among others, make the aminopyridinium- and piperidinoamino-based ionic compounds particularly suitable for use in and as heat transfer fluids, and provide a significantly more stable and durable heat transfer fluid compared to commercially available silicone based heat transfer fluids.

Example 7

Measurement and Modeling of Physical Properties

The present example is provided to demonstrate the specific physical properties associated with the aminopyridinium based ionic compounds of the present invention.

In the present example, the following characterizing studies were performed:
1.) measurements of the solubility of carbon dioxide in 1-butyl-nicotinic acid butyl ester bis(trifluoromethylsulfonyl) imide;
2.) measurements of the liquid-liquid equilibrium of 1-butyl-3-methylpyridinium tetrafluoroborate with 1-propanol;
3.) measurements of the densities of pyridinium ILs;
4.) measurements of viscosities of pyridinium ILs;
5.) measurements of the decomposition temperatures of pyridinium ILs;
6.) measurements of the melting point/glass transition temperatures; and
7.) modeling of liquid/liquid equilibria of IL/alcohol mixtures. The heat capacities, measurements of the melting points of mixed pyridinium bromide salts, and spectroscopic measures of solvent strength, are previously reported.

1. Carbon Dioxide Solubility

Figure 2:
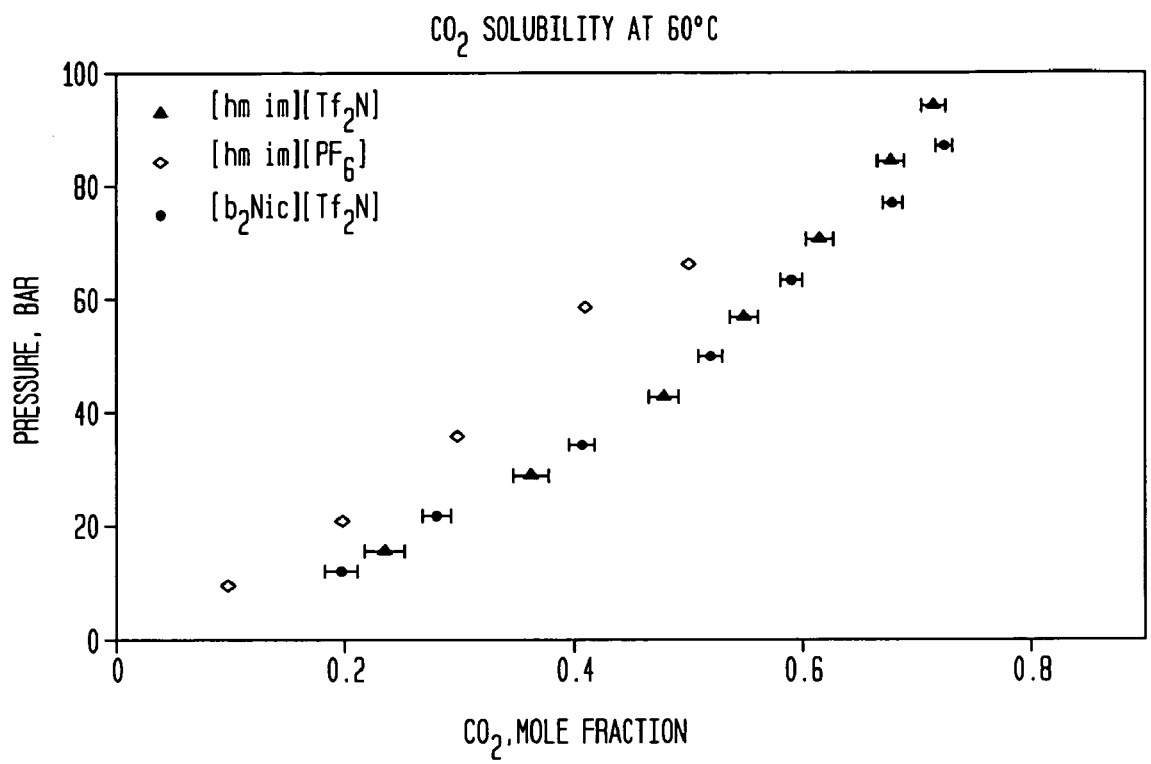
FIG. 2, according to one embodiment of the invention, demonstrates carbon dioxide solubilities at 60° C. for [hmim][$Tf_2N$] (▲), [hmim][$PF_6$] (♦), and [$b_2Nic$][$Tf_2N$] (◘).

The high pressure $CO_2$ solubility was examined for 1-butyl-nicotinic acid butyl ester bis (trifluoromethylsulfonyl) imide, $[b_2Nic]$ $[Tf_2N]$, as ester functionality is known to be $CO_2$-philic. Previously the low pressure measurements have shown that pyridinium ILs have equally good $CO_2$ solubility compared to the equivalent imidazolium version. FIG. 2 shows that the $CO_2$ solubility in $[b_2Nic]$ $[Tf_2N]$ is very similar to that in $[hmim]$ $[Tf_2N]$. It was previously observed that the $[Tf_2N]$ anion is $CO_2$-philic. While not intending to be limited to any particular theory or mechanism of action, it may be that this is the dominant factor in the $CO_2$ solubility in $[b_2Nic]$ $[Tf_2N]$.

2. Liquid-liquid Equilibrium with 1-propanol

Figure 3:
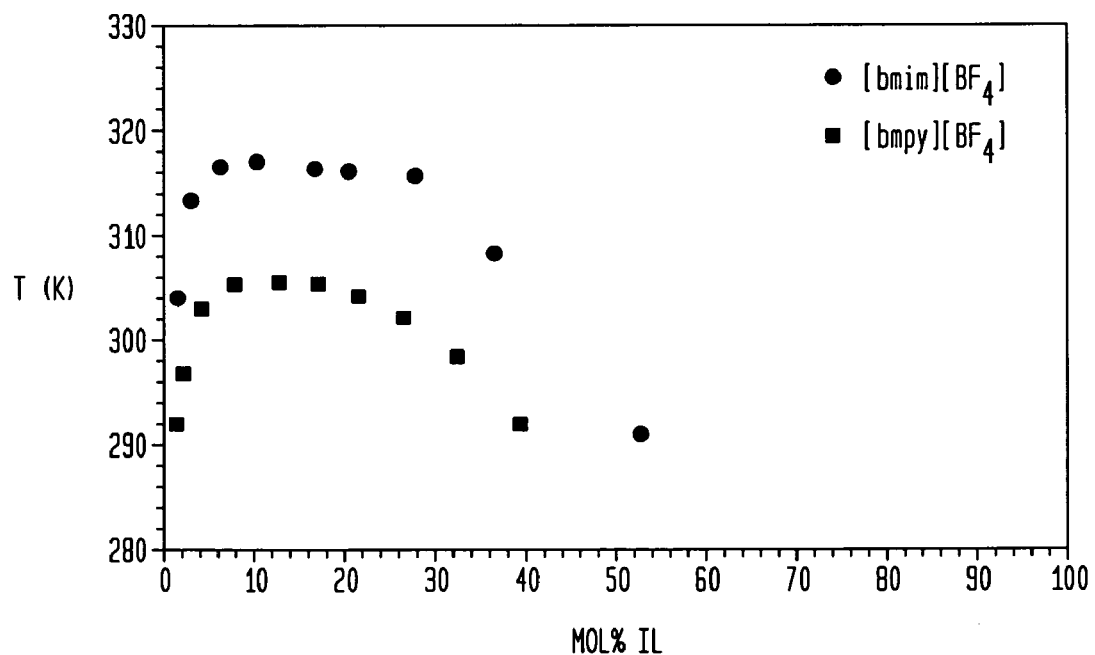
FIG. 3, according to one embodiment of the invention, demonstrates LLE for the system [bmpy][$BF_4$] (■) and 1-propanol with comparison to [bmim][$BF_4$] (●) and 1-propanol.

The liquid-liquid equilibrium observed with 1-propanol for [bmim] [BF4] and [bmpy] [BF4] gave surprising results. In previous studies with the bis (trifluoromethylsulfonyl) imide anion derivatives, the upper-critical solution temperature was higher for pyridinium-based ILs compared with imidizolium-based ILs. The reverse trend is seen when the counter anion is tetrafluoroborate (FIG. 3).

3. Densities

Figure 4:
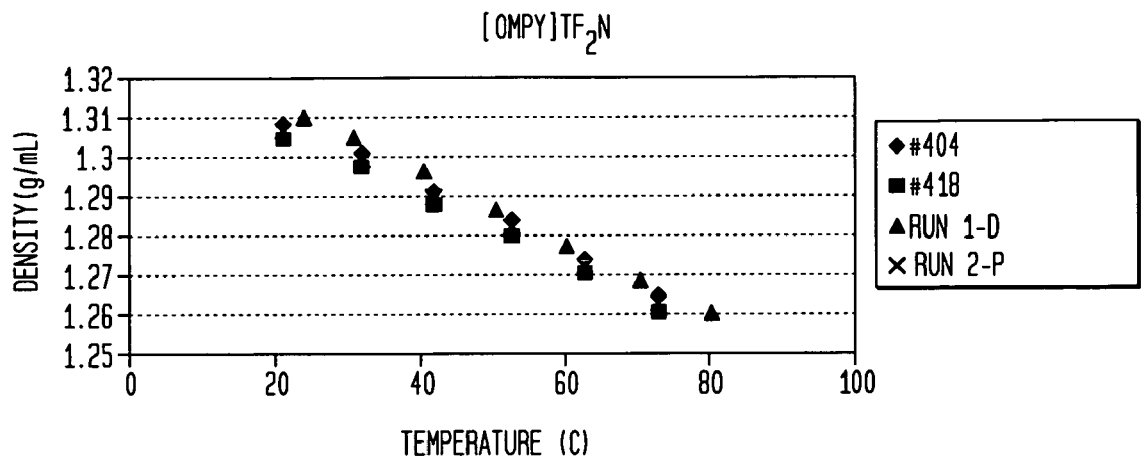
FIG. 4, according to one embodiment of the invention, presents density measurements for 1-octyl-3-methylpyridinium bis(trifluoromethysulfonyl) imide. (#404=(♦); #418= (■)).

The reproducibility of the densities measured is demonstrated in the present example. FIG. 4 shows a graph of individual trials for 1-octyl-3-methylpyridinium bis (trifluoromethysulfonyl) imide as compared with the average and previously measured density at various temperatures.

Figure 5:
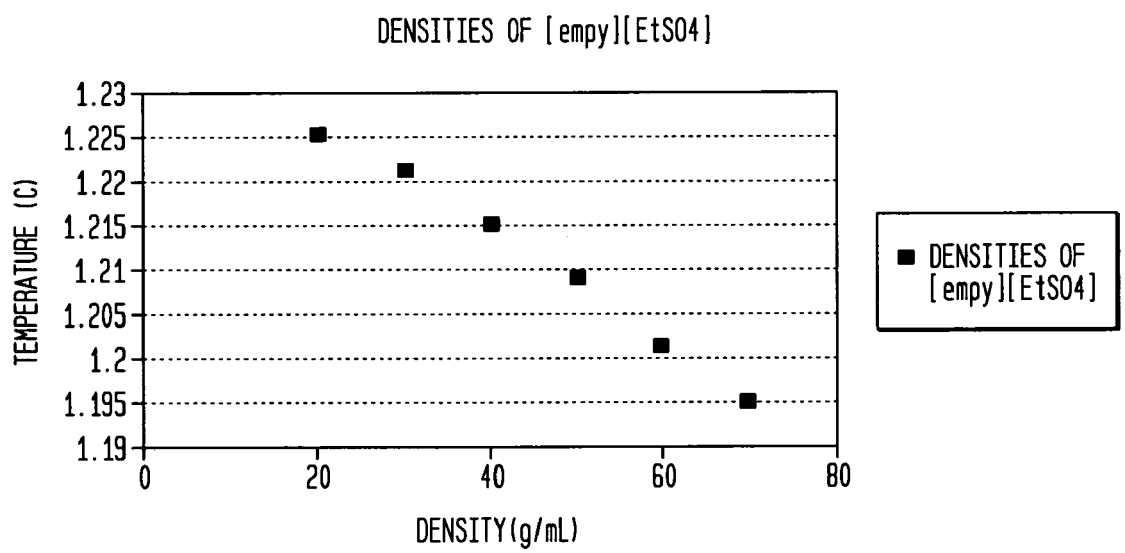
FIG. 5, according to one embodiment of the invention, presents density of [empy][$EtSO_4$] as a function of temperature.

The density as a function of temperature for 1-ethyl-3-methylpyridinium ethylsulfate has been reported. The results are given in Table 19 and shown in FIG. 5.

TABLE 19

Density measurements of 1-ethyl-3-methylpyridinium ethylsulfate as a function of temperature.

| Temperature (° C.) | Density (g/mL) |
|---|---|
| 20.0 | 1.2254 |
| 30.0 | 1.2215 |
| 40.0 | 1.2153 |
| 50.0 | 1.2094 |
| 59.6 | 1.2015 |
| 69.8 | 1.1952 |

4. Viscosities

The viscosity of several pyridinium-based ILs that were synthesized was measured as a function of temperature. The results are shown in Table 20. Results for an imidazolium salt are also shown for comparison. Overall, it appears that the pyridinium salts are somewhat more viscous than the imidazoliums.

TABLE 20

Viscosities of ionic liquids in centipoises.

| IL | 10° C. | 20° C. | 25° C. | 30° C. | 40° C. | 50° C. | 60° C. | 70° C. |
|---|---|---|---|---|---|---|---|---|
| [emim][Tf$_2$N] | 62.3 | 36 | 32.4 | 25.8 | 19.2 | 14.6 | 11.5 | 9.3 |
| [hmpy][Tf$_2$N] | 139.5 | 84.5 | 71.3 | 54.4 | 36.4 | 25.2 | 18.2 | 13.6 |
| [hmmpy][Tf$_2$N] | 261.5 | 141.6 | 109.5 | 83.0 | 52.6 | 35.4 | 25.1 | 18.6 |
| [ompy][Tf$_2$N] | 288.3 | 157.9 | 120.5 | 94.6 | 60.3 | 40.3 | 28.6 | 20.9 |
| [hDMAP][Tf$_2$N] | — | 146.2 | 111.1 | 86.4 | 54.7 | 36.3 | 25.4 | — |
| [hpy][Tf$_2$N] | 735.4 | 340.7 | 243.4 | 180.4 | 103.4 | 62.8 | 41.6 | 28.6 |
| [bmpy][Tf$_2$N] | 115.0 | 65.6 | 53.2 | 41.5 | 27.9 | 19.9 | 15.0 | 11.9 |
| [bmpy][BF$_4$] | 489.7 | 239.3 | 177.31 | 134.1 | 80.0 | 50.7 | 34.2 | 24.3 |
| [empy][EtSO$_4$] | 347.7 | 176.1 | 132.2 | 101.3 | 63.4 | 41.7 | 29.3 | 21.7 |
| [Et$_2$Nic][EtSO$_4$] | 21716 | 5679 | 3230 | 1989 | 842.2 | 399.1 | 216.2 | 126.2 |

5. Decomposition Temperatures

The decomposition temperatures of several pyridinium-based ILs were measured by thermogravametric analysis (TGA). The results are shown in Table 21. The Tf$_2$N ILs have the highest thermal stability, with the compounds with the dimethylamino group and the piperidino groups at the 4 position on the ring being the most thermally stable that we have seen.

TABLE 21

Decomposition temperatures of pyridinium ILs

| IL | $T_{onset}$ (° C.) | $T_{start}$ (° C.) |
|---|---|---|
| [eEtNic][EtSO$_4$] | 253 | 185 |
| [opy][Br] | 236 | 187 |
| [hpy][Br] | 238 | 195 |
| [hdmpy][Br] | 239 | 201 |
| [edmpy][EtSO$_4$] | 297 | 209 |
| [epy][EtSO$_4$] | 303 | 210 |
| [empy][EtSO$_4$] | 281 | 213 |
| [hmppy][Br] | 284 | 244 |
| [hDMAP][Br] | 288 | 252 |
| [hpdepy][Tf$_2$N] | 381 | 325 |
| [hedmpy][Tf$_2$N] | 384 | 328 |
| [hdmpy][Tf$_2$N] | 405 | 340 |
| [hmppy][Tf$_2$N] | 447 | 367 |
| [hDMAP][Tf$_2$N] | 443 | 376 |

6. Melting Points and Glass Transition Temperatures

TABLE 22

Melting points and glass transition temperatures.

| IL | mp/Tg |
|---|---|
| [empy][Tf$_2$N] | $T_m = -71.18$ ° C. |
| [hDMAP][Br] | $T_m = 195.44$ ° C. |
| [hmpippy][Tf$_2$N] | $T_m = 36.80$ ° C. |
| [hmpippy][Br] | $T_g = 31.05$ ° C. |
| [Et$_2$Nic][EtSO$_4$] | $T_g = -47.41$ ° C. |

The melting points ($T_m$) and glass transition temperatures ($T_g$) of several pyridinium salts by differential scanning calorimetry (DSC) are presented. The results are listed in Table 22

7. Modeling of Liquid/liquid Equilibria

The present example demonstrates modeling of the liquid/liquid equilibria of ionic liquids with alcohols using the regular non-random two-liquid (NRTL) equation. This model considers the IL as a single component and requires fitting two parameters for each IL/alcohol pair. Using a linear temperature dependence of the parameters provides a very good representation of the data. However, parameters that give the globally optimum fit to the data were sought. A globally optimum parameter estimation will therefore be made.

Molecular Simulations—Development of a forcefield for pyridinium-based ionic liquids was completed. A forcefield for the 1-n-hexyl-3-methylpyridinium (hmPy), 1-n-octyl-3-methylpyridinium (omPy) and 1-n-hexyl-3,5-dimethylpyridinium (hdmPy) cations has been identified. The parameters for this forcefield are listed in Tables S1-S2(a-d.).

TABLE S.1

Partial charges and Lennard-Jones parameters for Pyridiniums with Tf$_2$N.

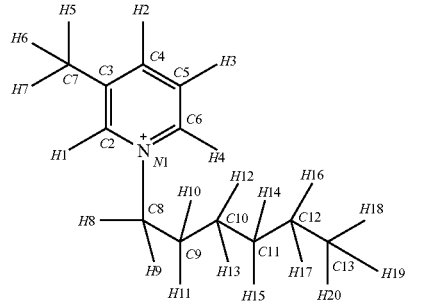

[hmpy+]

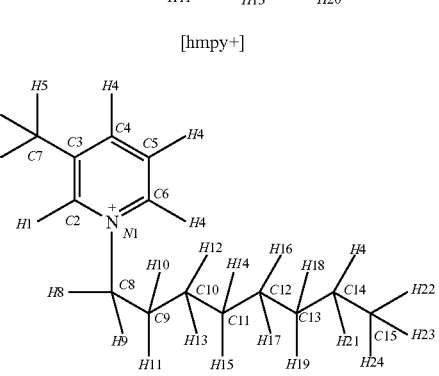

[ompy+]

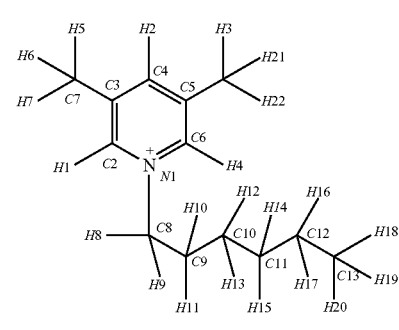

[hdmpy+]

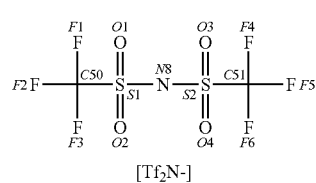

[Tf$_2$N-]

Partial Atomic Charges and Lennard-Jones Parameters

| Atom ID | Type | $q_i$ (e) | $\sigma$(Å) | $\epsilon_i$ (kcal mol$^{-1}$) |
|---|---|---|---|---|
| | | [hmpy+] | | |
| C$_2$ | CN3B | −0.085575 | 3.207/3.688 | 0.1800 |
| C$_3$ | CN3 | 0.188823 | 3.385/3.893 | 0.0900 |
| C$_4$ | CN3A | −0.046264 | 3.207/3.688 | 0.1800 |
| C$_5$ | CN3 | −0.115651 | 3.385/3.893 | 0.0900 |
| C$_6$ | CN3B | 0.042383 | 3.207/3.688 | 0.1800 |
| N$_1$ | NN2 | 0.062369 | 3.296/3.791 | 0.2000 |
| H$_2$ | HN3B | 0.152953 | 1.604/1.844 | 0.0460 |
| H$_1$ | HN3B | 0.179939 | 1.604/1.844 | 0.0460 |
| H$_3$ | HN3B | 0.159195 | 1.604/1.844 | 0.0460 |
| H$_4$ | HN3B | 0.144454 | 1.604/1.844 | 0.0460 |
| C$_7$ | CN9 | −0.338821 | 3.635 | 0.0780 |

TABLE S.1-continued

Partial charges and Lennard-Jones parameters for Pyridiniums with Tf$_2$N.

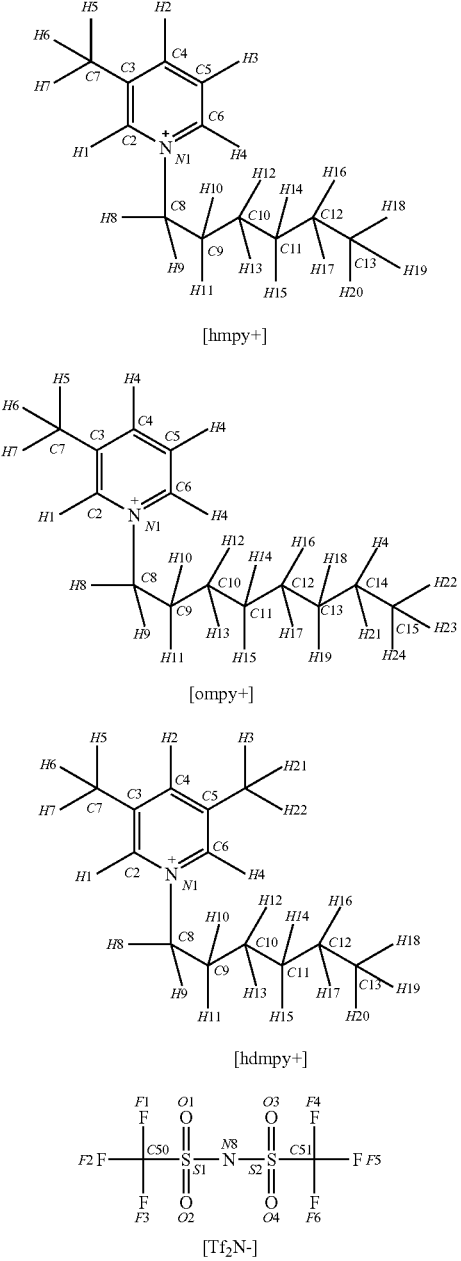

[hmpy+]

[ompy+]

[hdmpy+]

[Tf$_2$N-]

| Partial Atomic Charges and Lennard-Jones Parameters | | | | |
|---|---|---|---|---|
| Atom ID | Type | $q_i$ (e) | σ(Å) | $\epsilon_i$ (kcal mol$^{-1}$) |
| H$_5$ | HN9 | 0.128512 | 2.388 | 0.0240 |
| H$_6$ | HN9 | 0.128512 | 2.388 | 0.0240 |
| H$_7$ | HN9 | 0.128512 | 2.388 | 0.0240 |
| C$_8$ | CN7B | -0.054614 | 4.054 | 0.0200 |
| H$_8$ | HN7 | 0.078235 | 2.352 | 0.0220 |
| H$_9$ | HN7 | 0.078235 | 2.352 | 0.0220 |
| C$_9$ | CT2 | 0.088421 | 3.875 | 0.0550 |
| H$_{10}$ | HA | 0.007750 | 2.352 | 0.0220 |
| H$_{11}$ | HA | 0.007750 | 2.352 | 0.0220 |
| C$_{10}$ | CT2 | 0.091582 | 3.875 | 0.0550 |
| H$_{12}$ | HA | -0.020370 | 2.352 | 0.0220 |
| H$_{13}$ | HA | -0.020370 | 2.352 | 0.0220 |
| C$_{11}$ | CT2 | -0.100377 | 3.875 | 0.0550 |

TABLE S.1-continued

Partial charges and Lennard-Jones parameters for Pyridiniums with Tf$_2$N.

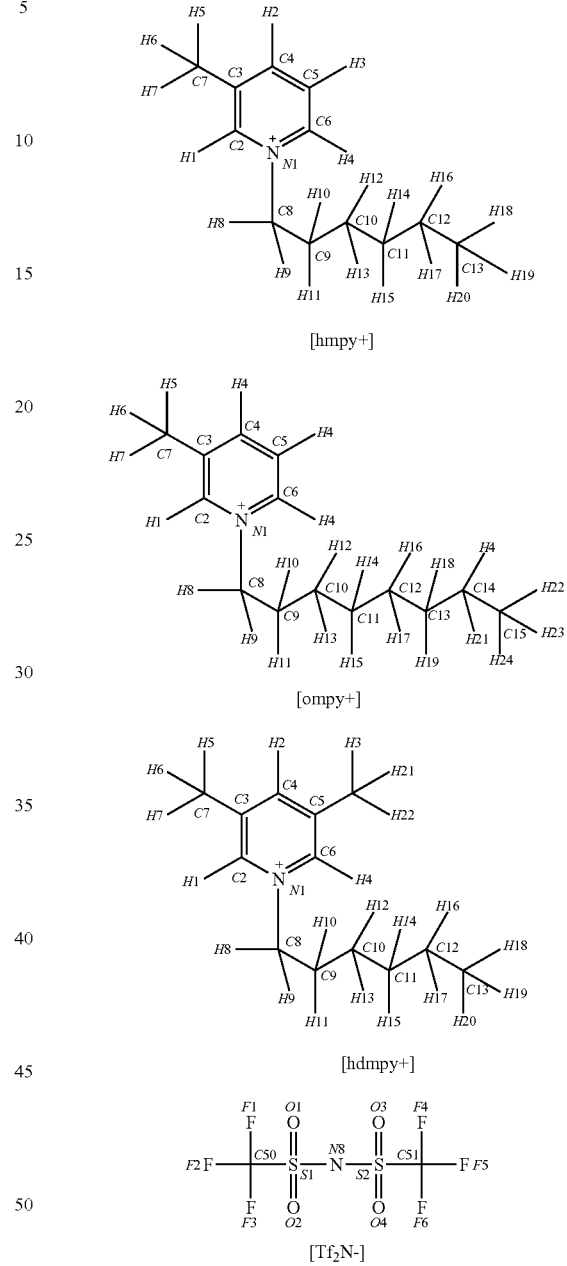

[hmpy+]

[ompy+]

[hdmpy+]

[Tf$_2$N-]

| Partial Atomic Charges and Lennard-Jones Parameters | | | | |
|---|---|---|---|---|
| Atom ID | Type | $q_i$ (e) | σ(Å) | $\epsilon_i$ (kcal mol$^{-1}$) |
| H$_{14}$ | HA | 0.017596 | 2.352 | 0.0220 |
| H$_{15}$ | HA | 0.017596 | 2.352 | 0.0220 |
| C$_{12}$ | CT2 | 0.172569 | 3.875 | 0.0550 |
| H$_{16}$ | HA | -0.027922 | 2.352 | 0.0220 |
| H$_{17}$ | HA | -0.027922 | 2.352 | 0.0220 |
| C$_{13}$ | CT3 | -0.170259 | 3.875 | 0.0550 |
| H$_{18}$ | HA | 0.044253 | 2.352 | 0.0220 |
| H$_{19}$ | HA | 0.044253 | 2.352 | 0.0220 |
| H$_{20}$ | HA | 0.044253 | 2.352 | 0.0220 |
| [ompy+] | | | | |
| C$_2$ | CN3B | -0.105213 | 3.207/3.688 | 0.1800 |
| C$_3$ | CN3 | 0.183650 | 3.385/3.893 | 0.0900 |

TABLE S.1-continued

Partial charges and Lennard-Jones parameters for Pyridiniums with Tf₂N.

[hmpy+]

[ompy+]

[hdmpy+]

[Tf₂N-]

| Atom ID | Type | $q_i$ (e) | $\sigma$(Å) | $\epsilon_i$ (kcal mol$^{-1}$) |
|---|---|---|---|---|
| $C_4$ | CN3A | −0.035962 | 3.207/3.688 | 0.1800 |
| $C_5$ | CN3 | −0.109911 | 3.385/3.893 | 0.0900 |
| $C_6$ | CN3B | 0.026085 | 3.207/3.688 | 0.1800 |
| $N_1$ | NN2 | 0.096507 | 3.296/3.791 | 0.2000 |
| $H_2$ | HN3B | 0.147299 | 1.604/1.844 | 0.0460 |
| $H_1$ | HN3B | 0.183690 | 1.604/1.844 | 0.0460 |
| $H_3$ | HN3B | 0.156722 | 1.604/1.844 | 0.0460 |
| $H_4$ | HN3B | 0.146546 | 1.604/1.844 | 0.0460 |
| $C_7$ | CN9 | −0.315079 | 3.635 | 0.0780 |
| $H_5$ | HN9 | 0.122295 | 2.388 | 0.0240 |
| $H_6$ | HN9 | 0.122295 | 2.388 | 0.0240 |
| $H_7$ | HN9 | 0.122295 | 2.388 | 0.0240 |
| $C_8$ | CN7B | −0.105793 | 4.054 | 0.0200 |
| $H_8$ | HN7 | 0.086753 | 2.352 | 0.0220 |
| $H_9$ | HN7 | 0.086753 | 2.352 | 0.0220 |
| $C_9$ | CT2 | 0.146788 | 3.875 | 0.0550 |
| $H_{10}$ | HA | −0.005416 | 2.352 | 0.0220 |
| $H_{11}$ | HA | −0.005416 | 2.352 | 0.0220 |
| $C_{10}$ | CT2 | 0.071775 | 3.875 | 0.0550 |
| $H_{12}$ | HA | −0.020200 | 2.352 | 0.0220 |
| $H_{13}$ | HA | −0.020200 | 2.352 | 0.0220 |
| $C_{11}$ | CT2 | −0.066054 | 3.875 | 0.0550 |
| $H_{14}$ | HA | 0.014064 | 2.352 | 0.0220 |
| $H_{15}$ | HA | 0.014064 | 2.352 | 0.0220 |
| $C_{12}$ | CT2 | 0.014905 | 3.875 | 0.0550 |
| $H_{16}$ | HA | 0.005025 | 2.352 | 0.0220 |

TABLE S.1-continued

Partial charges and Lennard-Jones parameters for Pyridiniums with Tf$_2$N.

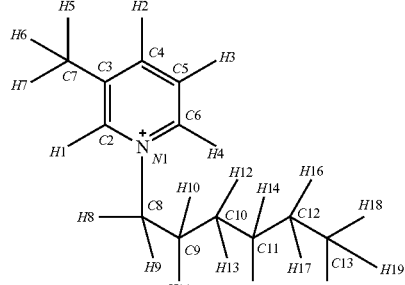

[hmpy+]

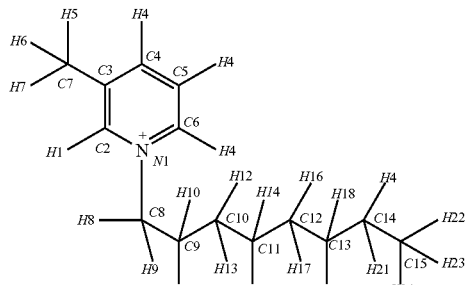

[ompy+]

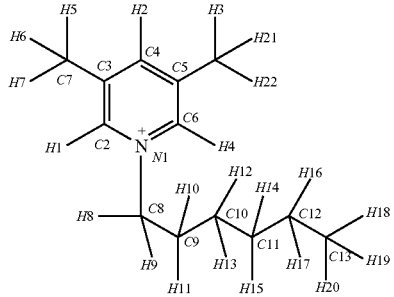

[hdmpy+]

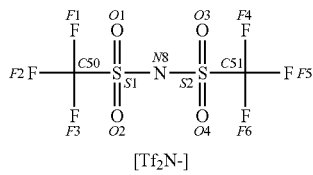

[Tf$_2$N-]

| Atom ID | Type | Partial Atomic Charges and Lennard-Jones Parameters | | |
|---|---|---|---|---|
| | | $q_i$ (e) | $\sigma$ (Å) | $\epsilon_i$ (kcal mol$^{-1}$) |
| H$_{17}$ | HA | 0.005025 | 2.352 | 0.0220 |
| C$_{13}$ | CT2 | 0.029233 | 3.875 | 0.0550 |
| H$_{18}$ | HA | −0.010404 | 2.352 | 0.0220 |
| H$_{19}$ | HA | −0.010404 | 2.352 | 0.0220 |
| C$_{14}$ | CT2 | 0.090529 | 3.875 | 0.0550 |
| H$_{20}$ | HA | −0.011092 | 2.352 | 0.0220 |
| H$_{21}$ | HA | −0.011092 | 2.352 | 0.0220 |
| C$_{15}$ | CT3 | −0.162384 | 3.875 | 0.0550 |
| H$_{22}$ | HA | 0.040774 | 2.352 | 0.0220 |
| H$_{23}$ | HA | 0.040774 | 2.352 | 0.0220 |
| H$_{24}$ | HA | 0.040774 | 2.352 | 0.0220 |

TABLE S.1-continued

Partial charges and Lennard-Jones parameters for Pyridiniums with Tf$_2$N.

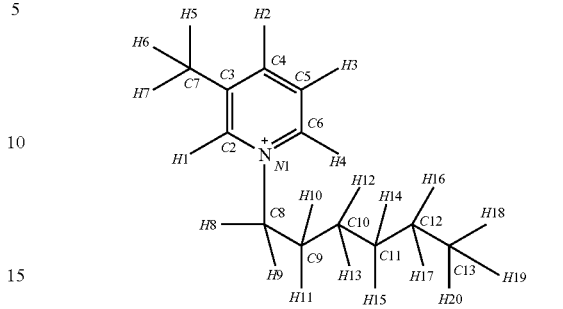

[hmpy+]

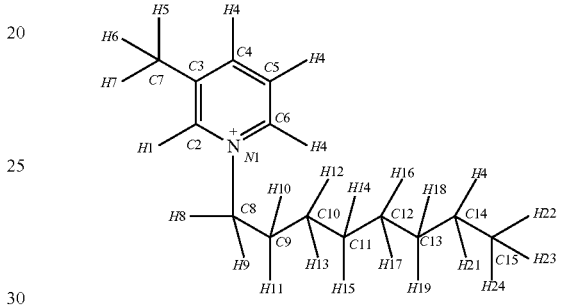

[ompy+]

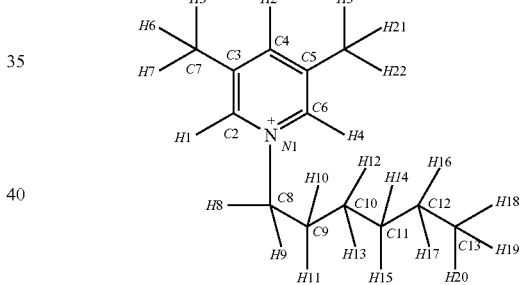

[hdmpy+]

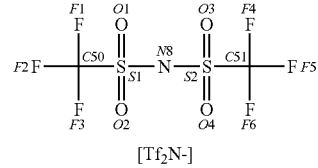

[Tf$_2$N-]

| Atom ID | Type | Partial Atomic Charges and Lennard-Jones Parameters | | |
|---|---|---|---|---|
| | | $q_i$ (e) | $\sigma$ (Å) | $\epsilon_i$ (kcal mol$^{-1}$) |
| | | [hdmpy+] | | |
| C$_2$ | CN3B | −0.138199 | 3.207/3.688 | 0.1800 |
| C$_3$ | CN3 | 0.210080 | 3.385/3.893 | 0.0900 |
| C$_4$ | CN3A | −0.176845 | 3.207/3.688 | 0.1800 |
| C$_5$ | CN3 | 0.219078 | 3.385/3.893 | 0.0900 |
| C$_6$ | CN3B | −0.105518 | 3.207/3.688 | 0.1800 |
| N$_1$ | NN2 | 0.099619 | 3.296/3.791 | 0.2000 |
| H$_2$ | HN3B | 0.172121 | 1.604/1.844 | 0.0460 |
| H$_1$ | HN3B | 0.190671 | 1.604/1.844 | 0.0460 |
| H$_4$ | HN3B | 0.172380 | 1.604/1.844 | 0.0460 |
| C$_7$ | CN9 | −0.296547 | 3.635 | 0.0780 |
| H$_5$ | HN9 | 0.116051 | 2.388 | 0.0240 |

TABLE S.1-continued

Partial charges and Lennard-Jones parameters for Pyridiniums with Tf₂N.

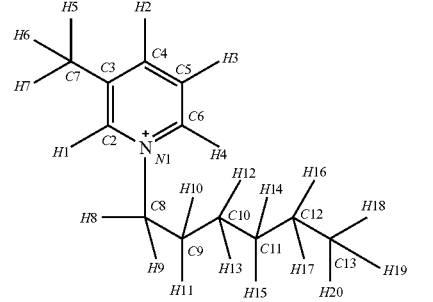

[hmpy+]

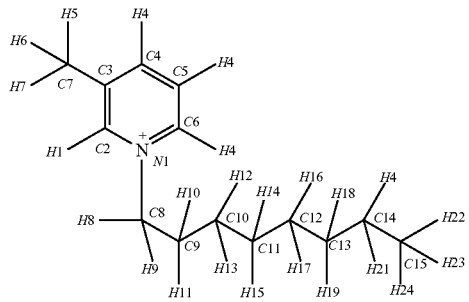

[ompy+]

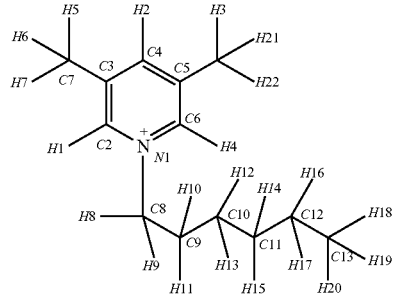

[hdmpy+]

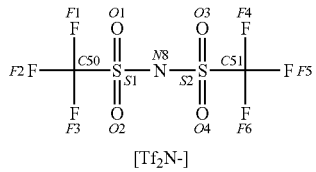

[Tf₂N-]

TABLE S.1-continued

Partial charges and Lennard-Jones parameters for Pyridiniums with Tf₂N.

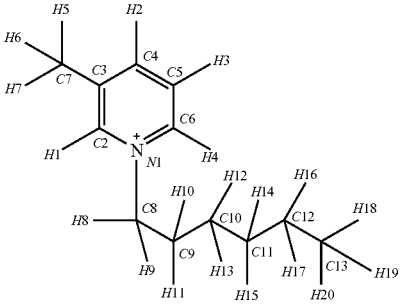

[hmpy+]

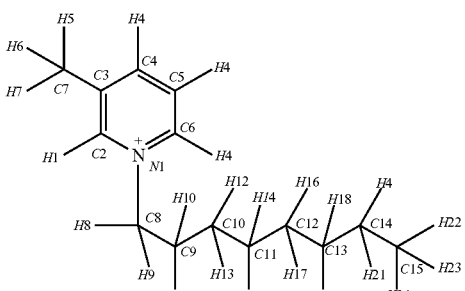

[ompy+]

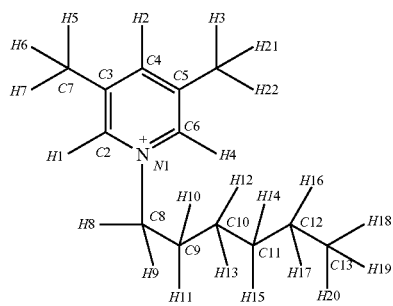

[hdmpy+]

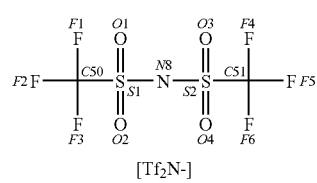

[Tf₂N-]

| Atom ID | Partial Atomic Charges and Lennard-Jones Parameters | | | |
|---|---|---|---|---|
| | Type | $q_i$ (e) | $\sigma$ (Å) | $\epsilon_i$ (kcal mol$^{-1}$) |
| $H_6$ | HN9 | 0.116051 | 2.388 | 0.0240 |
| $H_7$ | HN9 | 0.116051 | 2.388 | 0.0240 |
| $C_8$ | CN7B | -0.028491 | 4.054 | 0.0200 |
| $H_8$ | HN7 | 0.070834 | 2.352 | 0.0220 |
| $H_9$ | HN7 | 0.070834 | 2.352 | 0.0220 |
| $C_9$ | CT2 | 0.059978 | 3.875 | 0.0550 |
| $H_{10}$ | HA | 0.012358 | 2.352 | 0.0220 |
| $H_{11}$ | HA | 0.012358 | 2.352 | 0.0220 |
| $C_{10}$ | CT2 | 0.111583 | 3.875 | 0.0550 |
| $H_{12}$ | HA | -0.024660 | 2.352 | 0.0220 |
| $H_{13}$ | HA | -0.024660 | 2.352 | 0.0220 |
| $C_{11}$ | CT2 | -0.107733 | 3.875 | 0.0550 |
| $H_{14}$ | HA | 0.016582 | 2.352 | 0.0220 |

| Atom ID | Partial Atomic Charges and Lennard-Jones Parameters | | | |
|---|---|---|---|---|
| | Type | $q_i$ (e) | $\sigma$ (Å) | $\epsilon_i$ (kcal mol$^{-1}$) |
| $H_{15}$ | HA | 0.016582 | 2.352 | 0.0220 |
| $C_{12}$ | CT2 | 0.162389 | 3.875 | 0.0550 |
| $H_{16}$ | HA | -0.022634 | 2.352 | 0.0220 |
| $H_{17}$ | HA | -0.022634 | 2.352 | 0.0220 |
| $C_{13}$ | CT3 | -0.181877 | 3.875 | 0.0550 |
| $H_{18}$ | HA | 0.047804 | 2.352 | 0.0220 |
| $H_{19}$ | HA | 0.047804 | 2.352 | 0.0220 |
| $H_{20}$ | HA | 0.047804 | 2.352 | 0.0220 |
| $C_{14}$ | CN9 | -0.339512 | 3.635 | 0.0780 |
| $H_3$ | HN9 | 0.126766 | 2.388 | 0.0240 |
| $H_{21}$ | HN9 | 0.126766 | 2.388 | 0.0240 |
| $H_{22}$ | HN9 | 0.126766 | 2.388 | 0.0240 |

TABLE S.1-continued

Partial charges and Lennard-Jones parameters for Pyridiniums with Tf₂N.

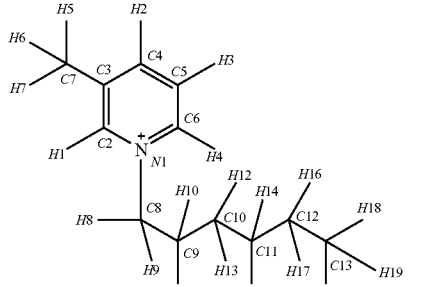

[hmpy+]

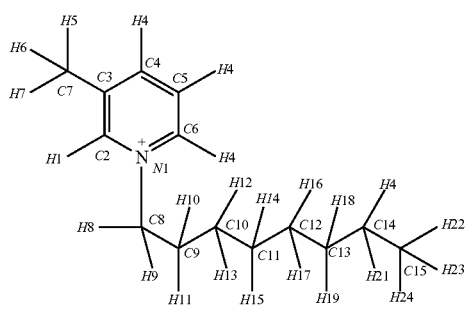

[ompy+]

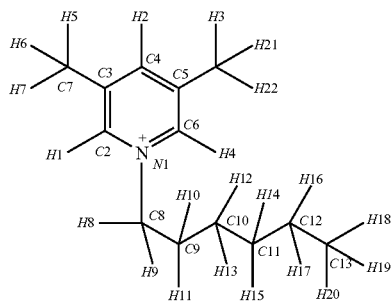

[hdmpy+]

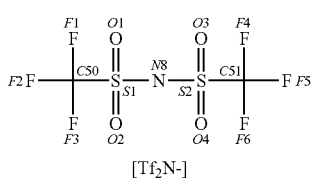

[Tf₂N-]

Partial Atomic Charges and Lennard-Jones Parameters

| Atom ID | Type | $q_i$ (e) | $\sigma$(Å) | $\epsilon_i$ (kcal mol$^{-1}$) |
|---|---|---|---|---|
| [Tf₂N-] From J. Phys. Chem. B. 2004, 108, 16893. | | | | |
| $N_8$ | NTF2 | −0.660000 | 3.250 | 0.1700 |
| $S_{1,2}$ | STF2 | 1.020000 | 3.550 | 0.2500 |
| $O_{1,2,3,4}$ | OTF2 | −0.530000 | 2.960 | 0.2100 |
| $F_{1,2,3,4,5,6}$ | FTF2 | −0.160000 | 2.950 | 0.0530 |
| $C_{50,51}$ | CTF2 | 0.350000 | 3.500 | 0.0660 |

TABLE S.2.a

Forcefield parameters for [Tf₂N—].
All parameters from J. Phys. Chem. B. 2004, 108, 16893.
Force Constants
[Tf₂N—]

Bonds

| Atoms | $k_b$ (kcal mol$^{-1}$ Å$^{-2}$) | $r_0$ (Å) |
|---|---|---|
| C—F | 441.80 | 1.3230 |
| C—S | 235.42 | 1.8180 |
| S—C | 637.07 | 1.4420 |
| N—S | 372.01 | 1.5700 |

Angles

| Atoms | $k_\theta$ (kcal mol$^{-1}$ rad$^{-2}$) | $\theta_0$ (deg) |
|---|---|---|
| F—C—F | 93.33 | 107.10 |
| S—C—F | 82.93 | 111.80 |
| C—S—O | 103.97 | 102.60 |
| O—S—O | 115.80 | 118.50 |
| O—S—N | 94.51 | 113.60 |
| C—S—N | 97.51 | 100.20 |
| S—N—S | 80.19 | 125.60 |

Dihedrals

| Atoms | $k_\chi$ (kcal mol$^{-1}$) | n | $\delta$(deg) |
|---|---|---|---|
| F—C—S—O | 0.1734 | 3 | 0 |
| S—N—S—O | −0.0018 | 3 | 0 |
| F—C—S—N | 0.1580 | 3 | 0 |
| S—N—S—C | 7.8329 | 1 | 0 |
|  | −2.4904 | 2 | 180 |
|  | −0.7636 | 3 | 0 |

TABLE S.2.b.

Forcefield parameters for [hmpy+].
Force Constants
[hmpy+]

Bonds

| Atoms | $k_b$ (kcal mol$^{-1}$ Å$^{-2}$) | $r_0$ (Å) |
|---|---|---|
| $C_8$—H | 309.00 | 1.0900 |
| $C_{9,10,11,12}$—H | 309.00 | 1.0961 |
| $C_{13}$—H | 322.00 | 1.0937 |
| $C_8$—$C_9$ | 200.00 | 1.5326 |
| $C_{9,10,11}$—$C_{10,11,12}$ | 222.50 | 1.5375 |
| $C_{12}$—$C_{13}$ | 222.50 | 1.5314 |
| $C_7$—H | 322.00 | 1.0921 |
| $C_3$—$C_7$ | 229.63 | 1.5041 |
| $C_{3,4}$—$C_{4,5}$ | 450.00 | 1.3968 |
| $C_{2,5}$—$C_{3,6}$ | 420.00 | 1.3864 |
| $C_{2,6}$—$N_1$ | 420.00 | 1.3505 |
| $C_5$—$H_3$ | 350.00 | 1.0834 |
| $C_4$—$H_2$ | 350.00 | 1.0853 |
| $C_{2,6}$—$H_{1,4}$ | 350.00 | 1.0820 |
| $N_1$—$C_8$ | 220.00 | 1.4978 |

Angles

| Atoms | $k_\theta$ (kcal mol$^{-1}$ rad$^{-2}$) | $\theta_0$ (deg) |
|---|---|---|
| $H_8$—$C_8$—$H_9$ | 35.50 | 107.44 |
| H—$C_8$—$C_9$ | 33.40 | 111.56 |
| $C_8$—$C_9$—H | 33.40 | 107.51 |
| $C_8$—$C_9$—$C_{10}$ | 58.35 | 115.74 |
| $C_{11}$—$C_{12}$—$C_{13}$ | 58.00 | 114.54 |
| H—$C_{9,10,11,12}$—H | 35.50 | 105.18 |
| H—$C_{13}$—H | 35.50 | 107.29 |
| $C_{9,12}$—$C_{9,12}$—H | 26.50 | 109.09 |
| H—$C_{12}$—$C_{13}$ | 34.60 | 109.29 |

TABLE S.2.b.-continued

Forcefield parameters for [hmpy+].
Force Constants
[hmpy+]

| Atoms | | |
|---|---|---|
| $C_{12}$—$C_{13}$—H | 34.60 | 111.57 |
| $N_1$—$C_8$—$C_9$ | 140.00 | 112.69 |
| H—$C_7$—H | 35.50 | 107.70 |
| $C_4$—$C_3$—$C_7$ | 45.80 | 121.88 |
| $C_2$—$C_3$—$C_7$ | 45.80 | 121.01 |
| $C_{3,5}$—$C_{2,6}$—$N_1$ | 120.00 | 121.29 |
| $C_{3,5}$—$C_{2,6}$—$H_{1,4}$ | 80.00 | 122.51 |
| $C_{2,4}$—$C_{3,5}$—$C_{4,6}$ | 40.00 | 117.88 |
| $C_3$—$C_4$—$C_5$ | 50.00 | 120.87 |
| $C_{3,5}$—$C_4$—$H_2$ | 80.00 | 119.57 |
| $C_4$—$C_5$—$H_3$ | 30.00 | 121.37 |
| $C_6$—$C_5$—$H_3$ | 30.00 | 119.20 |
| $C_2$—$N_1$—$C_6$ | 30.00 | 120.78 |
| $C_{2,6}$—$N_1$—$C_8$ | 70.00 | 119.60 |
| $C_3$—$C_7$—H | 33.43 | 111.19 |
| $N_1$—$C_8$—H | 43.00 | 106.63 |
| $C_{9,10}$—$C_{10,11}$—$C_{11,12}$ | 58.35 | 115.56 |
| $N_1$—$C_{2,6}$—$H_{1,4}$ | 80.00 | 116.20 |

Dihedrals

| Atoms | $k_\chi$ (kcal mol$^{-1}$) | n | $\delta$(deg) |
|---|---|---|---|
| H—$C_{12}$—$C_{13}$—H | 0.160 | 3 | 0 |
| $C_{11}$—$C_{12}$—$C_{13}$—H | 0.160 | 3 | 0 |
| H—$C_8$—$C_9$—H | 0.195 | 3 | 0 |
| H—$C_8$—$C_9$—$C_{10}$ | 0.195 | 3 | 0 |
| H—$C_{9,10,11}$—$C_{10,11,12}$—H | 0.195 | 3 | 0 |
| $C_8$—$C_9$—$C_{10}$—H | 0.195 | 3 | 0 |
| H—$C_{11}$—$C_{12}$—$C_{13}$ | 0.195 | 3 | 0 |
| $C_{2,6}$—$N_1$—$C_8$—$C_9$ | 0.200 | 4 | 0 |
| $N_1$—$C_8$—$C_9$—H | 0.000 | 3 | 0 |
| $N_1$—$C_8$—$C_9$—$C_{10}$ | 0.000 | 3 | 0 |
| $C_4$—$C_3$—$C_7$—H | 0.195 | 2 | 180 |
| $C_2$—$C_3$—$C_7$—H | 0.195 | 2 | 180 |
| $C_4$—$C_{3,5}$—$C_{2,6}$—$N_1$ | 7.000 | 2 | 180 |
| $C_{3,5}$—$C_{2,6}$—$N_1$—$C_{6,2}$ | 4.000 | 2 | 180 |
| $C_{3,2}$—$C_{4,3}$—$C_{5,4}$—$C_{6,5}$ | 6.000 | 2 | 180 |
| $C_{2,6}$—$N_1$—$C_8$—H | 0.195 | 3 | 0 |
| $H_3$—$C_5$—$C_4$—$H_2$ | 1.000 | 2 | 180 |
| $H_2$—$C_4$—$C_3$—$C_7$ | 1.000 | 2 | 180 |
| $C_{2,8}$—$C_{3,5}$—$C_4$—$H_2$ | 1.000 | 2 | 180 |
| $C_5$—$C_4$—$C_3$—$C_7$ | 1.000 | 2 | 180 |
| $C_3$—$C_4$—$C_5$—$H_3$ | 1.000 | 2 | 180 |
| $C_7$—$C_3$—$C_2$—$N_1$ | 1.000 | 2 | 180 |
| $H_4$—$C_6$—$C_5$—$H_3$ | 1.000 | 2 | 180 |
| $C_4$—$C_{3,5}$—$C_{2,6}$—$H_{1,4}$ | 1.000 | 2 | 180 |
| $C_7$—$C_3$—$C_2$—$H_1$ | 1.000 | 2 | 180 |
| $N_1$—$C_6$—$C_5$—$H_3$ | 1.000 | 2 | 180 |
| $C_{3,5}$—$C_{2,6}$—$N_1$—$C_8$ | 1.000 | 2 | 180 |
| $C_{2,6}$—$N_1$—$C_{6,2}$—$H_{4,1}$ | 1.000 | 2 | 180 |
| $C_8$—$N_1$—$C_{2,6}$—$H_{1,4}$ | 1.000 | 2 | 180 |
| $C_8$—$C_9$—$C_{10}$—$C_{11}$ | 0.195 | 3 | 0 |
| $C_{9-12}$—$C_{10,11}$—$C_{9-12}$—H | 0.195 | 3 | 0 |
| $C_9$—$C_{10}$—$C_{11}$—$C_{12}$ | 0.195 | 3 | 0 |
| $C_{10}$—$C_{11}$—$C_{12}$—$C_{13}$ | 0.195 | 3 | 0 |

Impropers

| Atoms | $k_\psi$ (kcal mol$^{-1}$ rad$^{-2}$) | $\psi_0$ (deg) |
|---|---|---|
| $N_1$—$C_2$—$C_6$—$C_8$ | 0.600 | 0 |
| $C_{2,6}$—$N_1$—$C_{3,5}$—$H_{1,4}$ | 13.000 | 0 |
| $C_3$—$C_2$—$C_4$—$C_7$ | 0.500 | 0 |
| $C_4$—$C_3$—$C_5$—$H_2$ | 13.000 | 0 |
| $C_5$—$C_4$—$C_6$—$H_3$ | 15.000 | 0 |

TABLE S.2.c

Forcefield parameters for [ompy+].
Force Constants
[ompy+]

Bonds

| Atoms | $k_b$ (kcal mol$^{-1}$ Å$^{-2}$) | $r_0$ (Å) |
|---|---|---|
| $C_8$—H | 309.00 | 1.0900 |
| $C_{9,10,11,12,13,14}$—H | 309.00 | 1.0961 |
| $C_{15}$—H | 322.00 | 1.0937 |
| $C_8$—$C_9$ | 200.00 | 1.5326 |
| $C_{9-13}$—$C_{10-14}$ | 222.50 | 1.5375 |
| $C_{14}$—$C_{15}$ | 222.50 | 1.5314 |
| $C_7$—H | 322.00 | 1.0921 |
| $C_3$—$C_7$ | 229.63 | 1.5041 |
| $C_{3,4}$—$C_{4,5}$ | 450.00 | 1.3968 |
| $C_{2,5}$—$C_{3,6}$ | 420.00 | 1.3864 |
| $C_{2,6}$—$N_1$ | 420.00 | 1.3505 |
| $C_5$—$C_3$ | 350.00 | 1.0834 |
| $C_4$—$C_2$ | 350.00 | 1.0853 |
| $C_{2,6}$—$H_{1,4}$ | 350.00 | 1.0820 |
| $N_1$—$C_8$ | 220.00 | 1.4978 |

Angles

| Atoms | $k_\theta$ (kcal mol$^{-1}$ rad$^{-2}$) | $\theta_0$ (deg) |
|---|---|---|
| $H_8$—$C_8$—$H_9$ | 35.50 | 107.44 |
| H—$C_8$—$C_9$ | 33.40 | 111.56 |
| $C_8$—$C_9$—H | 33.40 | 107.51 |
| $C_8$—$C_9$—$C_{10}$ | 58.35 | 115.74 |
| $C_{13}$—$C_{14}$—$C_{15}$ | 58.00 | 114.54 |
| H—$C_{9-14}$—H | 35.50 | 105.18 |
| H—$C_{15}$—H | 35.50 | 107.29 |
| $C_{9-14}$—$C_{9-14}$—H | 26.50 | 109.09 |
| H—$C_{14}$—$C_{15}$ | 34.60 | 109.29 |
| $C_{14}$—$C_{15}$—H | 34.60 | 111.57 |
| $N_1$—$C_8$—$C_9$ | 140.00 | 112.69 |
| H—$C_7$—H | 35.50 | 107.70 |
| $C_4$—$C_3$—$C_7$ | 45.80 | 121.88 |
| $C_2$—$C_3$—$C_7$ | 45.80 | 121.01 |
| $C_{3,5}$—$C_{2,6}$—$N_1$ | 120.00 | 121.29 |
| $C_{3,5}$—$C_{2,6}$—$H_{1,4}$ | 80.00 | 122.51 |
| $C_{2,4}$—$C_{3,5}$—$C_{4,6}$ | 40.00 | 117.88 |
| $C_3$—$C_4$—$C_5$ | 50.00 | 120.87 |
| $C_{3,5}$—$C_4$—$H_2$ | 80.00 | 119.57 |
| $C_4$—$C_5$—$H_3$ | 30.00 | 121.37 |
| $C_6$—$C_5$—$H_3$ | 30.00 | 119.20 |
| $C_2$—$N_1$—$C_6$ | 30.00 | 120.78 |
| $C_{2,6}$—$N_1$—$C_6$ | 70.00 | 119.60 |
| $C_3$—$C_7$—H | 33.43 | 111.19 |
| $N_1$—$C_8$—H | 43.00 | 106.63 |
| $C_{9-12}$—$C_{10-13}$—$C_{11-14}$ | 58.35 | 115.56 |
| $N_1$—$C_{2,6}$—$H_{14}$ | 80.00 | 116.20 |

Dihedrals

| Atoms | $k_\chi$ (kcal mol$^{-1}$) | n | $\delta$(deg) |
|---|---|---|---|
| H—$C_{14}C_{15}$H | 0.160 | 3 | 0 |
| $C_{13}C_{14}C_{15}$ | 0.160 | 3 | 0 |
| H—$C_8$—$C_9$—H | 0.195 | 3 | 0 |
| H—$C_8$—$C_9$—$C_{10}$ | 0.195 | 3 | 0 |
| H—$C_{9-13}C_{10-14}$—H | 0.195 | 3 | 0 |
| $C_8$—$C_9$—$C_{10}$—H | 0.195 | 3 | 0 |
| H—$C_{13}$—$C_{14}$—$C_{15}$ | 0.195 | 3 | 0 |
| $C_{2,6}$—$N_1$—$C_8$—$C_9$ | 0.200 | 4 | 0 |
| $N_1$—$C_8$—$C_9$—H | 0.000 | 3 | 0 |
| $N_1$—$C_8$—$C_9$—$C_{10}$ | 0.000 | 3 | 0 |
| $C_4$—$C_3$—$C_7$—H | 0.195 | 2 | 180 |
| $C_2$—$C_3$—$C_7$—H | 0.195 | 2 | 180 |
| $C_4$—$C_{3,5}$—$C_{2,6}$—$N_1$ | 7.000 | 2 | 180 |
| $C_{3,5}$—$C_{2,6}$—$N_1$—$C_{6,2}$ | 4.000 | 2 | 180 |
| $C_{3,2}$—$C_{4,3}$—$C_{5,4}$—$C_{6,5}$ | 6.000 | 2 | 180 |
| $C_{2,6}$—$N_1$—$C_8$—H | 0.195 | 3 | 0 |
| $H_3$—$C_5$—$C_4$—$H_2$ | 1.000 | 2 | 180 |
| $H_2$—$C_4$—$C_3$—$C_7$ | 1.000 | 2 | 180 |
| $C_{2,6}$—$C_{3,5}$—$C_4$—$H_2$ | 1.000 | 2 | 180 |

TABLE S.2.c-continued

Forcefield parameters for [ompy+].
Force Constants
[ompy+]

| Atoms | | | |
|---|---|---|---|
| $C_5$—$C_4$—$C_3$—$C_7$ | 1.000 | 2 | 180 |
| $C_3$—$C_4$—$C_5$—$H_3$ | 1.000 | 2 | 180 |
| $C_7$—$C_3$—$C_2$—$N_1$ | 1.000 | 2 | 180 |
| $H_4$—$C_6$—$C_5$—$H_3$ | 1.000 | 2 | 180 |
| $C_4$—$C_{3,5}$—$C_{2,6}$—$H_{1,4}$ | 1.000 | 2 | 180 |
| $C_7$—$C_3$—$C_2$—$H_1$ | 1.000 | 2 | 180 |
| $N_1$—$C_6$—$C_5$—$H_3$ | 1.000 | 2 | 180 |
| $C_{3,5}$—$C_{2,6}$—$N_1$—$C_8$ | 1.000 | 2 | 180 |
| $C_{2,6}$—$N_1$—$C_{6,2}$—$H_{4,1}$ | 1.000 | 2 | 180 |
| $C_8$—$N_1$—$C_{2,6}$—$H_{1,4}$ | 1.000 | 2 | 180 |
| $C_8$—$C_9$—$C_{10}$—$C_{11}$ | 0.195 | 3 | 0 |
| $C_{9\text{-}14}$—$C_{10\text{-}13}$—$C_{9\text{-}14}$—H | 0.195 | 3 | 0 |
| $C_{9\text{-}11}$—$C_{10\text{-}12}$—$C_{11\text{-}13}$—$C_{12\text{-}14}$ | 0.195 | 3 | 0 |
| $C_{12}$—$C_{13}$—$C_{14}$—$C_{15}$ | 0.195 | 3 | 0 |

Impropers

| Atoms | $k_\psi$ (kcal mol$^{-1}$ rad$^{-2}$) | $\psi_0$ (deg) |
|---|---|---|
| $N_1$—$C_2$—$C_6$—$C_8$ | 0.600 | 0 |
| $C_{2,6}$—$N_1$—$C_{3,5}$—$H_{1,4}$ | 13.000 | 0 |
| $C_3$—$C_2$—$C_4$—$C_7$ | 0.500 | 0 |
| $C_4$—$C_3$—$C_5$—$H_2$ | 13.000 | 0 |
| $C_5$—$C_4$—$C_6$—$H_3$ | 15.000 | 0 |

TABLE S.2.d

Forcefield parameters for [hdmpy+].
Force Constants
[hdmpy+]

Bonds

| Atoms | $k_b$ (kcal mol$^{-1}$ Å$^{-2}$) | $r_0$ (A) |
|---|---|---|
| $C_8$—H | 309.00 | 1.0900 |
| $C_{9,10,11,12}$—H | 309.00 | 1.0961 |
| $C_{13}$—H | 322.00 | 1.0937 |
| $C_8$—$C_9$ | 200.00 | 1.5326 |
| $C_{9,10,11}$—$C_{10,11,12}$ | 222.50 | 1.5375 |
| $C_{12}$—$C_{13}$ | 222.50 | 1.5314 |
| $C_{7,14}$—H | 322.00 | 1.0921 |
| $C_{3,5}$—$C_{7,14}$ | 229.63 | 1.5041 |
| $C_{3,4}$—$C_{4,5}$ | 450.00 | 1.3968 |
| $C_{2,5}$—$C_{3,6}$ | 420.00 | 1.3864 |
| $C_{2,6}$—$N_1$ | 420.00 | 1.3505 |
| $C_4$—$H_2$ | 350.00 | 1.0853 |
| $C_{2,6}$—$H_{1,4}$ | 350.00 | 1.0820 |
| $N_1$—$C_8$ | 220.00 | 1.4978 |

Angles

| Atoms | $k_\theta$ (kcal mol$^{-1}$ rad$^{-2}$) | $\theta_0$ (deg) |
|---|---|---|
| $H_8$—$C_8$—$H_9$ | 35.50 | 107.44 |
| H—$C_8$—$C_9$ | 33.40 | 111.56 |
| $C_8$—$C_9$—H | 33.40 | 107.51 |
| $C_8$—$C_9$—$C_{10}$ | 58.35 | 115.74 |
| $C_{11}$—$C_{12}$—$C_{13}$ | 58.00 | 114.54 |
| H—$C_{9,10,11,12}$—H | 35.50 | 105.18 |
| H—$C_{13}$—H | 35.50 | 107.29 |
| $C_{9\text{-}12}$—$C_{9\text{-}12}$—H | 26.50 | 109.09 |
| H—$C_{12}$—$C_{13}$ | 34.60 | 109.29 |
| $C_{12}$—$C_{13}$—H | 34.60 | 111.57 |
| $N_1$—$C_8$—$C_9$ | 140.00 | 112.69 |
| H—$C_{7,14}$—H | 35.50 | 107.70 |
| $C_4$—$C_{3,5}$—$C_{7,14}$ | 45.80 | 121.88 |
| $C_{2,6}$—$C_{3,5}$—$C_{7,14}$ | 45.80 | 121.01 |
| $C_{3,5}$—$C_{2,6}$—$N_1$ | 120.00 | 121.29 |
| $C_{3,5}$—$C_{2,6}$—$H_{1,4}$ | 80.00 | 122.51 |
| $C_{2,4}$—$C_{3,5}$—$C_{7,14}$ | 40.00 | 117.88 |
| $C_3$—$C_4$—$C_5$ | 50.00 | 120.87 |

TABLE S.2.d-continued

Forcefield parameters for [hdmpy+].
Force Constants
[hdmpy+]

| | | |
|---|---|---|
| $C_{3,5}$—$C_4$—$H_2$ | 80.00 | 119.57 |
| $C_2$—$N_1$—$C_6$ | 30.00 | 120.78 |
| $C_{2,6}$—$N_1$—$C_8$ | 70.00 | 119.60 |
| $C_{3,5}$—$C_{7,14}$—$H_2$ | 33.43 | 111.19 |
| $N_1$—$C_8$—H | 43.00 | 106.63 |
| $C_{9,10}$—$C_{10,11}$—$C_{11,12}$ | 58.35 | 115.56 |
| $N_1$—$C_{2,6}$—$H_{1,4}$ | 80.00 | 116.20 |

Dihedrals

| Atoms | $k_\chi$ (kcal mol$^{-1}$) | n | δ(deg) |
|---|---|---|---|
| H—$C_{12}$—$C_{13}$—H | 0.160 | 3 | 0 |
| $C_{11}$—$C_{12}$—$C_{13}$—H | 0.160 | 3 | 0 |
| H—$C_8$—$C_9$—H | 0.195 | 3 | 0 |
| H—$C_8$—$C_9$—$C_{10}$ | 0.195 | 3 | 0 |
| H—$C_{9,10,11}$—$C_{10,11,12}$—H | 0.195 | 3 | 0 |
| $C_8$—$C_9$—$C_{10}$—H | 0.195 | 3 | 0 |
| H—$C_{11}$—$C_{12}$—$C_{13}$ | 0.195 | 3 | 0 |
| $C_{2,6}$—$N_1$—$C_8$—$C_9$ | 0.200 | 4 | 0 |
| $N_1$—$C_8$—$C_9$—H | 0.000 | 3 | 0 |
| $N_1$—$C_8$—$C_9$—$C_{10}$ | 0.000 | 3 | 0 |
| $C_4$—$C_{3,5}$—$C_{7,14}$—H | 0.195 | 2 | 180 |
| $C_{2,6}$—$C_{3,5}$—$C_{7,14}$—H | 0.195 | 2 | 180 |
| $C_4$—$C_{3,5}$—$C_{2,6}$—$N_1$ | 7.000 | 2 | 180 |
| $C_{3,5}$—$C_{2,6}$—$N_1$—$C_{6,2}$ | 4.000 | 2 | 180 |
| $C_{3,2}$—$C_{4,3}$—$C_{5,4}$—$C_{6,5}$ | 6.000 | 2 | 180 |
| $C_{2,6}$—$N_1$—$C_8$—H | 0.195 | 3 | 0 |
| $H_2$—$C_4$—$C_{3,5}$—$C_{7,14}$ | 1.000 | 2 | 180 |
| $C_{2,6}$—$C_{3,5}$—$C_4$—$H_2$ | 1.000 | 2 | 180 |
| $C_{3,5}$—$C_4$—$C_{5,3}$—$C_{14,7}$ | 1.000 | 2 | 180 |
| $C_{7,14}$—$C_{3,5}$—$C_{2,6}$—$N_1$ | 1.000 | 2 | 180 |
| $C_4$—$C_{3,5}$—$C_{2,6}$—$H_{1,4}$ | 1.000 | 2 | 180 |
| $C_{7,14}$—$C_{3,6}$—$C_{2,5}$—$H_{1,4}$ | 1.000 | 2 | 180 |
| $C_{3,5}$—$C_{2,6}$—$N_1$—$C_8$ | 1.000 | 2 | 180 |
| $C_{2,6}$—$N_1$—$C_{6,2}$—$H_{4,1}$ | 1.000 | 2 | 180 |
| $C_8$—$N_1$—$C_{2,6}$—$H_{1,4}$ | 1.000 | 2 | 180 |
| $C_8$—$C_9$—$C_{10}$—$C_{11}$ | 0.195 | 3 | 0 |
| $C_{9\text{-}12}$—$C_{10,11}$—$C_{9\text{-}12}$—H | 0.195 | 3 | 0 |
| $C_9$—$C_{10}$—$C_{11}$—$C_{12}$ | 0.195 | 3 | 0 |
| $C_{10}$—$C_{11}$—$C_{12}$—$C_{13}$ | 0.195 | 3 | 0 |

Impropers

| Atoms | $k_\psi$ (kcal mol$^{-1}$ rad$^{-2}$) | $\psi_0$ (deg) |
|---|---|---|
| $N_1$—$C_2$—$C_6$—$C_8$ | 0.600 | 0 |
| $C_{26}$—$N_1$—$C_{3,5}$—$H_{1,4}$ | 13.000 | 0 |
| $C_3$—$C_2$—$C_4$—$C_7$ | 0.500 | 0 |
| $C_4$—$C_3$—$C_5$—$H_2$ | 13.000 | 0 |
| $C_5$—$C_4$—$C_6$—$C_{14}$ | 0.500 | 0 |

Force fields for a variety of anions have already been identified. The cation forcefield was further characterized by computing the density, compressibility and expansivity of ionic liquids formed from the cations paired with the $Tf_2N$ anion. Results are presented in Table 23. Properties were also computed that have not yet been measured for this system, including cohesive energy densities and heat capacities. These values are also reported in Table 23.

TABLE 23

Simulated and experimental densities for 1-n-hexyl-3-methylpyridinium [hmpy], 1-n-octyl-3-methylpyridinium [ompy] and 1-n-hexyl-3,5-dimethylpyridinium [hdmpy] Tf$_2$N ionic liquids. Also listed are computed heats of vaporization ($\Delta U$), cohesive energy density (c), expansivities ($\alpha$), compressibilities ($\kappa_T$) and heat capacities ($C_p$ and $C_v$). Uncertainties are reported as standard deviations ($\sigma$).
Pyridinium-based ILs

| | T(K) | ρ(g/cc) | σ(g/cc) | % error | exp ρ(g/cc) |
|---|---|---|---|---|---|
| hmPyTf2N | 298 | 1.409 | 0.004 | 4.457 | 1.349 |
| 458.442900 | 308 | 1.403 | 0.005 | 4.659 | 1.340 |
| | 318 | 1.392 | 0.004 | 4.501 | 1.332 |
| | 328 | 1.389 | 0.006 | 4.955 | 1.324 |
| | 338 | 1.377 | 0.005 | 4.730 | 1.315 |
| | 348 | 1.374 | 0.007 | 5.146 | 1.307 |
| omPyTf2N | 298 | 1.343 | 0.005 | 2.552 | 1.309 |
| 486.496340 | 308 | 1.338 | 0.004 | 2.883 | 1.300 |
| | 318 | 1.333 | 0.005 | 3.246 | 1.292 |
| | 328 | 1.326 | 0.005 | 3.405 | 1.283 |
| | 338 | 1.320 | 0.005 | 3.618 | 1.274 |
| | 348 | 1.309 | 0.006 | 3.514 | 1.265 |
| hdmPyTf2N | 298 | 1.363 | 0.004 | 1.369 | 1.344 |
| 472.469620 | 308 | 1.356 | 0.005 | 1.548 | 1.335 |
| | 318 | 1.343 | 0.005 | 1.264 | 1.326 |
| | 328 | 1.348 | 0.005 | 2.340 | 1.317 |
| | 338 | 1.343 | 0.006 | 2.608 | 1.309 |
| | 348 | 1.332 | 0.005 | 2.456 | 1.300 |

| | T(K) | ΔU(kJ/mol) | σ(kJ/mol) | c(J/cc) | σ(J/cc) |
|---|---|---|---|---|---|
| hmPyTf2N | 298 | 179 | 37 | 549 | 62 |
| 458.442900 | 308 | 174 | 38 | 533 | 61 |
| | 318 | 179 | 38 | 542 | 63 |
| | 328 | 178 | 40 | 538 | 66 |
| | 338 | 177 | 43 | 532 | 68 |
| | 348 | 181 | 43 | 541 | 70 |
| omPyTf2N | 298 | 186 | 39 | 513 | 55 |
| 486.496340 | 308 | 183 | 41 | 504 | 56 |
| | 318 | 184 | 43 | 505 | 59 |
| | 328 | 186 | 44 | 507 | 61 |
| | 338 | 177 | 45 | 481 | 59 |
| | 348 | 180 | 45 | 483 | 59 |
| hdmPyTf2N | 298 | 174 | 38 | 503 | 55 |
| 472.469620 | 308 | 171 | 40 | 491 | 56 |
| | 318 | 170 | 41 | 483 | 56 |
| | 328 | 173 | 41 | 492 | 58 |
| | 338 | 172 | 44 | 490 | 61 |
| | 348 | 174 | 44 | 489 | 61 |

| | $\alpha(K^{-1}) \times 10^4$ | $\sigma_\alpha(K^{-1}) \times 10^4$ | $\kappa_T$ (bar$^{-1}$) × 10$^5$ | $\sigma_{\kappa T}$ (bar$^{-1}$) × 10$^5$ |
|---|---|---|---|---|
| hmPyTf2N | 5.23 | 0.38 | 1.84 | 0.21 |
| omPyTf2N | 4.95 | 0.39 | 1.97 | 0.22 |
| hdmPyTf2N | 4.02 | 0.80 | 1.93 | 0.23 |

| | Cp(J/K mol) | $\sigma_{Cp}$(J/K mol) | Cv(J/K mol) | $\sigma_{Cv}$(J/K mol) |
|---|---|---|---|---|
| hmPyTf2N | 1291 | 16 | 1135 | 33 |
| omPyTf2N | 1454 | 23 | 1310 | 36 |
| hdmPyTf2N | 1345 | 13 | 1252 | 41 |

Calculations have also been performed to determine the self-diffusivity of these three ionic liquids as a function of temperature. These values are reported in Table 24. The self-diffusivities were also measured for these compounds using a pulsed field-gradient nuclear magnetic resonance technique.

TABLE 24

Preliminary self-diffusion coefficients for the three different pyridinium-based ILs as a function of temperature. D+ and D− refer to the diffusivities of the cation and anion, respectively. The uncertainty of the diffusivities is high, especially at lower temperatures, making comparison among the different cations and between temperatures difficult. Experimental values were obtained from pulsed-field gradient NMR measurements.

| IL | T(K) | D+(m²/s) | $\sigma_{A+}$(m²/s) | D+(exp) m2/s | D−(m²/s) | $\sigma_{A-}$(m²/s) | D−(exp) m2/s |
|---|---|---|---|---|---|---|---|
| hmPyTf$_2$N | 298 | 7.53E−11 | 2.36E−11 | 1.223E−11 | 7.52E−11 | 2.37E−11 | 1.207E−11 |
| | 308 | 1E−10 | 3.41E−11 | 2.158E−11 | 9.85E−11 | 3.4E−11 | 2.122E−11 |
| | 318 | 5.38E−11 | 1.49E−11 | 3.464E−11 | 5.33E−11 | 1.5E−11 | 3.415E−11 |
| | 328 | 4.38E−11 | 7.53E−12 | 5.628E−11 | 4.28E−11 | 7.89E−12 | 5.544E−11 |
| | 338 | 3.48E−11 | 7.94E−12 | 9.688E−11 | 3.51E−11 | 8.34E−12 | 9.658E−11 |
| | 348 | 3.07E−11 | 3.92E−12 | 1.799E−10 | 3.08E−11 | 4.34E−12 | 1.769E−10 |
| omPyTf$_2$N | 298 | 5.07E−11 | 3.47E−12 | 8.652E−12 | 4.99E−11 | 3.44E−12 | 9.155E−12 |
| | 308 | 1.13E−11 | 1.45E−12 | 1.57E−11 | 1.13E−11 | 1.56E−12 | 1.659E−11 |
| | 318 | 1.54E−10 | 4.67E−12 | 2.564E−11 | 1.56E−10 | 5.58E−12 | 2.713E−11 |
| | 328 | 3.34E−11 | 8.13E−12 | 4.037E−11 | 3.27E−11 | 8.06E−12 | 4.302E−11 |
| | 338 | 1.42E−11 | 1.38E−12 | 6.774E−11 | 1.28E−11 | 1.58E−12 | 7.158E−11 |
| | 348 | 1.66E−10 | 4.35E−11 | 1.182E−10 | 1.64E−10 | 4.25E−11 | 1.24E−10 |
| hdmPyTf$_2$N | 298 | 9.11E−11 | 2.57E−12 | 9.316E−12 | 9.3E−11 | 2.39E−12 | 9.799E−12 |
| | 308 | 1.23E−10 | 3.3E−11 | 1.683E−11 | 1.24E−10 | 3.31E−11 | 1.804E−11 |
| | 318 | 1.8E−11 | 2.26E−12 | 2.856E−11 | 1.76E−11 | 2.23E−12 | 3.017E−11 |
| | 328 | 6.57E−11 | 1.78E−11 | 4.916E−11 | 6.57E−11 | 1.8E−11 | 5.163E−11 |
| | 338 | 8.01E−11 | 2.14E−11 | 8.541E−11 | 8.21E−11 | 2.17E−11 | 8.847E−11 |
| | 348 | 4.16E−11 | 8.65E−12 | 1.733E−10 | 3.85E−11 | 7.28E−12 | 1.713E−10 |

Example 8 hDMAP-Tf$_2$N Aminopyridinium Compound Density vs Pressure Study

The present example demonstrates that the density of the aminopyridinium ionic compounds of the present invention change in proportion with pressure.

TABLE 25

| hDMAP-Tf$_2$N | | | (small cell) | | |
|---|---|---|---|---|---|
| Empty Cell (g) | | | 12.3481 | | |
| Sample Mass | | | 6.9531 | | |
| Pressure (psi) | Temperature (° C.) | Mark | Volume (mL) | Density (g/mL) | V/Vo |
| 14.4059 | 23.0 | 26.7 | 5.17 | 1.3449 | 1.0000 |
| 5000 | 25.0 | 25.6 | 5.11 | 1.3607 | 0.9884 |
| 10000 | 25.0 | 24.5 | 5.04 | 1.3796 | 0.9749 |
| 15000 | 25.0 | 23.5 | 4.98 | 1.3962 | 0.9632 |
| 20000 | 25.0 | 22.9 | 4.95 | 1.4047 | 0.9574 |
| 25000 | 25.0 | 21.7 | 4.88 | 1.4248 | 0.9439 |

| Water Content Trial | Content (ppm) | Content (%) |
|---|---|---|
| 1 | 301.2 | 0.03012 |
| 2 | 303.1 | 0.03031 |
| 3 | 283.6 | 0.02836 |
| average | 296.0 | 0.02960 |

Example 9 hmDMAP-Tf$_2$N Aminopyridinium Compound Density vs Pressure Study

Another aminopyridinium compound that was examined was hmDMAP-Tf$_2$N. The following Table 26 presents the results obtained with this compound.

TABLE 26

| hmDMAP-Tf$_2$N | | | (small cell) | | |
|---|---|---|---|---|---|
| Empty Cell (g) | | | 12.3481 | | |
| Sample Mass | | | 6.8660 | | |
| Pressure (psi) | Temperature (° C.) | Mark | Volume (mL) | Density (g/mL) | V/Vo |
| 14.3672 | 22.5 | 26.3 | 5.14 | 1.3358 | 1.0000 |
| 5000 | 24.8 | 25.0 | 5.07 | 1.3542 | 0.9864 |
| 10000 | 25.0 | 24.0 | 5.02 | 1.3677 | 0.9767 |
| 15000 | 25.0 | 23.1 | 4.96 | 1.3843 | 0.9650 |
| 20000 | 25.0 | 22.4 | 4.92 | 1.3955 | 0.9572 |
| 25000 | 25.0 | 21.8 | 4.88 | 1.4070 | 0.9494 |

| Water Content Trial | Content (ppm) | Content (%) |
|---|---|---|
| 1 | 122.1 | 0.01221 |
| 2 | 104.0 | 0.01040 |
| 3 | 112.1 | 0.01121 |
| average | 112.7 | 0.01127 |

Example 10

Density Verse Temperature Profile of Aminopyridinium Compound [mDMAP-Tf$_2$N]

The present example is presented to demonstrate the function of temperature on the density of the aminopyridinium compounds of the invention, and particularly, for [mDMAP-Tf$_2$N].

Figure 8:
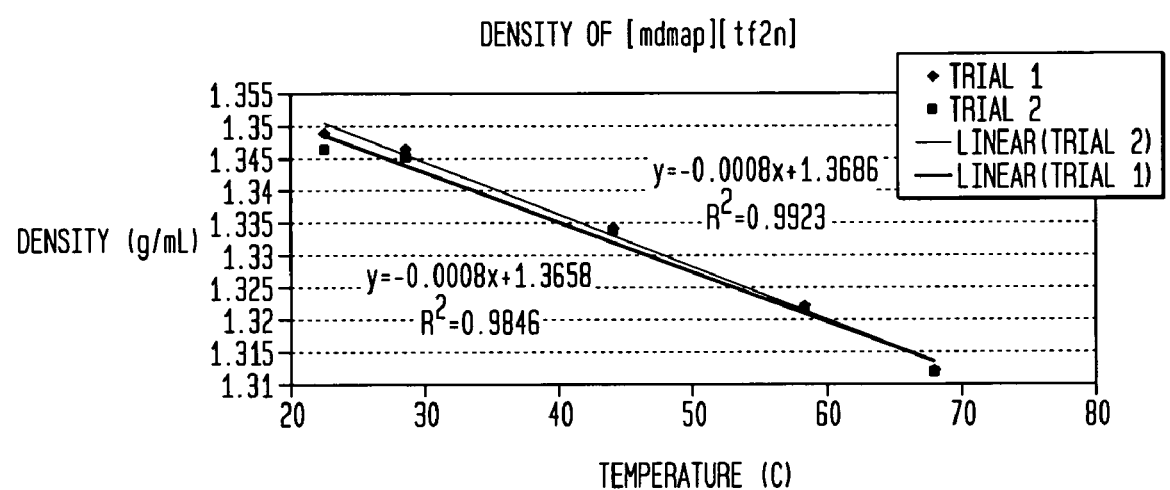
FIG. 8, according to one embodiment of the invention, illustrates the density of [mDMApy][Tf$_2$N]. (trial 1=(♦); trial 2=(■).
Figure 9:
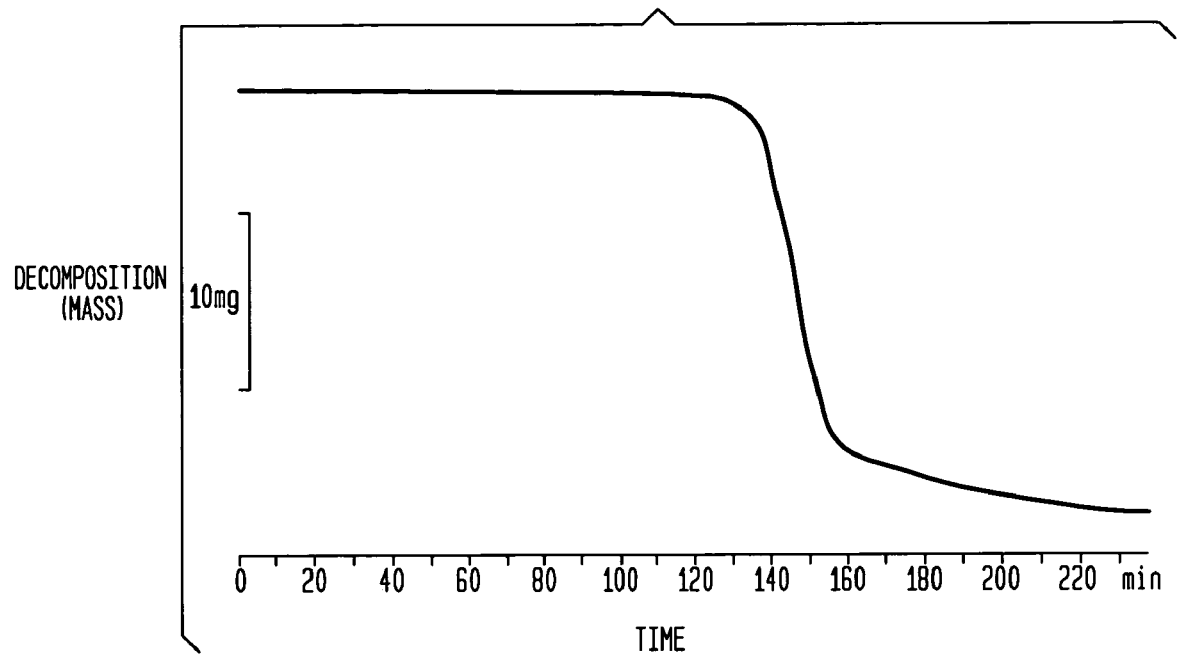
FIG. 9, according to one embodiment of the invention, illustrates a decomposition curve for [bDMApy][dca] under air from 25-500° C. at a rate of 2.0° C./min.
Figure 10:
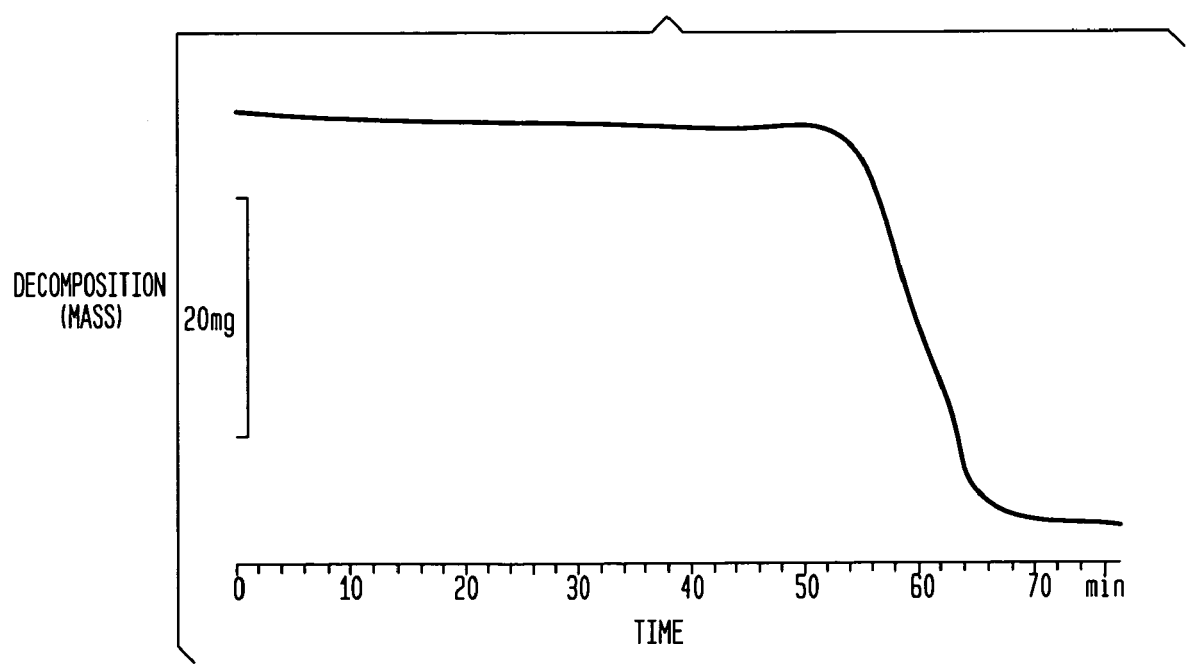
FIG. 10, according to one embodiment of the invention, illustrates a decompensation curve for [bDMApy][Br] under nitrogen from 25-130° C. at a rate of 10.0° C./min.
Figure 11:
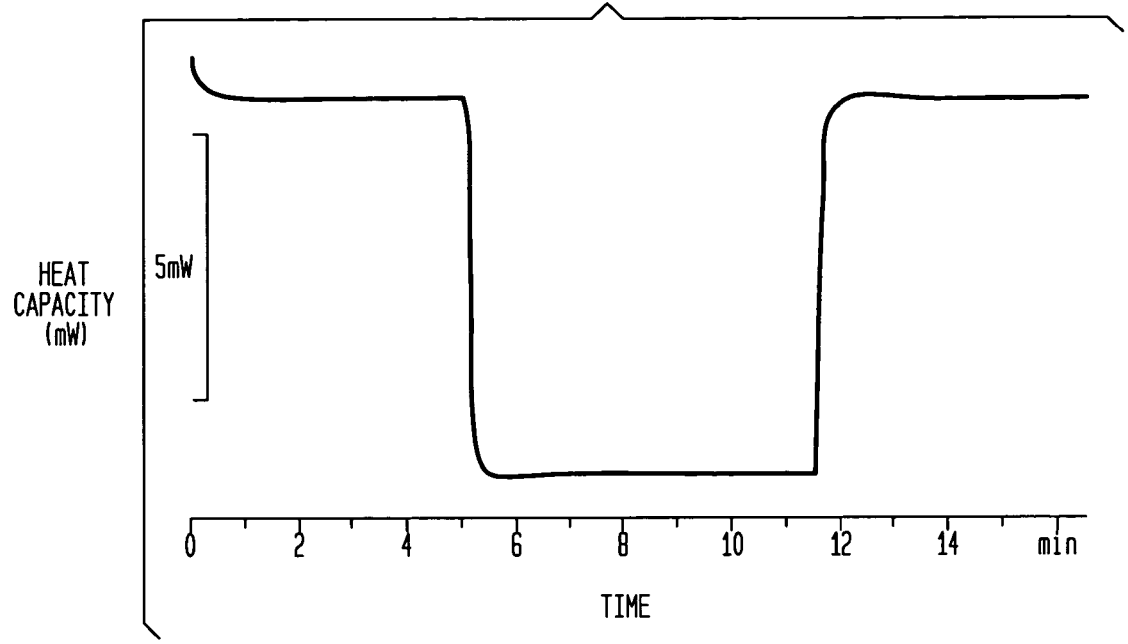
FIG. 11, according to one embodiment of the invention, illustrates a heat capacity curve for [bmDMApy][Br] from 10-75° C. at a rate of 10.0° C./min.
Figure 12:
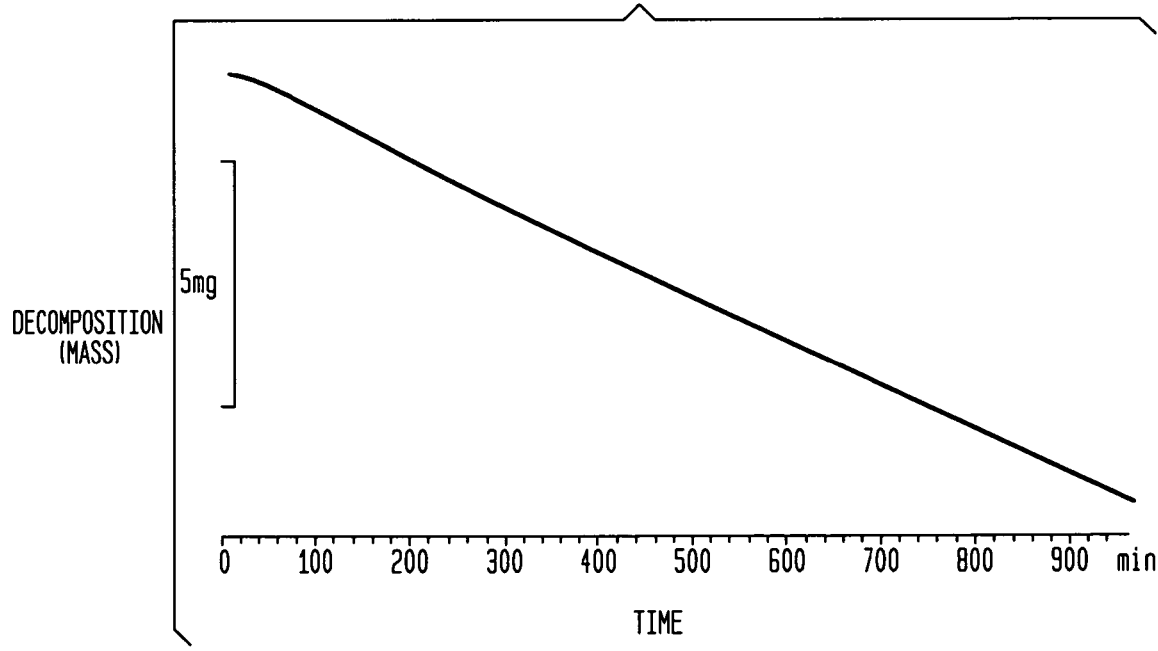
FIG. 12, according to one embodiment of the invention, illustrates a decomposition curve for [hDMApy][Tf$_2$N] at 320° C. for 960 minutes under a nitrogen environment.
Figure 13:
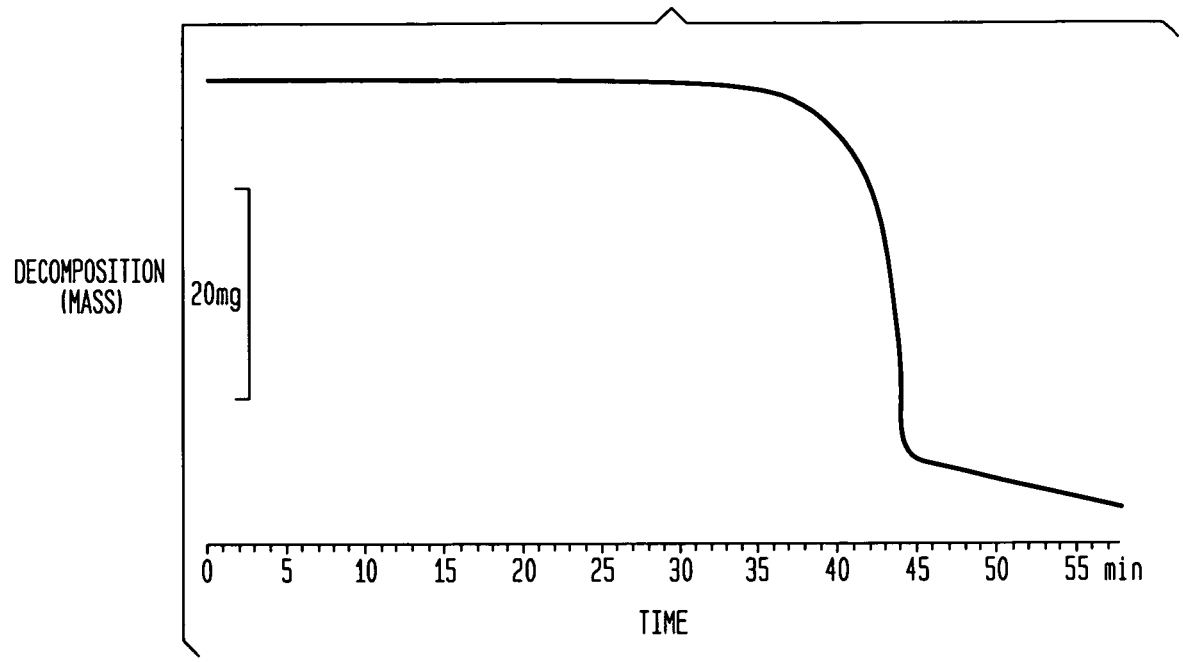
FIG. 13, according to one embodiment of the invention, illustrates a decomposition curve for [hDMApy][Tf$_2$N] under air from 25-600° C. at a rate of 10.0° C./min.
Figure 14:
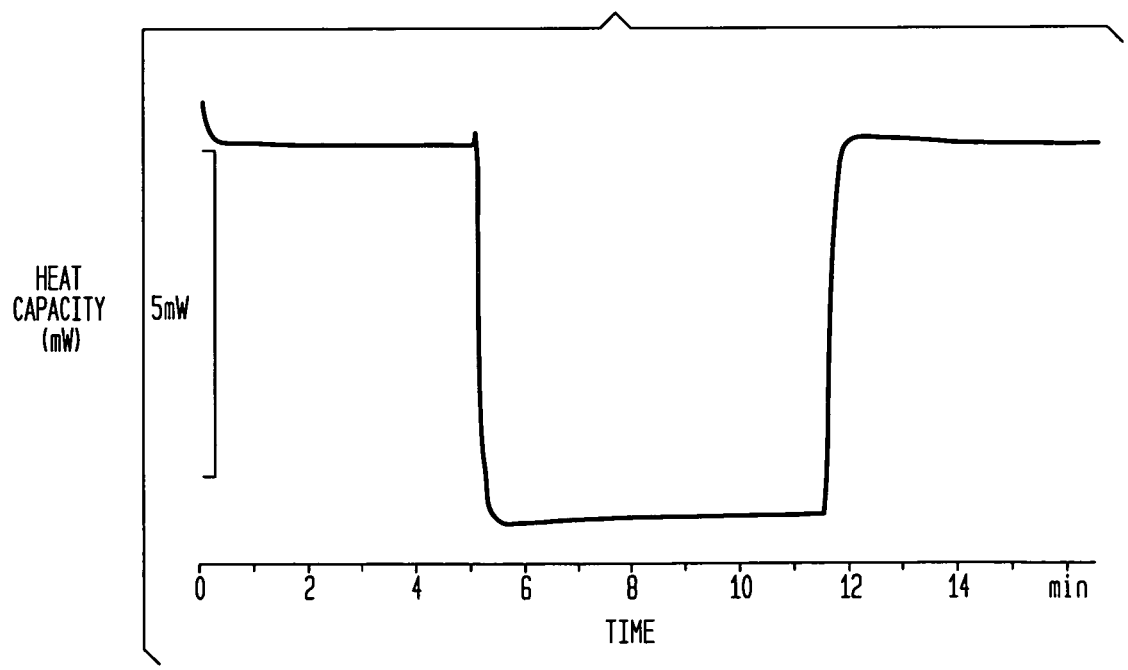
FIG. 14, according to one embodiment of the invention, illustrates a heat capacity curve for [hDMApy][Tf$_2$N] from 10-75° C. at a rate of 10.0° C./min.
Figure 15:
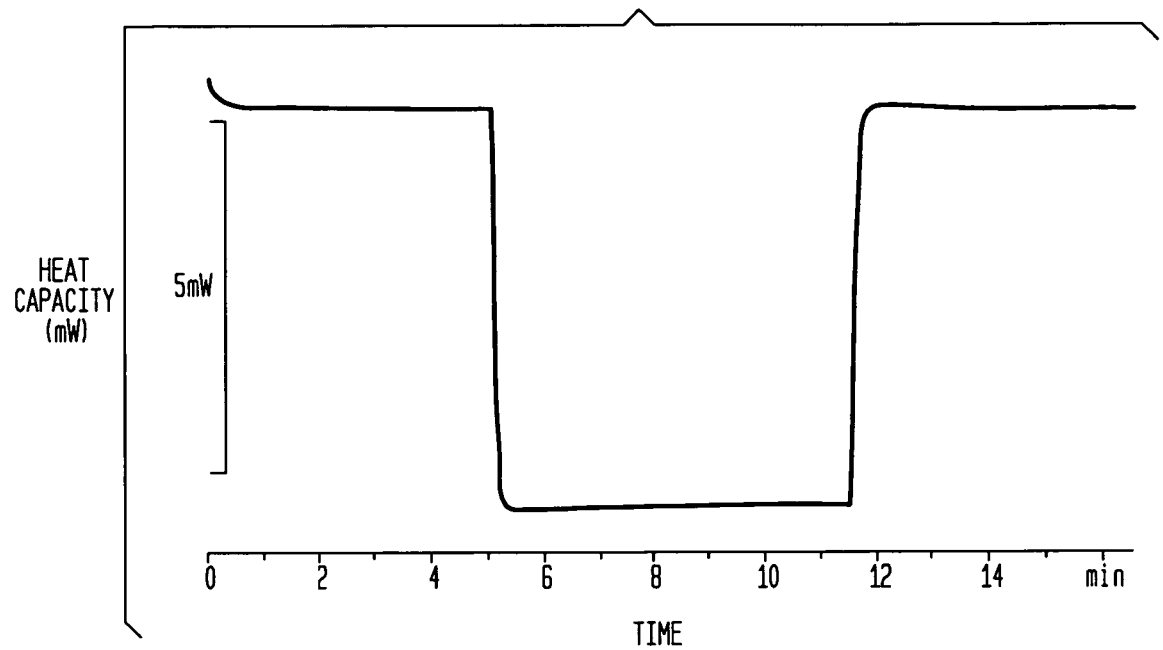
FIG. 15, according to one embodiment of the invention, illustrates a heat capacity curve for [hmDMApy][Tf$_2$N] from 10-75° C. at a rate of 10.0° C./min.
Figure 16:
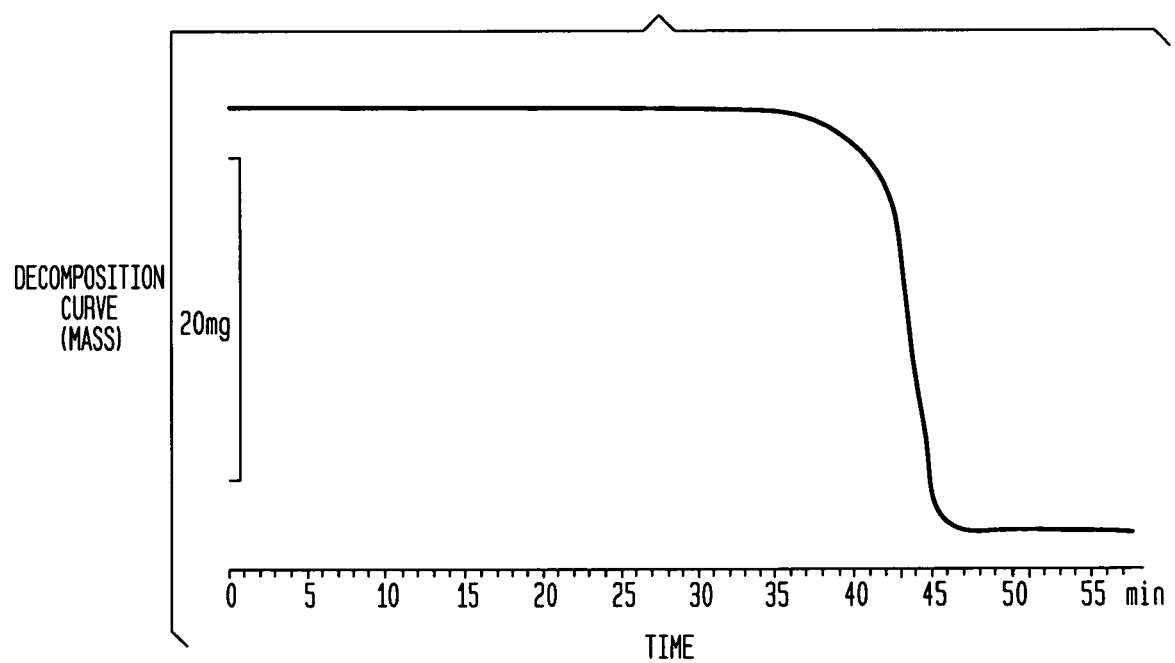
FIG. 16, according to one embodiment of the invention, illustrates graph of the dynamic decomposition curve for [mhDMApy][Tf$_2$N] under air from 25-600° C. at a rate of 10.0° C./min.
Figure 17:
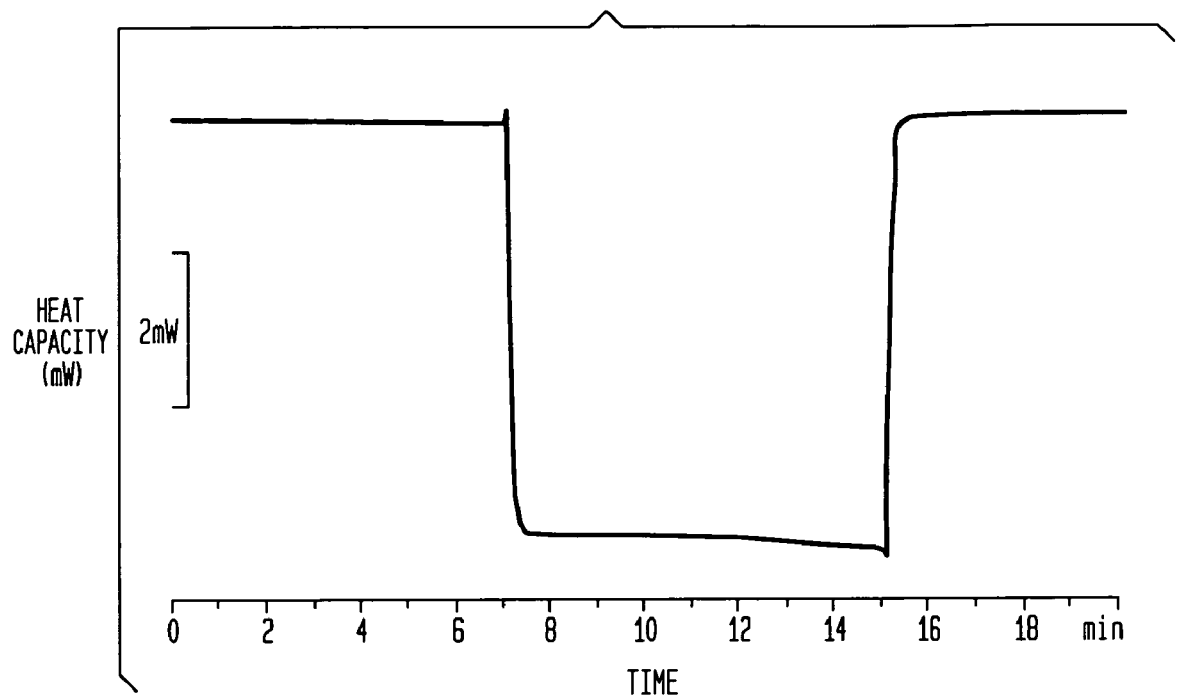
FIG. 17, according to one embodiment of the invention, illustrates a heat capacity curve for [h(mPip)py][Tf$_2$N] from 70-150° C. at a rate of 10.0° C./min.
Figure 18:
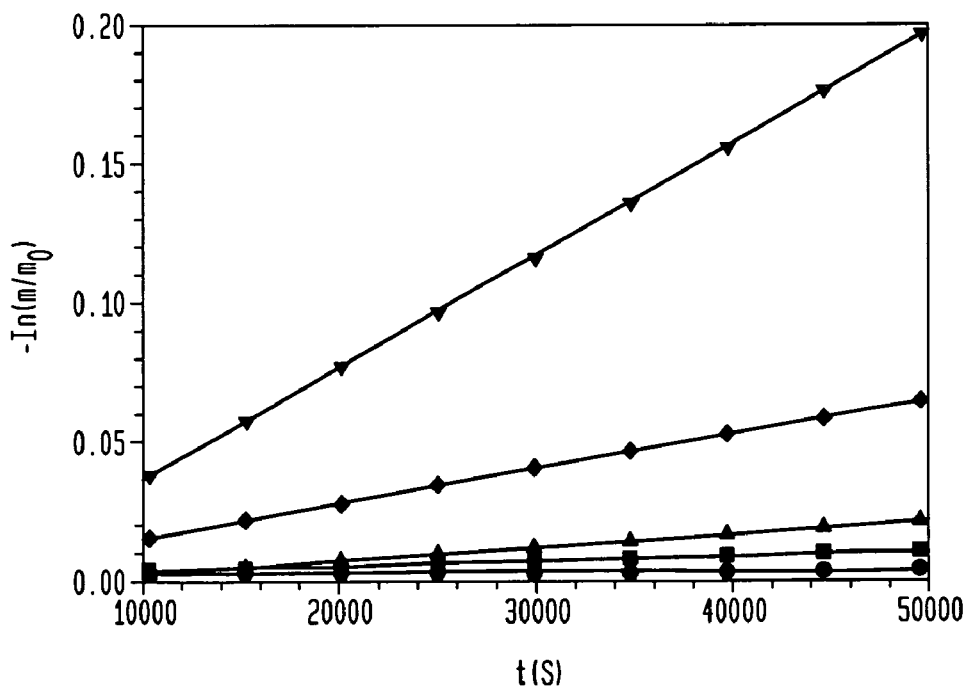
FIG. 18, according to one embodiment of the invention, presents a first order decomposition kinetic diagram for [hDMApy][Tf$_2$N] under a nitrogen environment (●=240° C.; ■=260° C.; ▲=280° C.; ♦=300° C.; ▼=320° C.).
Figure 19:
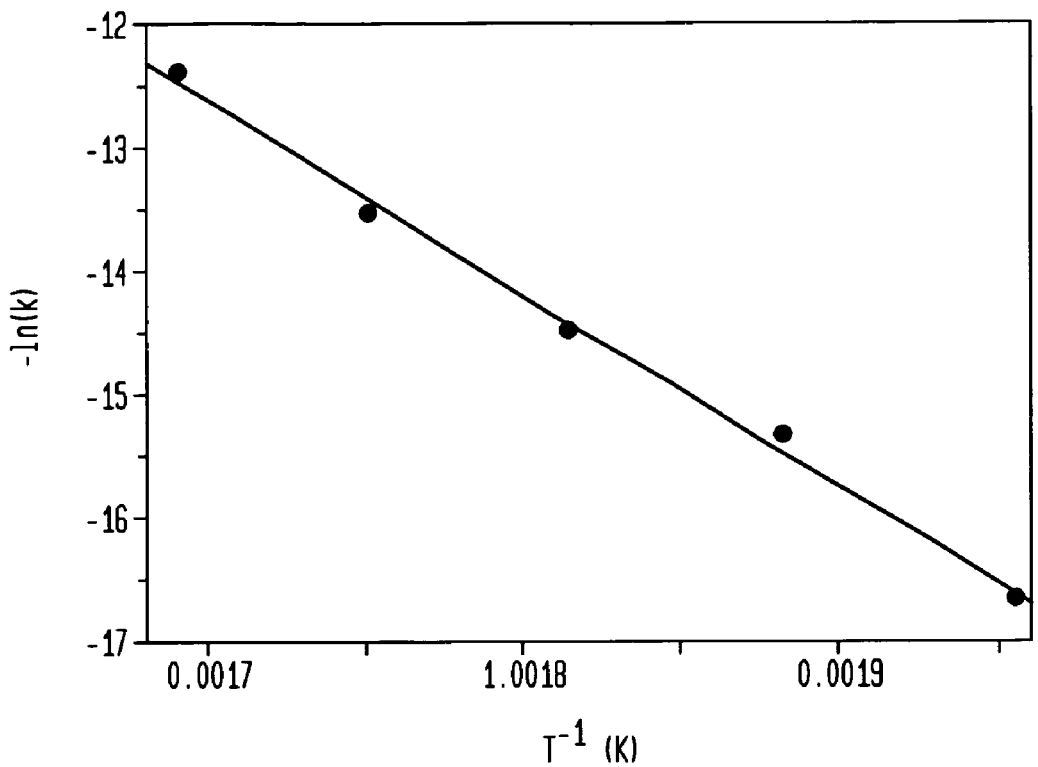
FIG. 19, according to one embodiment of the invention, presents a graph demonstrating the temperature dependence of the decomposition rate for [hDMApy][Tf$_2$N] under a nitrogen environment ($R^2$=0.9931) (study data, (●); predicted, (■)).
Figure 20:
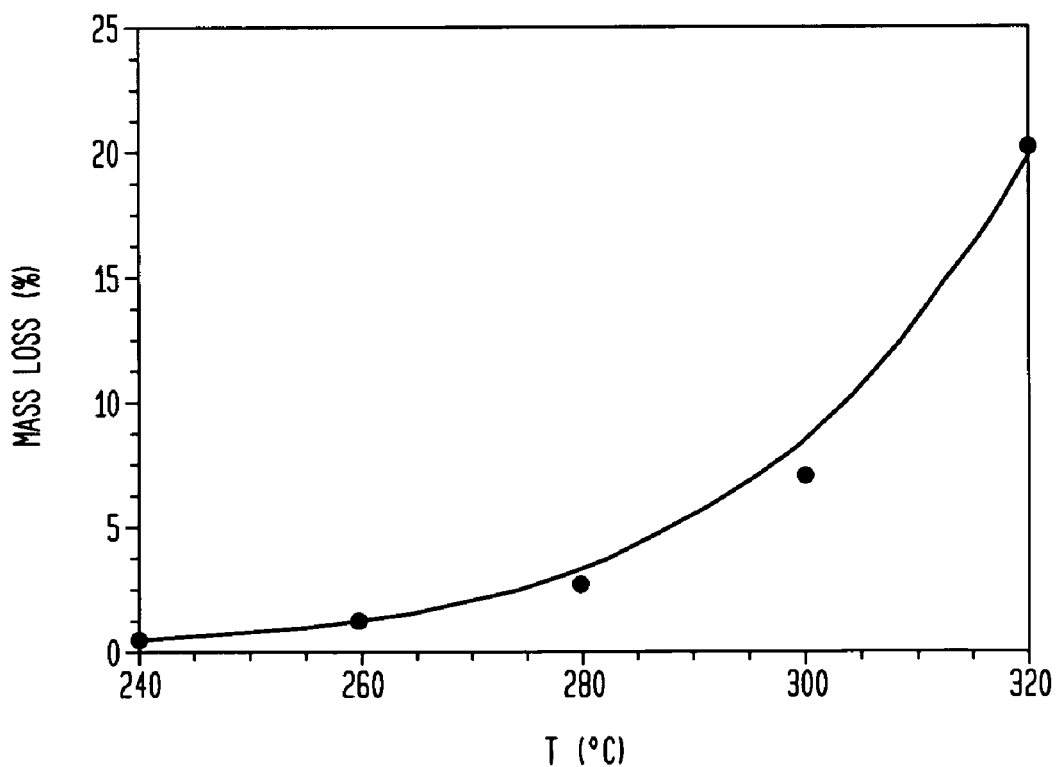
FIG. 20, according to one embodiment of the invention, illustrates the mass loss of [hDMApy][Tf$_2$N] as a function of temperature after 16 hours under a nitrogen environment (study data, (●); predicted, (■)).
Figure 21:
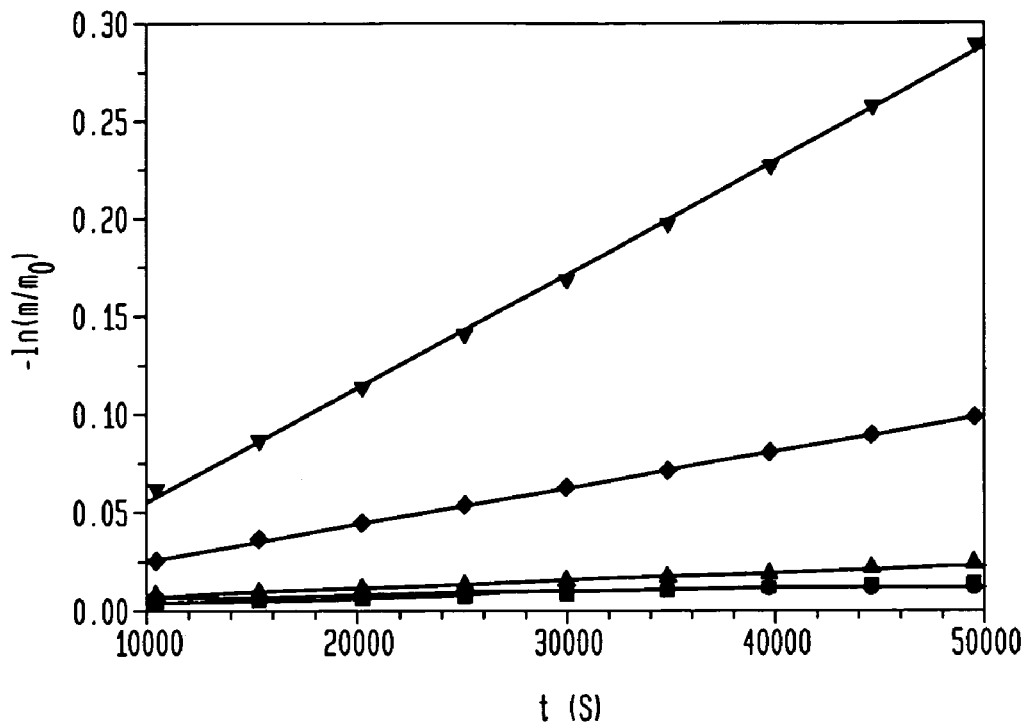
FIG. 21, according to one embodiment of the invention, presents a first order decomposition kinetic diagram for [h(mPip)py][Tf$_2$N] under a nitrogen environment (●=240° C.; ■=260° C.; ▲=280° C.; ♦=300° C.; ▼=320° C.).
Figure 22:
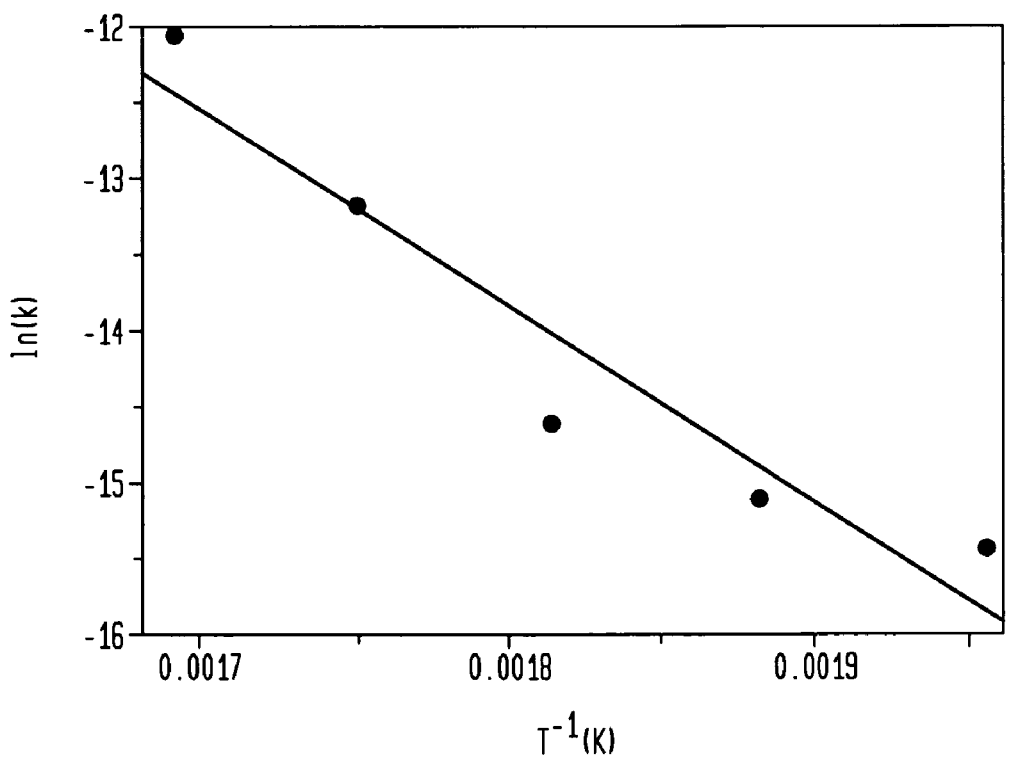
FIG. 22, according to one embodiment of the invention, illustrates the temperature dependence of the decomposition rate for [h(mPip)py][Tf$_2$N] under a nitrogen environment ($R^2$=0.9110) (study data, (●); predicted, (■).
Figure 23:
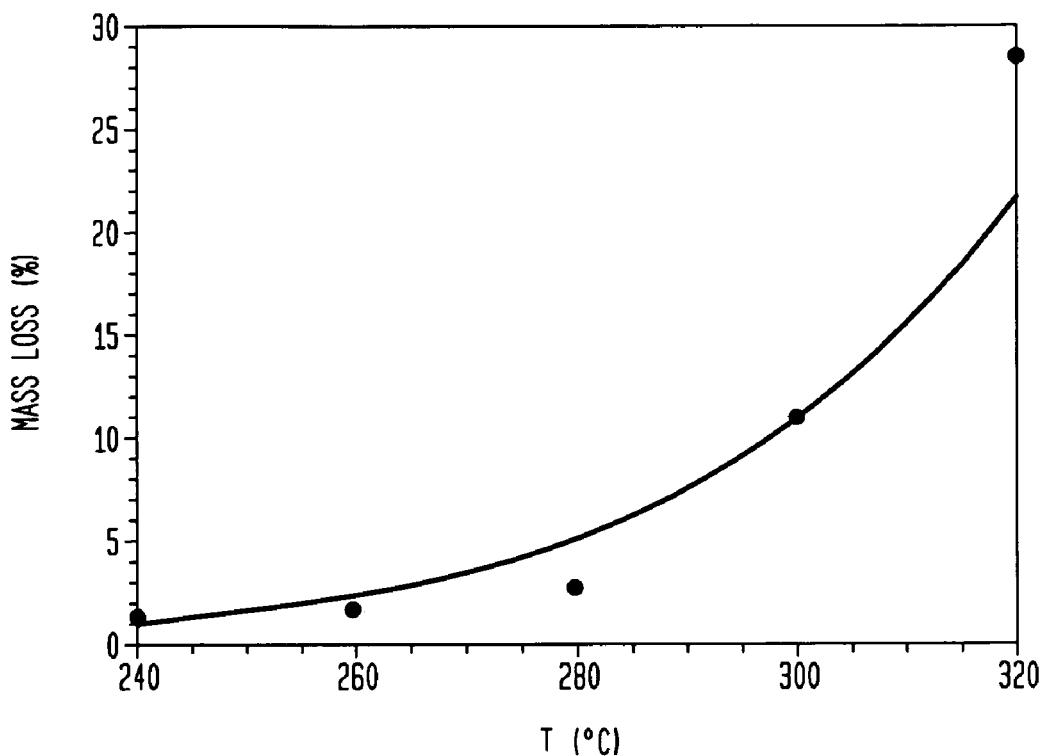
FIG. 23, according to one embodiment of the invention, illustrates the mass loss of [h(mPip)py][Tf$_2$N] as a function of temperature after 16 hours under a nitrogen environment (study data, (●); predicted, (■).
Figure 24:
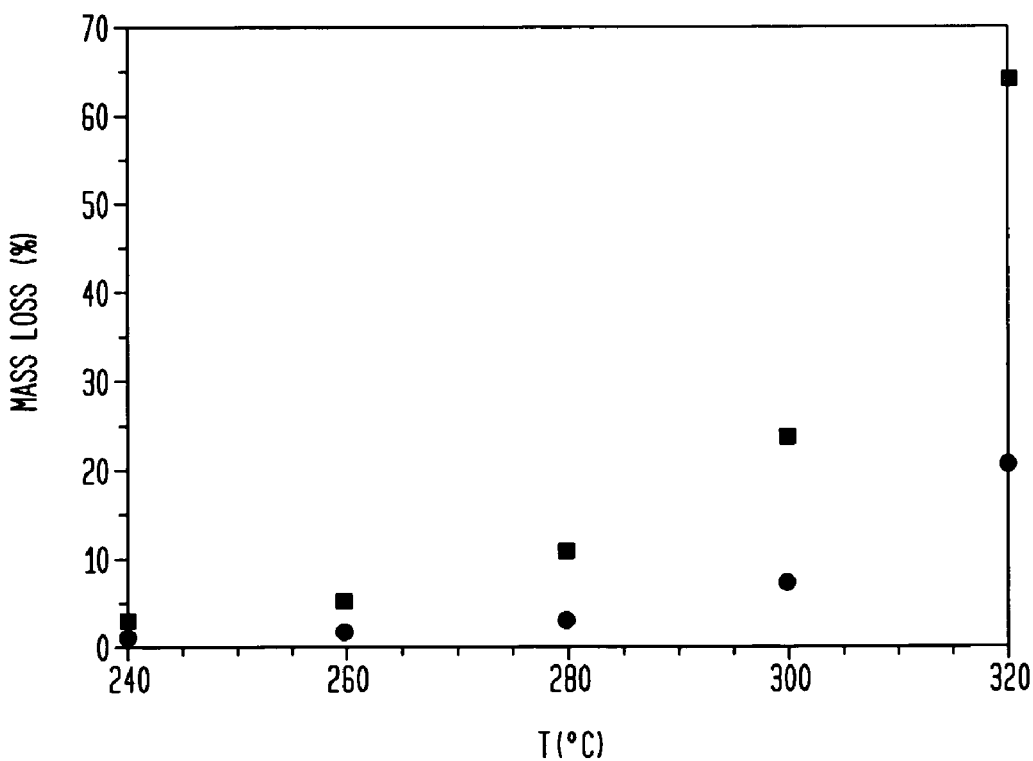
FIG. 24, according to one embodiment of the invention, illustrates the mass loss of [hDMApy][Tf$_2$N] as a function of temperature after 16 hours under a nitrogen (●) and air (■) environment.
Figure 25:
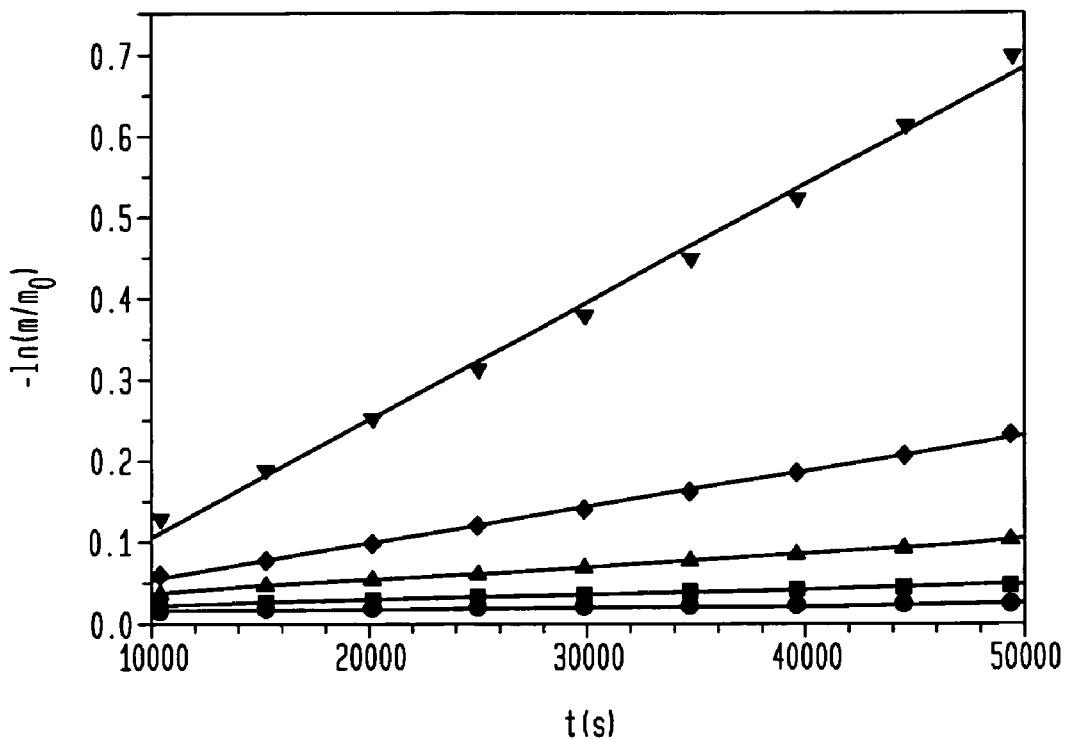
FIG. 25, according to one embodiment of the invention, presents a first order decomposition kinetic diagram for [hDMApy][Tf$_2$N] under an air environment (●=240° C.; ■=260° C.; ▲=280° C.; ♦=300° C.; ▼=320° C.).
Figure 26:
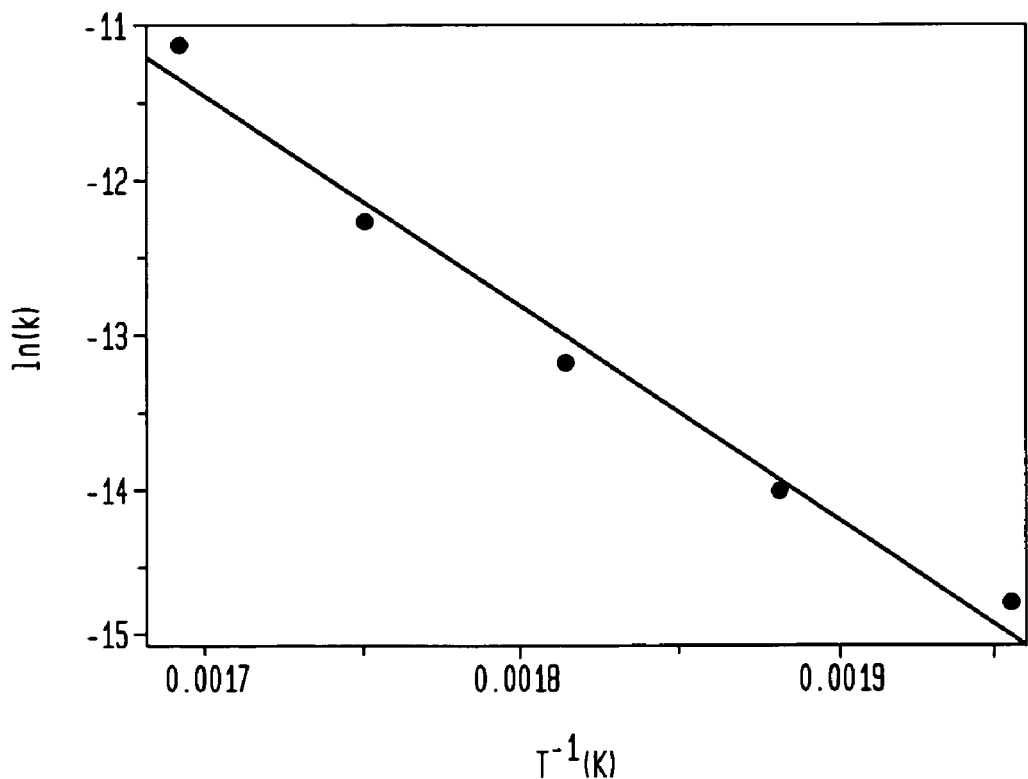
FIG. 26, according to one embodiment of the invention, illustrates the temperature dependence of the decomposition rate for [hDMApy] [Tf$_2$N] under an air environment ($R_2$=0.9833) (study data, (●); predicted, (■)).
Figure 27:
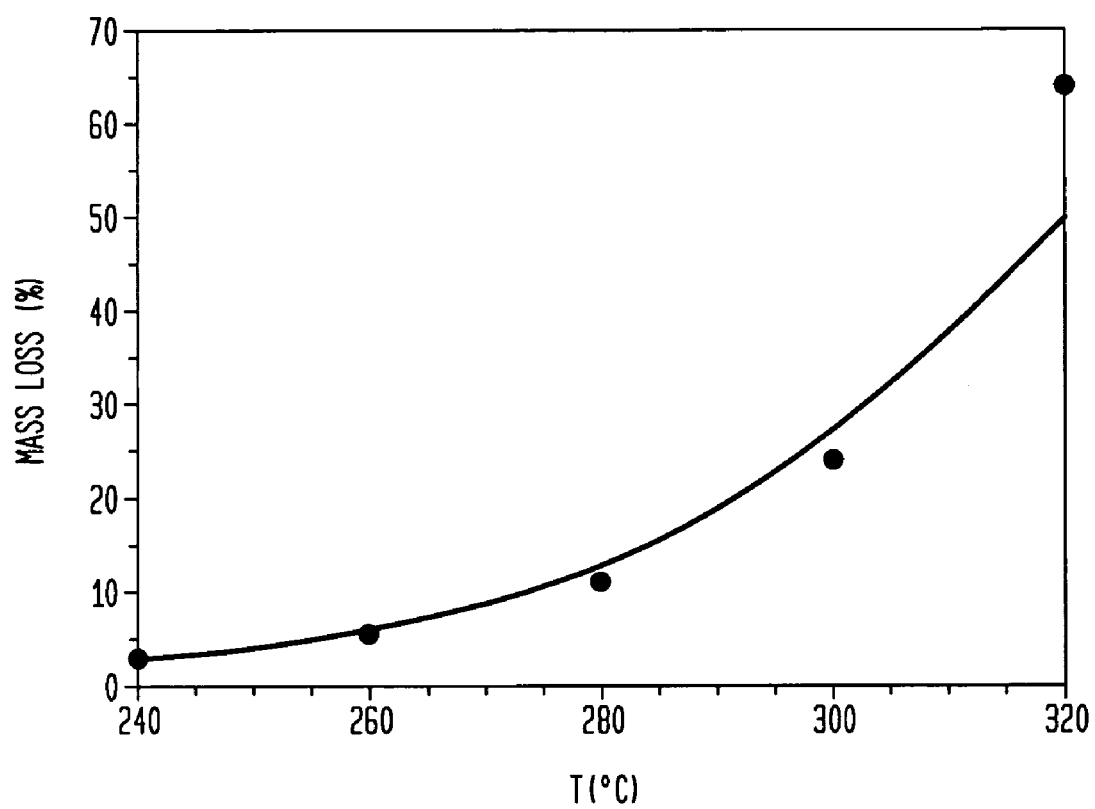
FIG. 27, according to one embodiment of the invention, illustrates the mass loss of [hDMApy][Tf$_2$N] as a function of temperature after 16 hours under an air environment (study data, (●); predicted, (■).
Figure 28:
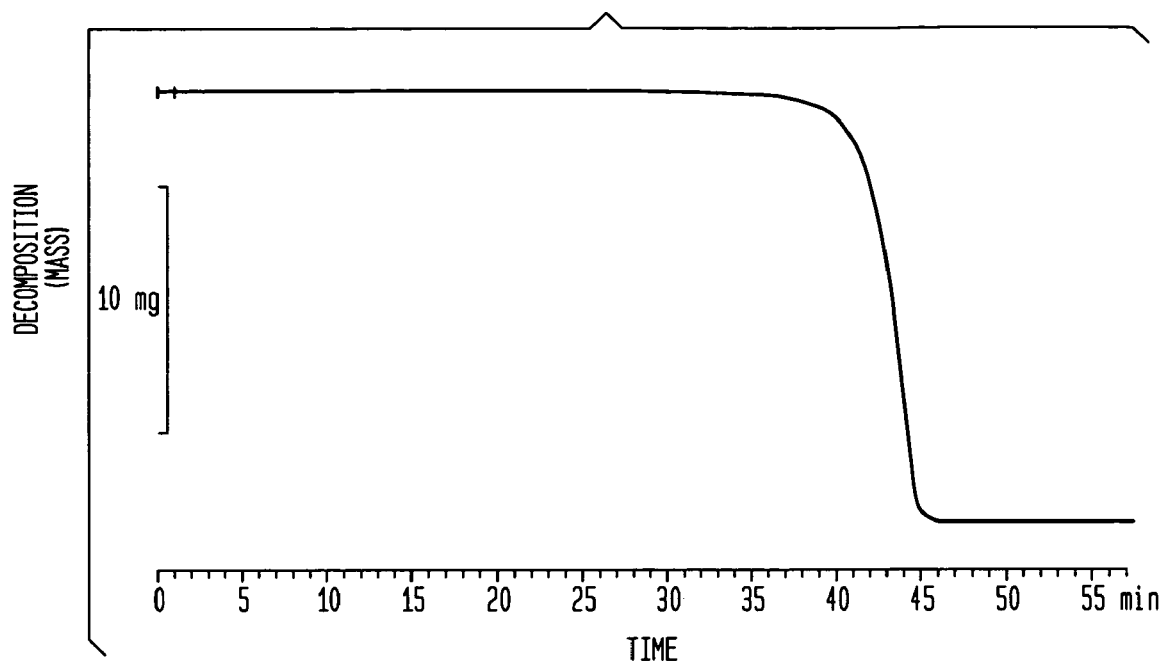
FIG. 28, according to one embodiment of the invention, depicts a dynamic decomposition curve of [h(mPip)py][Tf$_2$N] under nitrogen from 25-600° C. at a rate of 10.0° C./min.

The results of the study are presented in FIG. 8 (Trial 1—y=−0.0008x=1.3658, R20.9846; Trial 2—y=−0.0008x=1.3686, R20.9923).

The tabulated results for Trial 1 and Trial 2 appear in Table 27.

TABLE 27

| | | | mdmap-tf$_2$n | | | | | | | |
|---|---|---|---|---|---|---|---|---|---|---|
| Temperature | Temperature | Pressure | Mass Full (g) | | Mass Sample (g) | | Density (g/mL) | Density | | |
| (C.) | (K) | (mm hg) | 242 | 455 | 242 | 455 | 242 | average | | |
| 22.5 | 295.65 | 742.5 | 4.4648 | 4.1121 | 1.4075 | 1.3296 | 1.3488 | 1.3476 | 242 | 455 |
| 28.6 | 301.75 | 742.5 | 4.4622 | 4.1110 | 1.4049 | 1.3285 | 1.3463 | 1.3458 Wt Empty | 3.0573 | 2.7825 |
| 44.1 | 317.25 | 742.5 | 4.4495 | 4.0998 | 1.3922 | 1.3173 | 1.3342 | 1.3340 Volume | 1.0435 | 0.9876 |
| 58.4 | 331.55 | 742.5 | 4.4371 | 4.0879 | 1.3798 | 1.3054 | 1.3223 | 1.3220 | | |
| 68 | 341.15 | 742.5 | 4.4266 | 4.0782 | 1.3693 | 1.2957 | 1.3122 | 1.3121 | | |

Example 11

Comparative Studies on Phase Transitions and Decomposition Temperatures, Heat Capacitates and Viscosities of Pyridinium Ionic Liquids and Other Compounds The present example presents comparative melting temperatures, glass transition temperatures, decomposition temperatures, heat capacities, and viscosities for a large series of pyridinium-based ionic liquids. For comparison, data for several imidazolium and quaternary ammonium salts included.

Many of the compounds do not crystallize, but form glasses at temperatures between 188 K and 223 K. The thermal stability is largely determined by the coordinating ability of the anion, with ionic liquids made with the least coordinating anions, like bis(trifluoromethylsulfonyl)imide, having the best thermal stability. In particular, dimethylaminopyridinium bis(trifluoromethylsulfonyl)imide salts have some of the best thermal stabilities of any ionic liquid compounds demonstrated here.

Heat capacities are shown to increase approximately linearly with increasing molar mass, which corresponds with increasing numbers of translational, vibrational, and rotational modes.

In general, ILs are quite viscous compared to conventional organic solvents. Viscosity may be a limiting factor in industrial application of ILs if pumping costs become prohibitive. Of course, in many real systems the IL would be mixed with other liquid components (e.g., diluents, reactions, additives, and other potentially viscosity reducing materials), which would cause the viscosity of the mixture to be much lower. Nonetheless, viscosity of the pure ILs is an important property that can be used in screening and evaluation of ILs. In the present example, it is demonstrated that viscosities generally increase with increasing number and length of alkyl substituents on the cation, with the pyridinium salts typically being slightly more viscous than the equivalent imidazolium compounds.

The melting points ($T_{fus}$) and glass transition temperatures ($T_g$), thermal decomposition temperatures ($T_{decomp}$), heat capacities ($C_{p,m}$) and viscosities ($\eta$) are presented. The $T_{fus}$ and $T_g$ values are important for determining the lower end of the useful operating range where the fluid is a liquid. Since ILs do not evaporate, their potential operating range could extend up to the point where they thermally decompose. Thus, $T_{decomp}$ gives an idea of the upper operating range of the fluids.

Heat capacities are important for evaluating ILs for thermal storage and heat transfer applications. However, they are also important in evaluating ILs as solvents in any application where heat has to be added or removed.

Forty-three different IL compounds were compared. All of the compounds were made by pairing either a pyridinium, imidazolium or quaternary ammonium cation with either a bis(trifluoromethylsulfonyl)imide, ethylsulfate, tetrafluoroborate, bromide, docusate, methylsulfate, or sulfated polyethylene glycol anion. These cations and anions are shown in Table 28:

TABLE 28

Cations:

Pyridinium | Imidazolium | Ammonium

Anions

Bromide
a = [Br]

Bis(trifluoromethylsulfonyl)imide
b = [Tf$_2$N]

Ethylsulfate
c = [EtSO$_4$]

Tetrafluoroborate
d = [Bf$_4$]

Docusate
e = [doc]

2-(2-Methoxy-ethoxy)-ethylsulfate
f = [C$_5$H$_{11}$O$_2$SO$_4$]

TABLE 28-continued

| Methylsulfate | Acetate | Trifluoroacetate |
| --- | --- | --- |
| O⁻−S(=O)(=O)−OCH₃ | H₃C−C(=O)−O⁻ | F₃C−C(=O)−O⁻ |
| g = [MeSO$_4$] | h = [CH$_3$CO$_2$] | i = [CF$_3$CO$_2$] |

All of the different cations are listed in Table 29, where the various "R" groups are specified, along with the abbreviations used for each of the cations.

TABLE 29

| ID | Name | | $R_1$ | $R_2$ | $R_3$ | $R_4$ | $R_5$ |
| --- | --- | --- | --- | --- | --- | --- | --- |
| | | Pyridinium ILs | | | | | |
| 1 | 1-ethylpyridinium | [epy] | $C_2H_5$ | H | H | H | H |
| 2 | 1-ethyl-3-methylpyridinium | [empy] | $C_2H_5$ | H | $CH_3$ | H | H |
| 3 | 1-ethyl-3,5-dimethylpyridinium | [emmpy] | $C_2H_5$ | H | $CH_3$ | H | $CH_3$ |
| 4 | 1-ethyl-nicotinic acid ethyl ester | [Et$_2$Nic] | $C_2H_5$ | H | $CO_2C_2H_5$ | H | H |
| 5 | 1-butylpyridinium | [bpy] | n-$C_4H_9$ | H | H | H | H |
| 6 | 1-butyl-3-methylpyridinium | [bmpy] | n-$C_4H_9$ | H | $CH_3$ | H | H |
| 7 | 1-butyl-3,5-dimethylpyridinium | [bmmpy] | n-$C_4H_9$ | H | $CH_3$ | H | $CH_3$ |
| 8 | 1-butyl-4-(dimethylamino)pyridinium | [bDMApy] | n-$C_4H_9$ | H | H | $N(CH_3)_2$ | H |
| 9 | 1-butyl-3-methyl-4-(dimethylamino)pyridinium | [bmDMApy] | n-$C_4H_9$ | H | $CH_3$ | $N(CH_3)_2$ | H |
| 10 | 1-butyl-nicotinic acid butyl ester | [b$_2$Nic] | n-$C_4H_9$ | H | $CO_2C_4H_9$ | HH | |
| 11 | 1-hexylpyridinium | [hpy] | n-$C_6H_{13}$ | H | H | H | H |
| 12 | 1-hexyl-3-methylpyridinium | [hmpy] | n-$C_6H_{13}$ | H | $CH_3$ | H | H |
| 13 | 1-hexyl-3,5-dimethylpyridinium | [hmmpy] | n-$C_6H_{13}$ | H | $CH_3$ | H | $CH_3$ |
| 14 | 1-hexyl-2-ethyl-3,5-dimethylpyridinium | [hemmpy] | n-$C_6H_{13}$ | $C_2H_5$ | $CH_3$ | H | $CH_3$ |
| 15 | 1-hexyl-2-propyl-3,5-diethylpyridinium | [hpeepy] | n-$C_6H_{13}$ | $C_3H_7$ | $C_2H_5$ | H | $C_2H_5$ |
| 16 | 1-hexyl-4-(dimethylamino)pyridinium | [hDMApy] | n-$C_6H_{13}$ | H | H | $N(CH_3)_2$ | H |
| 17 | 1-hexyl-3-methyl-4-(dimethylamino)pyridinium | [hmDMApy] | n-$C_6H_{13}$ | H | H | $N(CH_3)_2$ | H |
| 18 | 1-hexyl-4-(4-methylpiperidino)pyridinium | [h(mPip)py] | n-$C_6H_{13}$ | H | H | $CH_3$—$C_5H_9N$ | H |
| 19 | 1-octylpyridinium | [opy] | n-$C_8H_{17}$ | H | H | H | H |
| 20 | 1-octyl-3-methylpyridinium | [ompy] | n-$C_8H_{17}$ | H | H | H | H |
| | | Imidazolium ILs | | | | | |
| 21 | 1-ethyl-3-methylimidazolium | [emim] | $C_2H_5$ | H | $CH_3$ | | |
| 22 | 1-butyl-3-methylimidazolium | [bmim] | n-$C_4H_9$ | H | $CH_3$ | | |
| 23 | 1-hexyl-3-methylimidazolium | [hmim] | n-$C_6H_{13}$ | H | $CH_3$ | | |
| 24 | 1-hexyl-2,3-dimethylimidazolium | [hmmim] | n-$C_6H_{13}$ | $CH_3$ | $CH_3$ | | |
| 25 | 1-(3,4,5,6-perfluorohexyl)-3-methylimidazolium | [perfluoro-hmim] | n-$C_2H_4C_4F_9$ | H | $CH_3$ | | |
| 26 | 1-octyl-3-methylimidazolium | [omim] | n-$C_8H_{17}$ | H | $CH_3$ | | |
| | | Ammonium ILs | | | | | |
| 27 | tetrabutylammonium | [N$_{4444}$] | n-$C_4H_9$ | n-$C_4H_9$ | n-$C_4H_9$ | n-$C_4H_9$ | |
| 28 | cocosalky pentaethoxi methylammonium | [ECOENG 500] | $CH_3$ | n-$C_{13}H_{27}$ | $(CH_2)_2O(CH_2)_2OH$ | $(CH_2)_2O(CH_2)_2OH$ | |

Data is presented for the melting temperatures, glass transition temperatures, decomposition temperatures, and heat capacities and viscosities as a function of temperature of a series of pyridinium-based ILs. For comparison, additional imidazolium and quaternary ammonium salts were examined. The influence of the number and length of substituents on the cation, the choice of the anion, and the identity of the cation (pyridinium versus imidazolium or quaternary ammonium) on the above properties is also demonstrated.

Materials and Synthesis

All the ILs except PEG-5 cocomonium methylsulfate (ECOENG 500), 1-butyl-3-methylimidazolium 2-(2-methoxy-ethoxy)-ethylsulfate (ECOENG 41M), tetrabutylammonium docusate (Terrasail) and 1-butyl-3-methylpyridinium bis(trifluoromethylsulfonyl)imide ([bmpy][Tf$_2$N]) were synthesized using standard procedures.[11, 62] Typical synthesis and purification procedures are published work.[63, 64] Impurity levels of halide (Br⁻) and ammonium ions in the ILs synthesized were measured using an Oakton Ion 510 meter with Cole-Parmer Ion Specific Probes (27502-05 for Br⁻, and 27502-03 for NH$_4$⁺). All values were less than 10 ppm for Br⁻ and less than 20 ppm for NH$_4$⁺. ECOENG 500 and ECOENG 41M were obtained from Solvent Innovations, with purities of ≧98%, and were used as received. Tetrabutylammonium docusate (Terrasail) was obtained from Sachem and was used as received. [bmpy][Tf$_2$N] was obtained from Strem Chemicals with a purity of ≧99% and was used as received. All ILs were dried under vacuum for at least 48 h at temperatures between 313 K and 353 K to remove organic solvents and water. For the $T_{fus}$, $T_g$, $T_{decomp}$, and $C_{p,m}$ measurements, the samples were further dried in situ prior to the measurements, if necessary. For the viscosity measurements, the approximate water content, as determined by Karl-Fischer titration or Coulometry (either EM Science Aquastar V-200 or Brinkmann Metrohm 756KF Coulometer), are listed with the results since the viscosities are very sensitive to water content.

Melting Temperature, Glass Transition Temperature, and Heat Capacity Measurements $T_{fus}$, $T_g$ (as well as crystallization temperatures), and $C_{p,m}$ were measured with a Mettler-Toledo differential scanning calorimeter (DSC), model DSC822$^e$, and the data were evaluated using the Mettler-Toledo STAR$^e$ software version 7.01, as described.[63] Samples were dried in situ in the DSC. The presence of volatiles significantly affects glass transition and melting temperatures. Therefore, samples were dried repeatedly until the phase transition temperatures remained constant. While replicate scans and measurements of the $T_{fus}$ of standard samples are all better than ±0.3 K, only the values of the phase transition temperatures to the nearest 1 K is reported, since there may exist slight impurities in the ILs that produce a much greater uncertainty than inherent instrument uncertainty. In addition, results may depend somewhat on the scan rate since ILs are known to remain in metastable liquid states for long periods of time.[62]

The heat capacities of the compounds were determined relative to an α-alumina (sapphire) sample, as described previously.[63] The potential error deviation (potential uncertainty) of these measurements to be on the order of +/−5%.

TABLE 30

Glass transition ($T_g$), cold crystallization ($T_{cc}$), melting ($T_m$), and freezing ($T_{fus}$) temperatures for the ILs defined in Table 29.

| Compound | IL | $T_g$/K | $T_{cc}$/K | $T_m$/K | $T_{fus}$/K |
|---|---|---|---|---|---|
| 2c | [empy][EtSO$_4$] | 202 | | | |
| 4c | [Et$_2$Nic][EtSO$_4$] | 229 | | | |
| 5a | [bpy][Br] | | | 378 | 315 |
| 6a | [bmpy][Br] | 237 | | | |
| 6b | [bmpy][Tf$_2$N] | 189 | | | |
| 6d | [bmpy][BF$_4$] | 197 | | | |
| 7a | [bmmpy][Br] | 249 | 309 | 368 | |
| 8a | [bDMApy][Br] | | | 495 | 433 |
| 10b | [b$_2$Nic][Tf$_2$N] | 215 | 261 | 288 | |
| 11b | [hpy][Tf$_2$N] | 196 | 247 | 273 | |
| 12a | [hmpy][Br] | 236 | | | |
| 12b | [hmpy][Tf$_2$N] | 191 | | | |
| 13b | [hmmpy][Tf$_2$N] | 197 | 249 | 283 | |
| 14b | [hemmpy][Tf$_2$N] | 207 | | | |
| 15b | [hpeepy][Tf$_2$N] | 206 | | | |
| 16a | [hDMApy][Br] | | | 469 | 416 |
| 16b | [hDMApy][Tf$_2$N] | 204 | | | |
| 17a | [hmDMApy][Br] | 271 | 331, 358 | 392 | |
| 17b | [hmDMApy][Tf$_2$N] | 201 | 254 | 271 | |
| 18a | [h(mPip)py][Br] | 306 | | | |
| 18b | [h(mPip)py][Tf$_2$N] | 218 | 249 | 310 | |
| 20b | [ompy][Tf$_2$N] | 193 | | | |
| 22f | ECOENG 41M | 211 | | | |
| 23a | [hmim][Br] | 224 | | | |
| 23b | [hmim][Tf$_2$N] | 189 | 243 | 266 | |
| 23d | [hmim][BF$_4$] | 194 | | | |
| 24b | [hmmim][Tf$_2$N] | 199 | 238 | 268 | |
| 25b | [perfluoro-hmim][Tf$_2$N] | 217 | | | |
| 26b | [omim][Tf$_2$N] | 189 | | | |
| 26d | [omim][BF$_4$] | 192 | | | |
| 27e | [N$_{4444}$][doc] | 211 | | | |
| 28g | ECOENG 500 | 206, 228 | | | |

Decomposition Temperatures

The decomposition temperatures were measured with a Mettler Toledo TGA/SDTA 851e/SF/1100° C. thermal gravimetric analyzer, using a nitrogen atmosphere. The onset and the start temperature for the decomposition is reported here. These were determined by the Mettler Toledo STAR$^e$ Version 7.01 software. The onset temperature ($T_{onset}$) is the intersection of the baseline weight, either from the beginning of the study or after the drying step, and the tangent of the weight vs. temperature curve as decomposition occurs. The decomposition of the sample begins at the start temperature ($T_{start}$). The samples were run in aluminum pans under a nitrogen atmosphere at a heating rate of 0.17 K·s$^{-1}$. When weight loss was observed from the evaporation of water from the sample, it was further dried in situ at 403 K for 0.5 h. Reproducibility was verified by running three replicates for each ionic liquid. The largest uncertainty is from manually determining the tangent point for the onset temperature, which results in an uncertainty in the thermal decomposition temperatures of ±2 K. However, the uncertainty in the replicates for each ionic liquid is about an order of magnitude less than this uncertainty.

Viscosity Measurements

Viscosity measurements were performed with a Brookfield model DV-III Ultra Programmable (Cone and Plate) Rheometer. This instrument reproduces the literature value of the viscosity of [omim][Tf$_2$N][64] to within 2% and has an accuracy of approximately ±2%. The dried IL sample is loaded into the sample chamber, which is purged with dry nitrogen to prevent the uptake of water from the atmosphere. The sample is then maintained at the desired temperature for between 0.17 h and 1 h to ensure thermal equilibrium of the sample before a measurement is obtained. Repetition of the measurement of a particular sample at a particular temperature after the sample had been in the instrument for as much as 14 h yielded reproducible values within 2%. The uncertainty in the temperature on the instrument is ±0.25 K.

Melting Temperature, Crystallization and Glass Transition Temperatures

The melting, crystallization, and glass transition temperatures were measured by differential scanning calorimetry. The values of melting temperature ($T_{fus}$), glass transition temperature ($T_g$), and cold crystallization temperature ($T_{cc}$), where appropriate, are shown for all the compounds investigated in Table 30. The melting point is the onset of an endothermic peak on heating. The glass transition temperature is the midpoint of a small heat capacity change on heating from the amorphous glass state to a liquid state. The cold crystallization temperature is the onset of an exothermic peak on heating from a subcooled liquid state to a crystalline solid state, which has been observed previously for ILs[63], as well as polymers and other amorphous materials.

The compounds investigated fell into one of three categories. Many simply form a glass at low temperatures. They exhibit no freezing or melting transitions. Even a variety of the bromide salts, which tend to have freezing and melting points above room temperatures, are liquid when paired with many pyridinium cations, forming glasses at temperatures between 233 K and 253 K. The second class crystallizes upon cooling and melts upon heating. This behavior is only observed for three pyridinium bromides, [bpy][Br], [bDMApy][Br], and [hDMApy][Br]. The cations that have melting and freezing points are symmetric, which may aid in crystal formation. The third class of compounds remain liquid upon cooling until they reach a glass transition temperature at a very low temperature (e.g., 197 K for [hmmpy][Tf$_2$N]). However, upon heating above $T_g$, the liquid forms a crystalline solid, as indicated by the onset of an exothermic peak on heating at $T_{cc}$. Finally, the solid melts at $T_{fus}$. For instance, [hpy][Tf$_2$N], [hmmpy][Tf$_2$N] and [hmDMApy][Tf$_2$N] all fall into this category.

Decomposition Temperatures

Decomposition temperatures are listed in Table 31, where both the temperature of decomposition onset ($T_{onset}$), as defined herein, and the first temperature where any measurable weight loss whatsoever ($T_{start}$), is reported (measurements are presented as "K" (Kelvin), conversion from Celsius is °C.+273=K). Both of these numbers are referred to collectively as the decomposition temperature ($T_{decomp}$). The decomposition temperatures depend primarily on the coordinating nature of the anion, with the $T_{decomp}$ being much lower for the highly coordinating halide anions. Decomposition temperatures are highest for the poorly coordinating bis(trifluoromethylsulfonyl)imide anion, with others falling between these two extremes.

TABLE 31

Onset ($T_{onset}$) and start ($T_{start}$) of the thermal decomposition temperature for ILs defined in Table 29.

| Compound | IL | $T_{onset}$/K | $T_{start}$/K |
|---|---|---|---|
| 1c | [epy][EtSO$_4$] | 576 | 483 |
| 2c | [empy][EtSO$_4$] | 554 | 486 |
| 3c | [emmpy][EtSO$_4$] | 570 | 482 |
| 4c | [Et$_2$Nic][EtSO$_4$] | 526 | 458 |
| 5a | [bpy][Br] | 510 | 467 |
| 6a | [bmpy][Br] | 508 | 472 |
| 6b | [bmpy][Tf$_2$N] | 670 | 590 |
| 6d | [bmpy][BF$_4$] | 637 | 506 |
| 7a | [bmmpy][Br] | 512 | 471 |
| 8a | [bDMApy][Br] | 564 | 526 |
| 9a | [bmDMApy][Br] | 543 | 498 |
| 10b | [b$_2$Nic][Tf$_2$N] | 592 | 569 |
| 11a | [hpy][Br] | 511 | 468 |
| 11b | [hpy][Tf$_2$N] | 665 | 605 |
| 12a | [hmpy][Br] | 510 | 472 |
| 12b | [hmpy][Tf$_2$N] | 672 | 603 |
| 13a | [hmmpy][Br] | 512 | 474 |
| 13b | [hmmpy][Tf$_2$N] | 678 | 613 |
| 14b | [hemmpy][Tf$_2$N] | 657 | 601 |
| 15b | [hpeepy][Tf$_2$N] | 654 | 598 |
| 16a | [hDMApy][Br] | 561 | 525 |
| 16b | [hDMApy][Tf$_2$N] | 716 | 649 |
| 17a | [hmDMApy][Br] | 548 | 505 |
| 17b | [hmDMApy][Tf$_2$N] | 717 | 631 |
| 18a | [h(mPip)py][Br] | 557 | 517 |
| 18b | [h(mPip)py][Tf$_2$N] | 720 | 640 |
| 19a | [opy][Br] | 509 | 460 |
| 20a | [ompy][Br] | 506 | 459 |
| 20b | [ompy][Tf$_2$N] | 667 | 605 |
| 20d | [ompy][BF$_4$] | 647 | 547 |
| 22f | ECOENG 41M | 363 | 357 |
| 22h | [bmim][CH$_3$CO$_2$] | 493 | 446 |
| 22i | [bmim][CF$_3$CO$_2$] | 443 | 415 |
| 23a | [hmim][Br] | 549 | 492 |
| 23b | [hmim][Tf$_2$N] | 700 | 620 |
| 23d | [hmim][BF$_4$] | 631 | 556 |
| 24b | [hmmim][Tf$_2$N] | 710 | 633 |
| 25b | [perfluoro-hmim][Tf$_2$N] | 686 | 588 |
| 26a | [omim][Br] | 551 | 492 |
| 26b | [omim][Tf$_2$N] | 700 | 618 |
| 26d | [omim][BF4] | 644 | 555 |
| 27e | [N$_{4444}$][doc] | 554 | 486 |
| 28g | ECOENG 500 | 488 | 429 |

Figure 29:
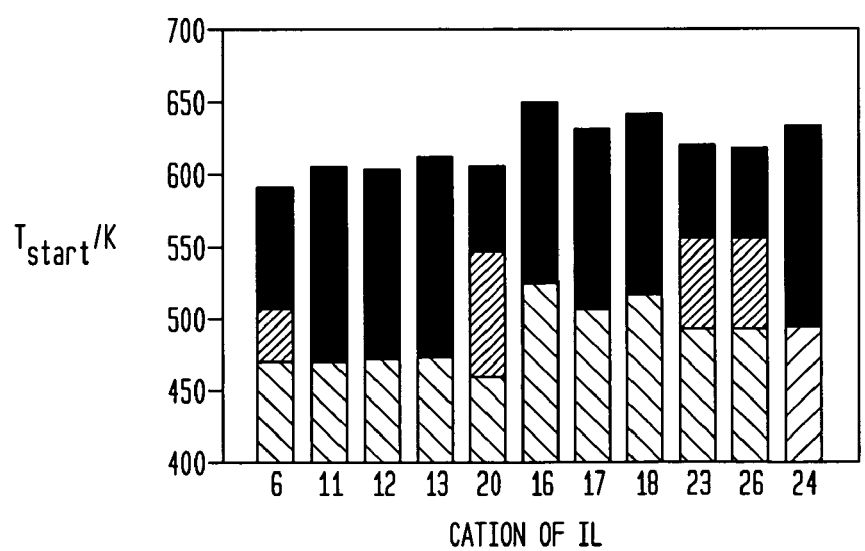
FIG. 29, according to one embodiment of the invention, presents a comparison of the decomposition temperatures, as determined by $T_{start}$: ▤, [Br]; ▧, [BF$_4$]; and ■[Tf$_2$N].

The nature of the cation has a small effect on $T_{decomp}$. This is shown in FIG. 29, where $T_{start}$ is plotted for a series of different pyridinium and imidazolium cations for bromide and [Tf$_2$N] anions, as well as [BF$_4$] anions, where available. There is little difference in the decomposition temperature with regards to alkyl chain length on the cation (e.g., [bmpy] vs. [hmpy] vs. [ompy]). The compounds with the best thermal stability are those containing amino groups in the 4 position of the ring. The dimethylamino or piperidino groups should serve to spread the charge more evenly around the cation ring. This apparently lends some degree of increased thermal stability, making these compounds particularly attractive for high temperature applications. Notice from Table 31 and FIG. 29, that for equivalent imidazolium and pyridinium compounds (e.g., [omim][Tf$_2$N] vs. [ompy][Tf$_2$N]), the imidazolium compounds appear to have slightly better thermal stability. Also note that some additional stability can be obtained by blocking the acidic hydrogen in the 2 position on the imidazolium ring with a methyl group (i.e., [hmim][Tf$_2$N] vs. [hmmim][Tf$_2$N]).

Heat Capacities

The heat capacities of the various ILs were measured over a temperature range of 298 K to 338 K. The values at 298 K and 323 K are shown in Table 32 and linear correlations of $C_{p,m}$ as a function of temperature are shown in Table 33, along with the standard deviations for the fit. In general, the uncertainty in these measurements is estimated to be approximately ±5%.

Figure 30:
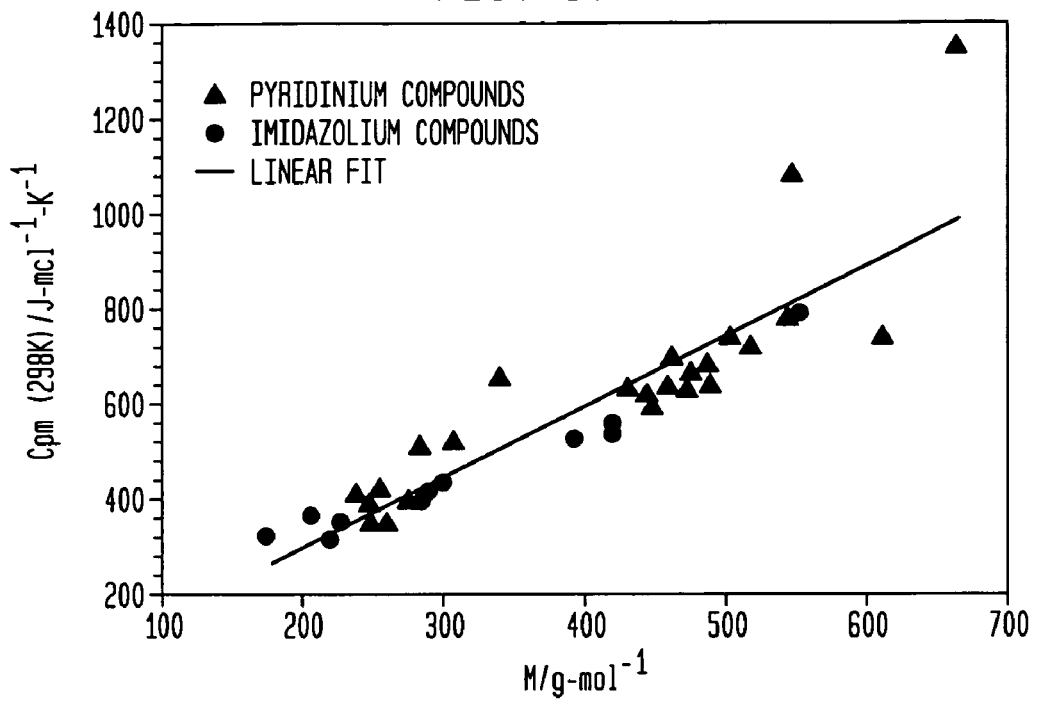
FIG. 30, according to one embodiment of the invention, presents the ionic liquid heat capacities ($C_{p,m}$) as a function of the molar mass (M) (▲, Pyridinium compounds; ●, Imidazolium compounds; and ■, linear fit).

A plot of the heat capacity at a particular temperature (e.g., 298 K) as a function of molar mass was prepared. This is shown in FIG. 30 for the compounds measured here, as well as other imidazolium salts. The heat capacity increased linearly with increased molar mass. Since heat capacity depends on the number of translational, vibrational, and rotational energy storage modes, increasing $C_{p,m}$ with increasing molar mass makes sense for these compounds that are comprised of a limited number of different atoms.

TABLE 32

Heat capacities ($C_{p,m}$) at temperatures of (298 and 323) K for the ILs defined in Table 29.

| Compound | IL | $C_{p,m}$ (298 K)/ J·mol$^{-1}$·K$^{-1}$ | $C_{p,m}$ (323 K)/ J·mol$^{-1}$·K$^{-1}$ |
|---|---|---|---|
| 2c | [empy][EtSO$_4$] | 389 | 402 |
| 4c | [Et$_2$Nic][EtSO$_4$] | 513 | 530 |
| 6b* | [bmpy][Tf$_2$N] | 622 | 641 |
| 6d* | [bmpy][BF$_4$] | 405 | 421 |
| 10b* | [b$_2$Nic][Tf$_2$N] | 707 | 727 |
| 11b | [hpy][Tf$_2$N] | 612 | 632 |
| 12a | [hmpy][Br] | 343 | 358 |
| 12b* | [hmpy][Tf$_2$N] | 624 | 644 |
| 13b* | [hmmpy][Tf$_2$N] | 620 | 665 |
| 15b | [hpeepy][Tf$_2$N] | 766 | 799 |
| 16b | [hDMApy][Tf$_2$N] | 628 | 650 |
| 17b* | [hmDMApy][Tf$_2$N] | 725 | 764 |
| 20b | [ompy][Tf$_2$N] | 669 | 693 |
| 22f | ECOENG 41M | 643 | 652 |
| 23a | [hmim][Br] | 344 | 357 |
| 23b* | [hmim][Tf$_2$N] | 583 | 604 |
| 23d | [hmim][BF$_4$] | 416 | 433 |
| 24b | [hmmim][Tf$_2$N] | 686 | 705 |
| 25b* | [perfluoro-hmim][Tf$_2$N] | 725 | 752 |
| 26a | [omim][Br] | 392 | 408 |
| 26b | [omim][Tf$_2$N] | 654 | 677 |
| 26d | [omim][BF$_4$] | 506 | 526 |
| 27e | [N$_{444}$][doc] | 1325 | 1385 |
| 28g | ECOENG 500 | 1066 | 1098 |

*indicates that the data was averaged from two or more separate runs.

TABLE 33

Correlating equation (A · T + B) for the heat capacities ($C_{p,m}$) as a function of temperature between (298 and 338) K, with standard deviation (σ), for the ILs defined in Table 1.

| Compound | IL | Correlation for $C_{p,m}$/ J·mol$^{-1}$·K$^{-1}$ | δ/J · mol$^{-1}$·K$^{-1}$ |
|---|---|---|---|
| 2c | [empy][EtSO$_4$] | 0.433(T/K) + 261.025 | 0.74 |
| 4c | [Et$_2$Nic][EtSO$_4$] | 0.585(T/K) + 340.148 | 0.99 |
| 6b* | [bmpy][Tf$_2$N] | 0.609(T/K) + 443.111 | 1.43 |

TABLE 33-continued

Correlating equation (A · T + B) for the heat capacities ($C_{p,m}$) as a function of temperature between (298 and 338) K, with standard deviation (σ), for the ILs defined in Table 1.

| Compound | IL | Correlation for $C_{p,m}$/ J·mol⁻¹·K⁻¹ | δ/J·mol⁻¹·K⁻¹ |
|---|---|---|---|
| 6d* | [bmpy][BF₄] | 0.516(T/K) + 252.959 | 1.17 |
| 10b* | [b₂Nic][Tf₂N] | 0.643(T/K) + 517.649 | 1.15 |
| 11b | [hpy][Tf₂N] | 0.679(T/K) + 412.673 | 1.54 |
| 12a | [hmpy][Br] | 0.545(T/K) + 181.738 | 0.82 |
| 12b* | [hmpy][Tf₂N] | 0.651(T/K) + 432.054 | 1.07 |
| 13b* | [hmmpy][Tf₂N] | 1.617(T/K) + 140.869 | 1.45 |
| 15b | [hpeepy][Tf₂N] | 1.082(T/K) + 447.708 | 2.04 |
| 16b | [hDMApy][Tf₂N] | 0.729(T/K) + 413.696 | 1.43 |
| 17b* | [hmDMApy][Tf₂N] | 1.838(T/K) + 153.285 | 1.6 |
| 20b | [ompy][Tf₂N] | 0.804(T/K) + 431.922 | 1.57 |
| 22f | ECOENG 41M | 0.307(T/K) + 551.329 | 0.56 |
| 23a | [hmim][Br] | 0.541(T/K) + 183.811 | 1.28 |
| 23b* | [hmim][Tf₂N] | 0.651(T/K) + 391.932 | 1.51 |
| 23d | [hmim][BF₄] | 0.560(T/K) + 250.871 | 0.88 |
| 24b | [hmmim][Tf₂N] | 0.626(T/K) + 501.967 | 1.29 |
| 25b* | [perfluoro-hmim][Tf₂N] | 0.861(T/K) + 472.111 | 2.06 |
| 26a | [omim][Br] | 0.546(T/K) + 231.078 | 0.98 |
| 26b | [omim][Tf₂N] | 0.739(T/K) + 437.427 | 1.74 |
| 26d | [omim][BF₄] | 0.608(T/K) + 327.89 | 1.78 |
| 27e | [N₄₄₄][doc] | 1.990(T/K) + 738.391 | 3.49 |
| 28g | ECOENG 500 | 1.095(T/K) + 743.112 | 1.98 |

*indicates that the correlation was fit to data from two or more separate runs.

Viscosities

Since ILs are more viscous than conventional solvents, viscosity is an important property. Increased pumping costs may be a limiting factor in the selection of ILs for various applications. However, it should be noted that in most applications, ILs will be used in mixtures with other, less viscous compounds. For instance, when used as a reaction solvent, the selected aminopyridinium or piperidino pyridinium containing compound or preparation will contain the reactants and the products. The presence of these other compounds may well significantly reduce the viscosity of the mixture.

It should be noted that the presence of water as an impurity in ILs will reduce the viscosity substantially.[71,72] Therefore, the water content of all the ILs, was measured immediately after the viscosity measurements by Karl-Fischer titration or Coulometry. The water contents of the [Tf₂N] ILs are below 200 ppm, which should not have a substantial effect on the viscosities. The water contents of the ILs with [BF₄] and [EtSO₄] anions have water contents as high as 350 ppm and 700 ppm, respectively. This could result in values that are 3% and 6% lower than the dry IL values, respectively.

In addition, the presence of halide impurities in ILs can dramatically increase the viscosity. However, all ILs studied here contained less than 10 ppm Br⁻, so the effect of the halide impurity of the viscosity reported here will be negligible.

Figure 31:
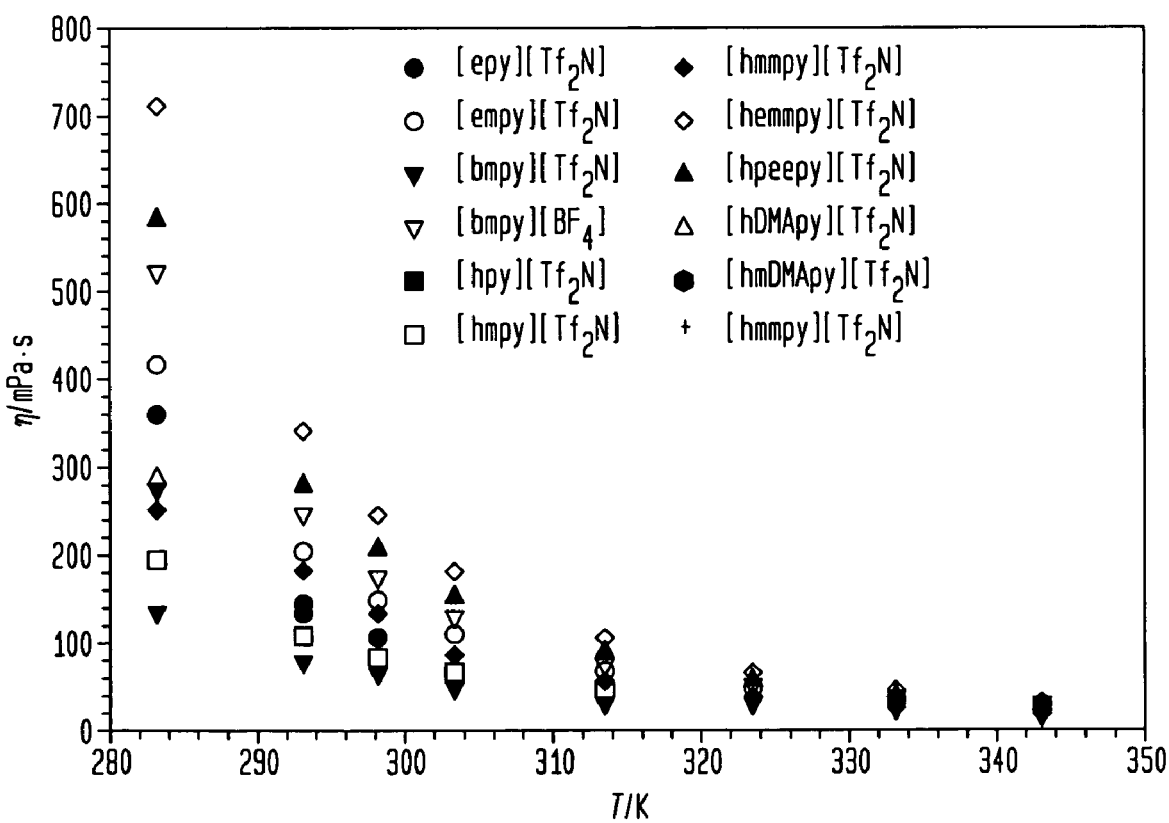
FIG. 31, according to one embodiment of the invention, presents the viscosities (η) of pyridinium-based ionic liquids as a function of temperature (T): ● [epy][Tf$_2$N]; ○, [empy][Tf$_2$N]; ▼, [bmpy][Tf$_2$N]; ∇, [bmpy][BF$_4$]; ■, [hpy][Tf$_2$N]; □, [hmpy][Tf$_2$N]; ♦, [hmmpy][Tf$_2$N]; ◇, [hemmpy][Tf$_2$N]; ▲, [hpeepy][Tf$_2$N]; △, [hDMApy][Tf$_2$N]; ●, [hmDMApy][Tf$_2$N]; +, [hmmmpy][Tf$_2$N].

Viscosities were measured at temperatures between 283 K and 343 K for twenty-two different compounds. These values are shown in Table 34. The viscosities for all the pyridinium ILs are shown in FIG. 31.

TABLE 34

Viscosities (η) as a function of temperature (T), with water content for the ILs defined in Table 29.

| Compound | IL | η/(mPa·s) | | | | | | | | Water content/ppm |
|---|---|---|---|---|---|---|---|---|---|---|
| | | T = 283 K | T = 293 K | T = 298 K | T = 303 K | T = 313 K | T = 323 K | T = 333 K | T = 343 K | |
| 1c | [epy][EtSO₄] | 356 | 183 | 137 | 105 | 66 | 43 | 31 | 23 | 683 |
| 2c | [empy][EtSO₄] | 414 | 204 | 150 | 114 | 70 | 45 | 32 | 23 | 256 |
| 4c | [Et₂Nic][EtSO₄] | 19,610 | 5675 | 3173 | 1986 | 846 | 405 | 223 | 130 | 659 |
| 6b | [bmpy][Tf₂N] | 138 | 80 | 63 | 51 | 34 | 24 | 18 | 14 | 28 |
| 6d | [bmpy][BF₄] | 517 | 246 | 177 | 132 | 78 | 48 | 33 | 23 | 327 |
| 10b | [b₂Nic][Tf₂N] | 1830 | 774 | 531 | 379 | 203 | 117 | 73 | 48 | 40 |
| 11b | [hpy][Tf₂N] | 189 | 106 | 80 | 64 | 42 | 29 | 21 | 16 | 107 |
| 12b | [hmpy][Tf₂N] | 197 | 130 | 85 | 67 | 44 | 30 | 22 | 16 | 152 |
| 13b | [bmmpy][Tf₂N] | 251 | 136 | 104 | 81 | 52 | 35 | 24 | 18 | 30 |
| 14b | [hemmpy][Tf₂N] | 708 | 338 | 245 | 182 | 106 | 64 | 42 | 29 | 258 |
| 15b | [hpeepy][Tf₂N] | 579 | 281 | 206 | 155 | 93 | 57 | 39 | 27 | 132 |
| 16b | [hDMApy][Tf₂N] | 285 | 146 | 111 | 86 | 54 | 36 | 25 | 15 | 68 |
| 17b | [hmDMApy][Tf₂N] | 278 | 148 | 112 | 87 | 55 | 37 | 26 | 19 | 33 |
| 20b | [ompy][Tf₂N] | 268 | 146 | 112 | 88 | 56 | 27 | 26 | 19 | 70 |
| 21b | [emim][Tf₂N] | 52 | 36 | 32 | 26 | 19 | 15 | 12 | 9 | 204 |
| 22f | ECOENG 41M | 4070 | 1676 | 1033 | 731 | 392 | 228 | 146 | 98 | 831 |
| 22h | [bmim][CH₃CO₂] | 1630 | 646 | 440 | 309 | 165 | 97 | 62 | 42 | 11,003 |
| 22i | [bmim][CF₃CO₂] | 155 | 89 | 70 | 53 | 35 | 24 | 18 | 13 | 2246 |
| 23b | [hmim][Tf₂N] | 148 | 86 | 68 | 55 | 37 | 26 | 19 | 15 | 31 |
| 24b | [hmmim][Tf₂N] | 317 | 171 | 131 | 101 | 63 | 42 | 30 | 22 | 13 |
| 27e | [N₄₄₄₄][doc] | | | 12,100 | 7560 | 3180 | 1470 | 755 | 411 | |
| 28g | ECOENG 500 | 10,240 | 2780 | 2790 | 1910 | 964 | 511 | 300 | 187 | 1044 |

Increasing the alkyl chain on the nitrogen of the cation increases the viscosity, which is shown by comparing [ompy][Tf$_2$N] with [hmpy][Tf$_2$N] and [bmpy][Tf$_2$N]. An increase in viscosity with increasing alkyl chain length on the cation is in agreement with several papers on imidazolium-based ionic liquids.[11,49,55,67,68] ILs with the [Tf$_2$N] anion are less viscous than those with the [BF$_4$] or [EtSO$_4$] anions. Adding more methyl groups to the pyridinium ring increases viscosity, as seen by comparing [hpy][Tf$_2$N] with [hmpy][Tf$_2$N] and [hmmpy][Tf$_2$N]. The dimethylamino group on the 4 position of the ring increases viscosity but only as much as a couple methyl groups attached to the ring. Increasing the chain length of the substituent groups off the aromatic rings lowers the viscosity. This effect may be caused by the longer chains creating steric hindrance that prevents close associations between ions.

Figure 32:
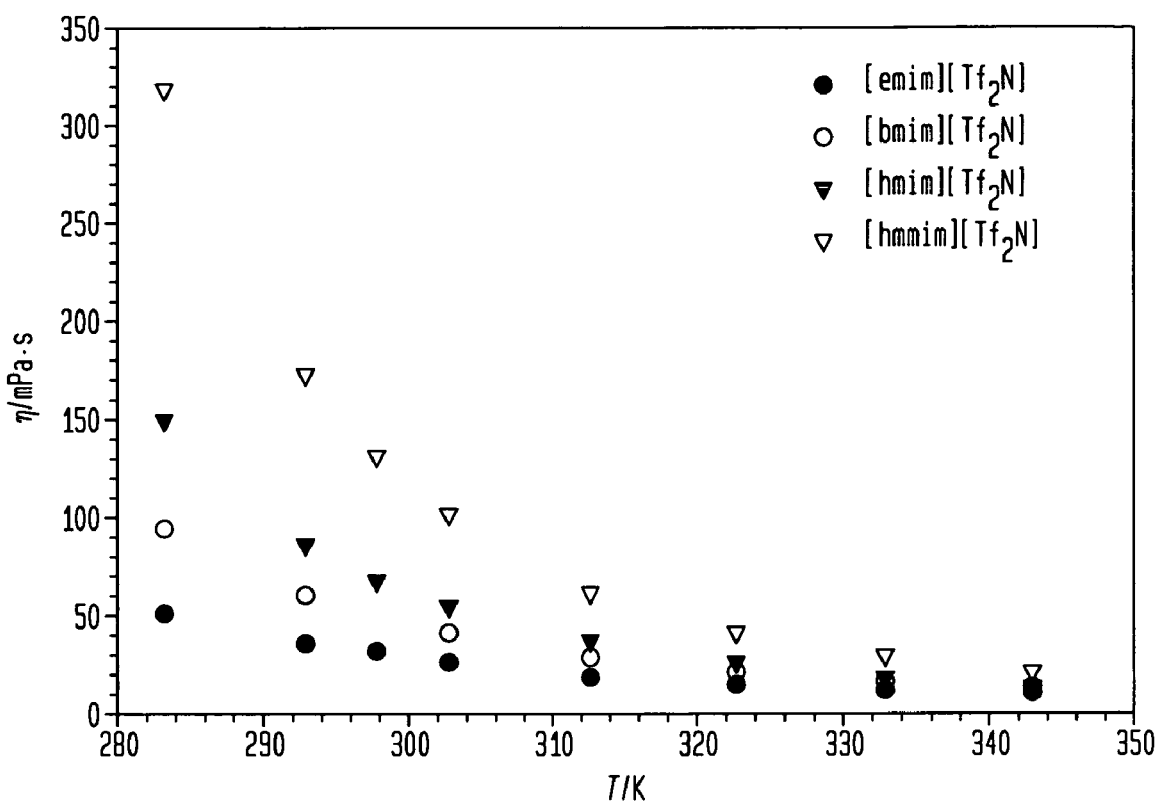
FIG. 32, according to one embodiment of the invention, presents the viscosities (η) of imidazolium-based ionic liquids as a function of temperature (T): ●, [emim][Tf$_2$N]; ○, [bmim][Tf$_2$N]; ▼, [hmim][Tf$_2$N]; ∇, [hmmim][Tf$_2$N].

FIG. 32 shows the viscosity of the imidazolium ILs that were measured. Single point comparisons at 293 K for [emim][Tf$_2$N], 36 mPa·s in this study, show good agreement with literature values of 28-34 mPa·s.[11,41,69,70] Comparison of the viscosity of [hmim][Tf$_2$N] at 293 K from this study, with a value of 86 mPa·s, differs from the value reported by Fitchett et al. of 78 mPa·s.[68] However, the water content of the samples also differs by nearly 700 ppm, which may account for the difference in viscosity values. The viscosity for [bmim][CF$_3$CO$_2$] at 293 K of 89 mPa·s differs slightly from the value reported by Bonhote et al. of 73 mPa·s.[11] Again this difference in viscosity is most likely due to the difference in water content of the ILs used (0.0022 mass fraction vs. 0.015 mass fraction and 0.03 mass fraction for Bonhote et al.). The same trends are observed for the imidazolium ILs as for the pyridinium ILs above.

Figure 6:
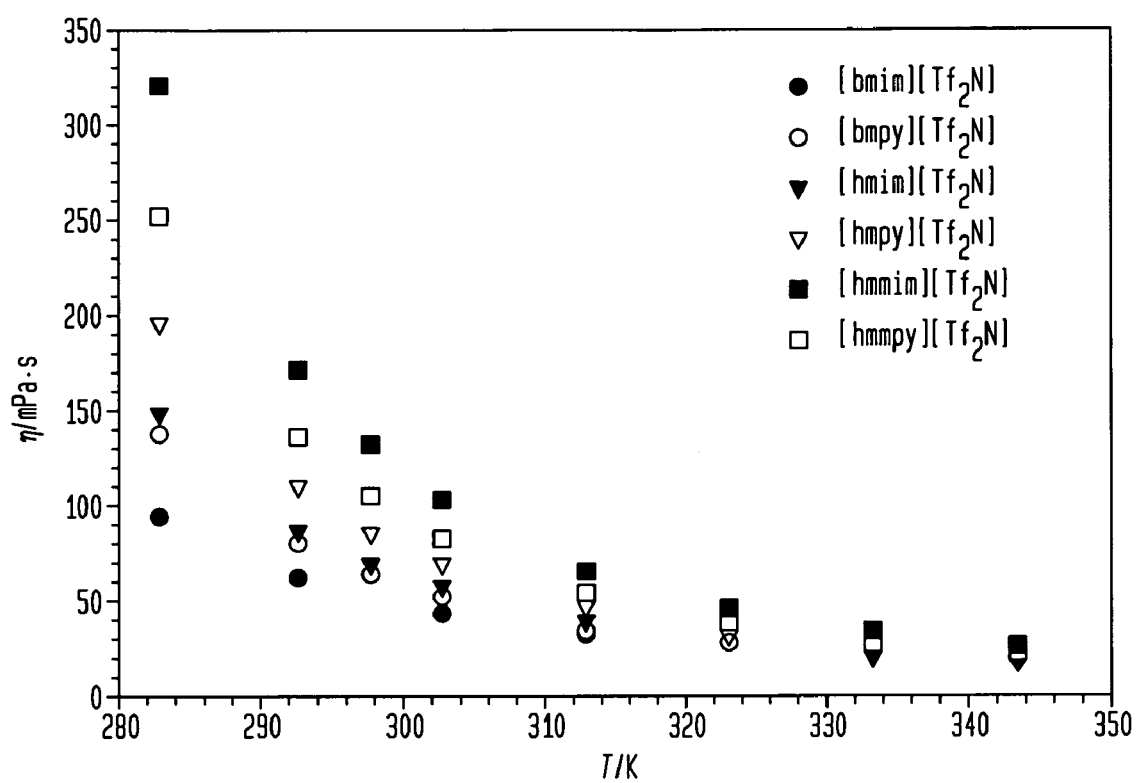
FIG. 6, according to one embodiment of the invention, presents a comparison of the viscosities (η) of pyridinium- and imidazolium-based ionic liquids as a function of temperature (T): ●, [bmim][Tf$_2$N]; ○, [bmpy][Tf$_2$N]; ▼, [hmim][Tf$_2$N]; ∇, [hmpy][Tf$_2$N]; ■, [hmmim][Tf$_2$N]; □, [hmmpy][Tf$_2$N].

FIG. 6 compares [bmpy][Tf$_2$N] with [bmim][Tf$_2$N] [35], [hmpy][Tf$_2$N] with [hmim][Tf$_2$N], and [hmmpy][Tf$_2$N] with [hmmim][Tf$_2$N]. Viscosity increases with increasing alkyl chain length on the cation, which is in agreement with previous studies of viscosity for imidazolium Ils.[11,49,55,67,68] Moreover, the addition of another methyl group to the ring further increases the viscosity. The viscosities of pyridinium ILs are only slightly more viscous than equivalent imidazolium ILs in most cases.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

BIBLIOGRAPHY

The following references are hereby specifically incorporated herein by reference:

1. Brennecke, J. F. and Maginn, E. J., (2001), *AlChE Journal,* 47(11):2384-2389.
2. U.S. Pat. No. 5,827,602—Koch et al.
3. U.S. Pat. No. 6,579,343—Brennecke et al.
4. Brunelle, D., et al. (1984), *Tetrahedron Letters,* 25 (32): 3383-3386.
5. Yoshoda et al. (1989), *Tetrahedron Letters,* 30 (51): 7199-7202.
6. Kupetis, G. -K., et al. (2002), *Monatshefte fur Chemie,* 13: 313-321.
7. Anthony, J. L., Z. Gu, L. A. Blanchard, E. J. Maginn, and J. F. Brennecke, "Gas Solubility in Ionic Liquids", American Chemical Society Annual Meeting, April (2001c).
8. Blanchard, L. A., et al., (1999), *Nature,* 399, 28.
9. Blanchard, L. A., and J. F. Brennecke, (2001a), *Ind. Eng. Chem. Res.,* 40: 287.
10. Blanchard, L. A., Z. Gu, and J. F. Brennecke, J. F., (2001b), *J. Phys. Chem. B,* 105, 2437.
11. Bonhôte, P., et al., (1996), *Inorg. Chem.,* 35(5): 1168.
12. Chang, K., (2001), "With a Splash of Salt", *New York Times,* Apr. 24, 2001.
13. Chauvin, Y., and H. Olivier-Bourbigou, (1995), *Chemtech,* 25 (9):26-30.
14. *The Economist,* "Ionic Solvents; A Working Solution?" Jun. 19, 1999.
15. Fadeev, A. G., and M. M. Meagher, (2001), *Chem. Commun.,* (03), pp. 295-296.
16. Guterman, L., (1998), "*Weird Mixtures Replace Toxic Solvents*", New Scientist, Sept. 5 Issue, p. 1313.
17. Crosthwaite, J. M, et al. (2005), *J. Chem. Thermodynamics,* 37:559-568.
18. Tokuda, H., et al., (2004), *J. Phys. Chem. B.,* 108: 16593-16600.
19. U.S. Pat. No. 6,939,972—Kuner, et al., (2005).
20. U.S. Pat. No. 6,638,946—Meth-Cohn, et al., (2003).
21. Gen, Xi Guan, et al., (1998), *Chemical Reagent,* 20(2): 119-120.
22. Hanke, C. G., S. L. Price, and R. M. Lynden-Bell, (2001), *Mol. Phys.,* 99(10): 801.
23. Harold, M. P., and B. A. Ogunnaike, (2000), *AlChE J.,* 46: 2123.
24. MacFarlane, D. R., et al., (1999), *J. Phys. Chem. B,* 103(20): 4164.
25. Pernak, J., et al. (2001), *Ind. Eng. Chem. Res.,* 40: 2379.
26. Renner, R. (August, 2001), *Scientific American.*
27. Seddon, K. R. (1996), *Kinetics and Catalysis,* 37(5): 693.
28. Seddon, K. R., et al. (2000), *Pure Appl. Chem.,* 72(12): 2275.
29. Scovazzo, P., et al. (April, 2001), "Supported Ionic Liquid Membranes and Facilitated Ionic Liquid Membranes", American Chemical Society Annual Meeting.
30. Visser, A. E., et al. (2000), *Ind. Eng. Chem. Res.,* 39, 3596 (2000).
31. Welton, T., (1999), *Chem. Rev.,* 99, 2071 (1999).
32. Wilkes, J. S. and M. J. Zaworotko, (1992), *J. Chem. Soc., Chem. Commun.,* (13), p. 965-967.
33. J. F. Brennecke, E. J. Maginn (2001), *AlChE J.,* 47: 2384-2389.
34. P. Wasserscheid, W. Keim, Angew. (2000) *Chem.-Int. Edit.* 39 3773-3789.
35. T. Welton, (2004) *Coord. Chem. Rev.* 248: 2459-2477.
36. J. S. Wilkes, (2004) *J. Mol. Catal. A.* 214: 11-17.
37. R. Hagiwara, Y. Ito, (2000) *J. Fluor. Chem.* 105: 221-227.
38. H. Tokuda, et al., (2000) *J. Phys. Chem. B.* 108 :16593-16600.
39. M. E. Van Valkenburg, et al. (2005) *Thermochim. Acta.* 425:181-188.
40. Nasakin, O. E., et al., (1998), *Chem. of Heterocylic Compounds,* 34(10): 1177-1180.
41. A. Noda, et al., (2001) *J. Phys. Chem. B.* 105: 4603-4610.
42. S. V. Dzyuba, R. A. Bartsch, (2002) *ChemPhysChem.* 3: 161-166.

43. J. G. Huddleston, et al., (2001) *Green Chem.* 3: 156-164.
44. P. A. Z. Suarez, et al. (1998) *Chim. Phys.-Chim. Biol.* 95: 1626-1639.
45. H. L. Ngo, K. LeCompte, L. Hargens, A. B. McEwen, (2000) *Thermochim. Acta.* 357: 97-102.
46. H. Matsumoto, H. Kageyama, Y. Miyazaki, (2002) *Chem. Commun.* 1726-1727.
47. J. D. Holbrey, K. R. Seddon, J. Chem. Soc.-Dalton Trans. (1999) 2133-2139.
48. D. R. MacFarlane, et al., (2001) *Chem. Commun.,* 1430-1431.
49. L. C. Branco, et al. (2002) *Chem. Eur. J.* 8:3671-3677.
50. W. H. Awad, et al., (2004) *Thermochim. Acta.* 409: 3-11.
51. M. Kosmulski, et al., (2004) *Thermochim. Acta.* 412: 47-53.
52. K. Kim, et al., (2004) *Fluid Phase Equil.* 218: 215-220.
53. J. Magee, Heat Capacity and Enthalpy of Fusion for 1-Butyl-3-Methyl-Imidazolium Hexafluorophosphate, 17th IUPAC Conference on Chemical Thermodynamics (ICCT 2002), Rostock, Germany, 2002.
54. J. D. Holbrey, W. M. Reichert, R. G. Reddy, R. D. Rogers, Heat Capacities of Ionic Liquids and Their Applications as Thermal Fluids. in: K. R. Seddon and R. D. Rogers (Eds.), *Ionic Liquids as Green Solvents*, ACS Symp. Ser. 856, American Chemical Society, Washington, D.C., 2003, pp. 121-133.
55. K. R. Seddon, A. Stark, M. J. Torres, Viscosity and density of 1-alkyl-3-methylimidazolium ionic liquids. in: K. R. Seddon and R. D. Rogers (Eds.), *Clean Solvents*, ACS Symposium Series 819, American Chemical Society, Washington, D.C., 2002, pp. 34-49.
56. O. O. Okoturo, T. J. VandNoot, (2004) *J. Electroanal. Chem.* 568: 167-181.
57. M. Yoshizawa, W. Xu, C. A. Angell, (2003) *J. Am. Chem. Soc.* 125:15411-15419.
58. C. Patrascu, et al., (2004) *Heterocycles.* 63: 2033-2041.
59. A. Heintz, D. Klasen, J. K. Lehmann, (2002) *J. Solut. Chem.* 31: 467-476.
60. Z. Liu, et al., (2003) *Chem. Eur. J.* 9: 3897-3903.
61. H. Ohno, M. Yoshizawa, (2002) *Solid State Ionics.* 154-155: 303-309.
62. L. Cammarata, et al., (2001) *Phys. Chem. Chem. Phys.* 3:5192-5200.
63. C. P. Fredlake, et al., (2004) *J. Chem. Eng. Data.* 49: 954-964.
64. J. M. Crosthwaite, et al., (2004) *J. Phys. Chem. B.* 108: 5113-5119.
65. M. J. Muldoon, Ph.D Thesis, University of Strathclyde, 2003.
66. K. R. Seddon, A. Stark, M. J. Torres, (2000) *Pure Appl. Chem.* 72:2275-2287.
67. A. P. Abbott, (2004) *ChemPhysChem.* 5:1242-1246.
68. B. D. Fitchett, T. N. Knepp, J. C. Conboy, *J. Electrochem. Soc.* 151 (2004) E219-E225.
69. H. Matsumoto, et al., (2000) *Chem. Lett.* 29:922-923.
70. A. B. McEwen, et al., (1999) *J. Electrochem. Soc.* 146:1687-1695.
71. J. A. Widegren, et al., (2005) *Chem. Commun.* (12), 1610-1612.
72. K. R. Seddon, et al., (2000) *Pure Appl. Chem.* 72:2272-2287.

What is claimed is:

1. A composition comprising an aminopyridinium cation, said cation comprising a structure having the following formula:

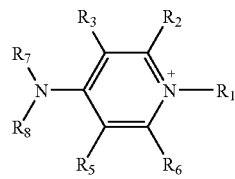

wherein: $R_1$ is butyl or hexyl, $R_3$ is $C_nH_{2n+1}$, and n is 1 to 16, and $R_2$, $R_5$, $R_6$, $R_7$, and $R_8$ are each $C_pH_{2p+1}$, and wherein p is 0 to 16.

2. The composition of claim 1, wherein $R_1$ is butyl.
3. The composition of claim 2, wherein $R_3$ is methyl.
4. The composition of claim 3, wherein $R_7$, and $R_8$ are each methyl.
5. The composition of claim 4, wherein said cation comprises 1-butyl-3-methyl-4-(dimethylamino)pyridinium.
6. The composition of claim 1, wherein $R_1$ is hexyl.
7. The composition of claim 6, wherein $R_3$ is methyl.
8. The composition of claim 7, wherein $R_7$, and $R_8$ are each methyl.
9. The composition of claim 8, wherein said cation comprises 1-hexyl-3-methyl-4-(dimethylamino)pyridinium.
10. A composition comprising a pyridinium cation, said cation comprising a structure having the following formula:

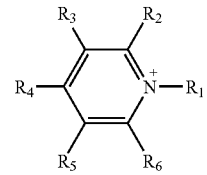

wherein: $R_1$ is hexyl, $R_3$ and $R_5$ are each $C_nH_{2n+1}$, and n is 1 to 16, $R_2$ and $R_6$ are each $C_pH_{2p+1}$, and wherein p is 0 to 16, and $R_4$ is cyclohexyl.

11. The composition of claim 10, wherein $R_3$, and $R_5$ are each methyl.
12. The composition of claim 11, wherein said cation comprises 1-hexyl-3,5-dimethylpyridinium.
13. The composition of claim 11, wherein $R_2$ is ethyl.
14. The composition of claim 13 wherein said cation comprises 1-hexyl-2-ethyl-3,5-dimethylpyridinium.
15. The composition of claim 10, wherein $R_3$, and $R_5$ are each ethyl.
16. The composition of claim 15, wherein $R_2$ is propyl.
17. The composition of claim 16, wherein said cation comprises 1-hexyl-2-propyl-3,5-diethylpyridinium.
18. A composition comprising a pyridinium cation, said cation comprising a structure having the following formula:

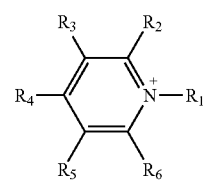

wherein: $R_1$ is hexyl or octyl, $R_3$ is $C_nH_{2n+1}$, and n is 1 to 16, and $R_2$, $R_5$, and $R_6$ are each $C_pH_{2p+1}$, and wherein p is 0 to 16, and $R_4$ is cyclohexyl.

19. The composition of claim 18, wherein $R_3$ is methyl.
20. The composition of claim 19, wherein said cation comprises 1-octyl-3-methylpyridinium.
21. The composition of claim 19, wherein said cation comprises 1-hexyl-3-methylpyridinium.

22. A composition comprising an ionic compound, wherein said ionic compound comprises a structure having the following formula:

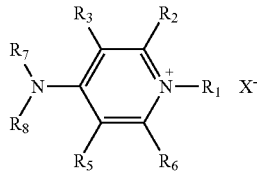

wherein: $R_1$ is butyl or hexyl, $R_3$ is $C_nH_{2n+1}$, and n is 1 to 16, $R_2$, $R_5$, $R_6$, $R_7$, and $R_8$ are each $C_pH_{2p+1}$, and wherein p is 0 to 16, and X is an anion.

23. The composition of claim 22 wherein the anion is other than chloride.

24. The composition of claim 23, wherein X is one or more members of the group consisting of: $(CF_3SO_2)_2N$, $(CN)_2N$, bis(trifluoromethylsulfonyl) imide, ethylsulfate, ester ethyl sulfate, bromide, chloride, $Tf_2N$, $BF_4$ or bromide.

25. The composition of claim 22 wherein the ionic compound is a liquid.

26. The composition of claim 22, wherein $R_1$ is butyl.

27. The composition of claim 26, wherein $R_3$ is methyl.

28. The composition of claim 27, wherein $R_7$, and $R_8$ are each methyl.

29. The composition of claim 28, wherein said ionic compound comprises a 1-butyl-3-methyl-4-(dimethylamino)pyridinium cation.

30. The composition of claim 29, wherein said composition comprises 1-butyl-3-methyl-4-dimethylaminopyridinium $(CN)_2N$.

31. The composition of claim 29, wherein said composition comprises 1-butyl-3-methyl-4-dimethylaminopyridinium $CF_3CO_2$.

32. The composition of claim 29, wherein said composition comprises 1-butyl-3-methyl-dimethylaminopyridinium $BF_4$.

33. The composition of claim 29, wherein said composition comprises 1-butyl-3-methyl-dimethylaminopyridinium $NO_3$.

34. The composition of claim 29, wherein said composition comprises 1-butyl-3-methyl-4-dimethylaminopyridinium bromide.

35. The composition of claim 22, wherein $R_1$ is hexyl.

36. The composition of claim 35, wherein $R_3$ is methyl.

37. The composition of claim 36, wherein $R_7$, and $R_8$ are each methyl.

38. The composition of claim 37, wherein said ionic compound comprises a 1-hexyl-3-methyl-4-(dimethylamino)pyridinium cation.

39. The composition of claim 38, wherein said composition comprises 1-hexyl-3-methyl-dimethylaminopyridinium bromide.

40. The composition of claim 38, wherein said composition comprises 1-hexyl-3-methyl-dimethylaminopyridinium $(CF_3SO_2)_2N$.

41. A composition comprising an ionic compound, wherein said ionic compound comprises a structure having the following formula:

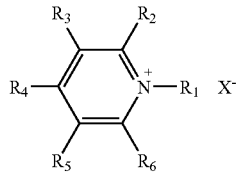

wherein: $R_1$ is hexyl, $R_3$ and $R_5$ are each $C_nH_{2n+1}$, and n is 1 to 16, and $R_2$ and $R_6$ are each $C_pH_{2p+1}$, and wherein p is 0 to 16, and $R_4$ is cyclohexyl.

42. The composition of claim 41 wherein the anion is other than chloride.

43. The composition of claim 42, wherein X is one or more members of the group consisting of: $(CF_3SO_2)_2N$, $(CN)_2N$, bis(trifluoromethylsulfonyl) imide, ethylsulfate, ester ethyl sulfate, bromide, chloride, $Tf_2N$, $BF_4$ or bromide.

44. The composition of claim 41 wherein the ionic compound is a liquid.

45. The composition of claim 41, wherein $R_3$, and $R_5$ are each methyl.

46. The composition of claim 45, wherein said ionic compound comprises a 1-hexyl-3,5-dimethylpyridinium cation.

47. The composition of claim 45, wherein $R_2$ is ethyl.

48. The composition of claim 47, wherein said ionic compound comprises a 1-hexyl-2-ethyl-3,5-dimethylpyridinium cation.

49. The composition of claim 47, wherein $R_3$ is methyl.

50. A composition comprising an ionic compound, wherein said ionic compound comprises a structure having the following formula:

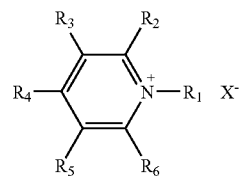

wherein: $R_1$ is hexyl or octyl, $R_3$ is $C_nH_{2n+1}$, and n is 1 to 16, and $R_2$, $R_5$, and $R_6$ are each $C_pH_{2p+1}$, and wherein p is 0 to 16, and $R_4$ is cyclohexyl.

51. The composition of claim 50 wherein the anion is other than chloride.

52. The composition of claim 51, wherein X is one or more members of the group consisting of: $(CF_3SO_2)_2N$, $(CN)_2N$, bis(trifluoromethylsulfonyl) imide, ethylsulfate, ester ethyl sulfate, bromide, chloride, $Tf_2N$, $BF_4$ or bromide.

53. The composition of claim 50, wherein the ionic compound is a liquid.

54. The composition of claim 52, wherein $R_2$ is propyl.

55. The composition of claim 54, wherein said cation comprises a 1-hexyl-2-propyl-3,5-diethylpyridinium compound.

56. The composition of claim 55, wherein $R_3$, and $R_5$ are each ethyl.

57. The composition of claim 50, wherein said ionic compound comprises a 1-octyl-3-methylpyridinium compound.

58. The composition of claim 50, wherein said ionic compound comprises a 1-hexyl-3-methylpyridinium compound.

59. A composition comprising an ionic compound including a 1-ethyl nicotinic acid ethyl ester cation.

60. The composition of claim 59, wherein the ionic compound includes an anion other than chloride.

61. The composition of claim 60, wherein the anion is one or more members of the group consisting of: $(CF_3SO_2)_2N$, $(CN)_2N$, bis(trifluoromethylsulfonyl) imide, ethylsulfate, ester ethyl sulfate, bromide, chloride, $Tf_2N$, $BF_4$ or bromide.

62. The composition of claim 59, wherein the ionic compound is a liquid.

* * * * *